US012637454B2

(12) United States Patent
Benz et al.

(10) Patent No.: US 12,637,454 B2
(45) **Date of Patent: *May 26, 2026**

(54) HETEROCYCLIC MONOACYLGLYCEROL LIPASE (MAGL) INHIBITORS

(71) Applicant: Hoffmann-La Roche Inc., Little Falls, NJ (US)

(72) Inventors: Joerg Benz, Rheinfelden (DE); Uwe Grether, Efringen-Kirchen (DE); Benoit Hornsperger, Altkirch (FR); Carsten Kroll, Basel (CH); Bernd Kuhn, Reinach (CH); Fionn O'Hara, Basel (CH); Hans Richter, Grenzach-Wyhlen (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 1178 days.

This patent is subject to a terminal disclaimer.

(21) Appl. No.: 17/552,792

(22) Filed: Dec. 16, 2021

(65) Prior Publication Data

US 2022/0213093 A1 Jul. 7, 2022

Related U.S. Application Data

(63) Continuation of application No. PCT/EP2020/068320, filed on Jun. 30, 2020.

(30) Foreign Application Priority Data

Jul. 3, 2019 (EP) .................................... 19184218

(51) Int. Cl.
*C07D 471/04* (2006.01)
*C07D 519/00* (2006.01)

(52) U.S. Cl.
CPC ......... *C07D 471/04* (2013.01); *C07D 519/00* (2013.01)

(58) Field of Classification Search
CPC ................ C07D 471/04; C07D 519/00; C07D 491/107; A61K 9/2009; A61K 9/2054; A61K 9/2059; A61K 9/485; A61K 9/4858; A61K 9/4866; A61K 31/4985; A61P 25/00; A61P 25/28; A61P 29/00; A61P 35/00
See application file for complete search history.

(56) References Cited

U.S. PATENT DOCUMENTS 4,391,978 A 7/1983 Imhof et al.
4,454,130 A 6/1984 Tominaga et al.
4,632,925 A 12/1986 Mullin, Jr. et al.
4,956,359 A 9/1990 Taylor, Jr. et al.
6,673,908 B1 * 1/2004 Stanton, Jr. ........ C07K 14/7151 435/6.16
7,488,737 B2 2/2009 Xie et al.
8,614,209 B2 12/2013 Webster et al.
10,106,556 B2 10/2018 Ikeda et al.
10,610,520 B2 4/2020 Ikeda et al.
11,390,610 B2 7/2022 Benz et al.
11,420,961 B2 8/2022 Benz et al.
11,608,347 B2 3/2023 Petersen et al.
11,802,133 B2 10/2023 Bell et al.
11,814,375 B2 11/2023 Benz et al.
11,981,661 B2 5/2024 Benz et al.
2015/0018335 A1 1/2015 Cisar et al.
2020/0255439 A1 8/2020 Kamata et al.
2020/0299277 A1 9/2020 Benz et al.
2020/0308158 A1 10/2020 Bell et al.
2020/0308190 A1 10/2020 Bell et al.
2020/0392125 A1 12/2020 Benz et al.
2021/0024546 A1 1/2021 Petersen et al.
2021/0053973 A1 2/2021 Ali et al.
2021/0094943 A1 4/2021 Benz et al.
2021/0094971 A1 4/2021 Grether et al.
2021/0094972 A1 4/2021 Benz et al.
2021/0094973 A1 4/2021 Gobbi et al.
2021/0107920 A1 4/2021 Bell et al.
2021/0107921 A1 4/2021 Benz et al.
2021/0277020 A1 9/2021 Anselm et al.

(Continued)

FOREIGN PATENT DOCUMENTS

EP 3279191 A1 2/2018
EP 3312177 A2 4/2018

(Continued)

OTHER PUBLICATIONS

Mikhlina et al., Khimiya Geterotsiklicheskikh Soedinenii (1969), (3), 547-9. (Year: 1969).*

(Continued)

*Primary Examiner* — James H Alstrum-Acevedo
*Assistant Examiner* — Chantal Adlam
(74) *Attorney, Agent, or Firm* — Zong-Qiang Bill Tian

(57) ABSTRACT

The invention provides new heterocyclic compounds having the general formula (I)

(I)

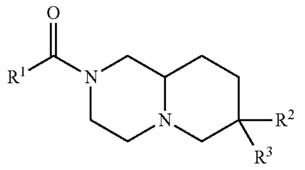

wherein $R^1$ to $R^3$ are as described herein, compositions including the compounds, processes of manufacturing the compounds and methods of using the compounds.

17 Claims, No Drawings

(56) References Cited

U.S. PATENT DOCUMENTS

| | | | |
|---|---|---|---|
| 2021/0387999 A1 | 12/2021 | Kuhn et al. | |
| 2022/0098176 A1 | 3/2022 | Benz et al. | |
| 2022/0106328 A1 | 4/2022 | Benz et al. | |
| 2022/0135591 A1 | 5/2022 | Benz et al. | |
| 2022/0202963 A1 | 6/2022 | Collin et al. | |
| 2022/0213093 A1 | 7/2022 | Benz et al. | |
| 2022/0220373 A1 | 7/2022 | Benz et al. | |
| 2022/0242876 A1 | 8/2022 | Kroll et al. | |
| 2022/0267349 A1 | 8/2022 | Benz et al. | |
| 2022/0275005 A1 | 9/2022 | Grether et al. | |
| 2023/0117324 A1 | 4/2023 | Bell et al. | |
| 2023/0183224 A1 | 6/2023 | Bell et al. | |
| 2023/0203056 A1 | 6/2023 | Benz et al. | |
| 2024/0150373 A1 | 5/2024 | Bell et al. | |
| 2024/0199587 A1 | 6/2024 | Amoussa et al. | |

FOREIGN PATENT DOCUMENTS

| | | | |
|---|---|---|---|
| JP | 2010-520217 | A | 6/2010 |
| JP | 7269943 | B2 | 4/2023 |
| WO | 01/07043 | A1 | 2/2001 |
| WO | 2004/000832 | A1 | 12/2003 |
| WO | 2004/096763 | A1 | 11/2004 |
| WO | 2005/066187 | A1 | 7/2005 |
| WO | 2006/000914 | A1 | 1/2006 |
| WO | 2006/001894 | A1 | 1/2006 |
| WO | 2006/051410 | A1 | 5/2006 |
| WO | 2007/002057 | A1 | 1/2007 |
| WO | 2007/098418 | A1 | 8/2007 |
| WO | 2007/117557 | A2 | 10/2007 |
| WO | 2008/109336 | A1 | 9/2008 |
| WO | 2009/058347 | A1 | 5/2009 |
| WO | 2009/074789 | A1 | 6/2009 |
| WO | 2009/112845 | A1 | 9/2009 |
| WO | 2010/106333 | A1 | 9/2010 |
| WO | 2011/059118 | A1 | 5/2011 |
| WO | 2012/155199 | A1 | 11/2012 |
| WO | 2013/028474 | A1 | 2/2013 |
| WO | 2013/059118 | A1 | 4/2013 |
| WO | 2013/103973 | | 7/2013 |
| WO | 2013/179024 | A1 | 12/2013 |
| WO | 2014/099633 | A2 | 6/2014 |
| WO | 2015/179559 | A2 | 11/2015 |
| WO | 2016/014975 | A2 | 1/2016 |
| WO | 2016/109501 | A1 | 7/2016 |
| WO | 2016/180536 | A1 | 11/2016 |
| WO | 2016/185279 | A1 | 11/2016 |
| WO | 2016/205590 | A1 | 12/2016 |
| WO | 2017/087854 | A1 | 5/2017 |
| WO | 2017/087858 | A1 | 5/2017 |
| WO | 2017/087863 | A1 | 5/2017 |
| WO | 2017/171100 | A1 | 10/2017 |
| WO | 2018/134698 | A1 | 7/2018 |
| WO | 2018/217809 | A1 | 11/2018 |
| WO | 2019/065791 | A1 | 4/2019 |
| WO | 2019/072785 | A1 | 4/2019 |
| WO | 2019/105915 | A1 | 6/2019 |
| WO | 2019/115660 | A1 | 6/2019 |
| WO | 2019/134985 | A1 | 7/2019 |
| WO | 2019/180185 | A1 | 9/2019 |
| WO | 2020/035424 | A1 | 2/2020 |
| WO | 2020/035425 | A1 | 2/2020 |
| WO | 2020/104494 | A1 | 5/2020 |
| WO | 2020/207941 | A1 | 10/2020 |
| WO | 2021/005034 | A1 | 1/2021 |
| WO | 2021/048036 | A1 | 3/2021 |
| WO | 2021/048242 | A1 | 3/2021 |
| WO | 2021/058416 | A1 | 4/2021 |
| WO | 2021/058444 | A1 | 4/2021 |
| WO | 2021/058445 | A1 | 4/2021 |
| WO | 2022/043284 | A1 | 3/2022 |
| WO | 2022/049134 | A1 | 3/2022 |

OTHER PUBLICATIONS

Arata et al., Chemical & Pharmaceutical Bulletin (1973), 21(6), 1248-53. (Year: 1973).*

Alpar, A., et al., "Endocannabinoids modulate cortical development by configuring Slit2/Robo1 signaling" Nat Commun 5(4421):1-13 (Jul. 17, 2014).

Ashton, K., et al., "Design and synthesis of novel amide AKTI inhibitors with selectivity over CDK2" Bioorg Med Chem Lett 21(18):5191-5196 (Sep. 15, 2011).

Aurora Fine Chemicals, Other Database, 1907579-56-9, (C26 H25 N3 O3), pp. 1; Creation Date May 10, 2016.

Barney, C., et al., "A convenient synthesis of hindered amines and α-trifluoromethylamines from ketones" Tetrahedron Lett 31(39):5547-5550 ( 1990).

Bernal-Chico, A., et al., "Blockade of Monoacylglycerol Lipase Inhibits Oligodendrocyte Excitotoxicity and Prevents Demyelination In Vivo" GLIA 63(1):163-176 (Jan. 1, 2015).

Chanda, P.K., et al., "Monoacylglycerol Lipase Activity Is a Critical Modulator of the Tone and Integrity of the Endocannabinoid System" Mol Pharmacol 78(6):996-1003 (Dec. 1, 2010).

Chang, J. et al., "Highly Selective Inhibitors of Monoacylglycerol Lipase Bearing a Reactive Group that is Bio-isosteric with Endocannabinoid Substrates" Chem Biol 19(5):579-588 (May 1, 2012).

Dugar, S. et al., "A Concise and Efficient Synthesis of Substituted Morpholines" Synthesis 47(5):712-720 (Mar. 1, 2015).

Duncan, M., et al., "Review article: endocannabinoids and their receptors in the enteric nervous system" Aliment Pharmacol Ther 22(8):667-683 (Oct. 15, 2005).

Enamine, CAS Registry Database, 931085-56-2, (Registry No. 931085-56-2), pp. 1; Submission Date Apr. 20, 2007.

Evano, G., et al., "Copper-Mediated Coupling Reactions and Their Applications in Natural Products and Designed Biomolecules Synthesis" Chem Rev 108(8):3054-3131 (Aug. 13, 2008).

Feliu, A., et al., "2-Arachidonoylglycerol Reduces Proteoglycans and Enhances Remyelination in a Progressive Model of Demyelination" J Neurosci 37(35):8385-8398 (Aug. 30, 2017).

Fray, M., et al., "Second generation N-(1,2-diphenylethyl)piperazines as dual serotonin and noradrenaline reuptake inhibitors: improving metabolic stability and reducing ion channel activity" Bioorg Med Chem Lett 20(12):3788-3792 (Jun. 15, 2010).

Fray, M., et al., "Structure-activity relationships of N-substituted piperazine amine reuptake inhibitors" Bioorg Med Chem Lett 16(16):4349-4353 (Aug. 15, 2006).

Gavryushin, A., et al., "Efficient Cross-Coupling of Functionalized Arylzinc Halides Catalyzed by a Nickel Chloride-Diethyl Phosphite System" Org Lett 7(22):4871-4874 (Oct. 7, 2005).

Granchi, C., et al., "A patent review of monoacylglycerol lipase (MAGL) inhibitors" Expert Opin Ther Pat 27(12):1341-1351 (Dec. 1, 2017).

Grill, M., et al., "Members of the endocannabinoid system are distinctly regulated in inflammatory bowel disease and colorectal cancer" Sci Rep 9(2358):1-13 (Feb. 20, 2019).

Haas, D., et al., "Recent Developments in Negishi Cross-Coupling Reactions" ACS Catal 6(3):1540-1552 (Feb. 3, 2016).

He, S., et al., "High-Affinity Small-Molecule Inhibitors of the Menin-Mixed Lineage Leukemia (MLL) Interaction Closely Mimic a Natural Protein-Protein Interaction" J Med Chem 57(4):1543-1556 (Feb. 27, 2014).

Heravi, M., et al., "Buchwald-Hartwig reaction: An overview" J Organometallic Chem 861:17-104 (Apr. 15, 2018).

Hutchings, K., et al., "Synthesis and antibacterial activity of the C-7 side chain of 3-aminoquinazolinediones" Bioorg Med Chem Lett 18(18):5087-5090 (Sep. 15, 2008).

Iannotti, F. A., et al., "Endocannabinoids and endocannabinoid-related mediators: Targets, metabolism and role in neurological disorders" Prog Lipid Res 62:107-128 (Apr. 1, 2016).

Ignatowska-Jankowska, B., et al., "Selective Monoacylglycerol Lipase Inhibitors: Antinociceptive versus Cannabimimetic Effects in Mice" J Pharmacol Exp Ther 353(2):424-432 (May 1, 2015).

"International Preliminary Report on Patentability—PCT/EP2019/081870" (Report Issuance Date: May 25, 2021; Chapter I), :pp. 1-8 (Jun. 3, 2021).

(56) References Cited

OTHER PUBLICATIONS

"International Preliminary Report on Patentability—PCT/EP2019/071520" (Report Issuance Date: Feb. 16, 2021, Chapter I), :pp. 1-8 (Feb. 25, 2021).
"International Preliminary Report on Patentability—PCT/EP2019/050198" (Report Issuance Date: Jul. 14, 2020; Chapter I), :pp. 1-10 (Jul. 23, 2020).
"International Preliminary Report on Patentability—PCT/EP2019/071522" (Report Issuance Date: Feb. 16, 2021, Chapter I), :pp. 1-9 (Feb. 25, 2021).
"International Preliminary Report on Patentability—PCT/EP2019/057174" (Report Issuance Date: Sep. 22, 2020 —Chapter I), :pp. 1-9 (Oct. 1, 2020).
"International Preliminary Report on Patentability—PCT/EP2020/069074" (Report Issuance Date: Jan. 11, 2022; Chapter I), :pp. 1-8 (Jan. 20, 2022).
"International Preliminary Report on Patentability—PCT/EP2020/068320" (Report Issuance Date: Aug. 4, 2021; Chapter II), :pp. 1-34 (Aug. 4, 2021).
"International Preliminary Report on Patentability—PCT/EP2020/059709" (Report Issuance Date: Sep. 28, 2021; Chapter I), :pp. 1-10 (Oct. 21, 2021).
"International Search Report—PCT/EP2019/057174" (w/Written Opinion), :pp. 1-14 (Jul. 3, 2019).
"International Search Report—PCT/EP2019/050198" (w/Written Opinion), :pp. 1-18 (Mar. 1, 2019).
"International Search Report—PCT/EP2019/071520" (w/Written Opinion), :pp. 1-14 (Sep. 17, 2019).
"International Search Report—PCT/EP2019/071522" (w/Written Opinion), :pp. 1-15 (Sep. 17, 2019).
"International Search Report—PCT/EP2019/081870" (w/Written Opinion), :pp. 1-12 (Jan. 14, 2020).
"International Search Report—PCT/EP2020/059709" (w/Written Opinion), :pp. 1-17 (Jun. 8, 2020).
"International Search Report—PCT/EP2020/068320" (w/Written Opinion), :pp. 1-16 (Aug. 13, 2020).
"International Search Report—PCT/EP2020/069074" (w/Written Opinion), :pp. 1-12 (Sep. 16, 2020).
"International Search Report—PCT/EP2020/074897" (w/Written Opinion), :pp. 1-15 (Nov. 18, 2020).
"International Search Report—PCT/EP2020/075260" (w/Written Opinion), :pp. 1-14 (Nov. 18, 2020).
"International Search Report—PCT/EP2020/076228" (w/Written Opinion), :pp. 1-14 (Nov. 12, 2020).
"International Search Report—PCT/EP2020/076346" (w/Written Opinion), :pp. 1-16 (Nov. 13, 2020).
"International Search Report—PCT/EP2020/076347" (w/Written Opinion), :pp. 1-16 (Nov. 30, 2020).
"International Search Report—PCT/EP2021/074150" (w/Written Opinion), :pp. 1-13 (Dec. 8, 2021).
Ishichi, Y., et al., "Novel triple reuptake inhibitors with low risk of CAD associated liabilities: design, synthesis and biological activities of 4-[(1S)-1-(3,4-dichlorophenyl)-2-methoxyethyl] piperidine and related compounds" Bioorg Med Chem 21(15):4600-4613 (Aug. 1, 2013).
Keenan, M., et al., "Design, structure-activity relationship and in vivo efficacy of piperazine analogues of fenarimol as inhibitors of Trypanosoma cruzi" Bioorg Med Chem 21(7):1756-1763 (Apr. 1, 2013).
Kitbunnadaj, R., et al., "Synthesis and structure-activity relationships of conformationally constrained histamine H(3) receptor agonists" J Med Chem 46(25):5445-5457 (Dec. 4, 2003).
Korhonen, J., et al., "Piperazine and piperidine carboxamides and carbamates as inhibitors of fatty acid amide hydrolase (FAAH) and monoacylglycerol lipase (MAGL)" Bioorg Med Chem 22(23):6694-6705 (Dec. 1, 2014).
Liu, F., et al., "Structure-Based Optimization of Pyridoxal 5'-Phosphate-Dependent Transaminase Enzyme (BioA) Inhibitors that Target Biotin Biosynthesis in *Mycobacterium tuberculosis*" J Med Chem 60(13):5507-5520 (Jul. 13, 2017).
Liu, Y. et al., "Discovery of 4-benzoylpiperidine and 3-(piperidin-4-yl)benzo[d]isoxazole derivatives as potential and selective GlyT1 inhibitors" RSC ADV 5(51):40964-40977 (Apr. 30, 2015).
Lleo, A., et al., "Molecular targets of non-steroidal anti-inflammatory drugs in neurodegenerative diseases" Cell Mol Life Sci 64(11):1403-1418 (Apr. 20, 2007).
Long, J.Z., et al., "Selective blockade of 2-arachidonoylglycerol hydrolysis produces cannabinoid behavioral effects" Nat Chem Biol 5(1):37-44 (Jan. 1, 2009).
Marquez, L., et al., "Ulcerative Colitis Induces Changes on the Expression of the Endocannabinoid System in the Human Colonic Tissue" PLOS One 4(9):e6893 (1-13) (Sep. 4, 2009).
Mcallister, L., et al., "Discovery of Trifluoromethyl Glycol Carbamates as Potent and Selective Covalent Monoacylglycerol Lipase (MAGL) Inhibitors for Treatment of Neuroinflammation" J Med Chem 61(7):3008-3026 (Apr. 12, 2018).
Moir, E., et al., "Design, synthesis, and structure-activity relationship study of bicyclic piperazine analogs of indole-3-carboxamides as novel cannabinoid CB1 receptor agonists" Bioorg Med Chem Lett 20(24):7327-7330 (Dec. 15, 2010).
Muccioli, G., et al., "CAY10499, a Novel Monoglyceride Lipase Inhibitor Evidenced by an Expeditious MGL Assay" Chem Bio Chem 9(16):2704-2710 (Nov. 3, 2008).
Mulvihill, M., et al., "Therapeutic Potential of Monoacylglycerol Lipase Inhibitors" Life Sci 92(8-9):492-497 (Nov. 8, 2013).
Negishi, E., "Palladium or Nickel-Catalyzed Cross Coupling. A New Selective Method for Carbon-Carbon Bond Formation" ACC Chem Res 15(11):340-348 (Nov. 1, 1982).
Nomura, D.K., et al., "Endocannabinoid Hydrolysis Generates Brain Prostaglandins That Promote Neuroinflammation" Science 334(6057):809-813 (Nov. 11, 2011).
Nomura, D.K., et al., "Monoacylglycerol Lipase Exerts Dual Control over Endocannabinoid and Fatty Acid Pathways to Support Prostate Cancer" Chem Biol 18(7):846-856 (Jul. 29, 2011).
Nomura, D.K., et al., "Monoacylglycerol Lipase Regulates a Fatty Acid Network that Promotes Cancer Pathogenesis" Cell 140(1):49-61 (Jan. 8, 2010).
Patel, J. et al., "Loratadine analogues as MAGL inhibitors" Bioorg Med Chem Lett 25(7):1436-1442 (Feb. 24, 2015).
Perisetti, A., et al., "Role of cannabis in inflammatory bowel diseases" Ann Gastroenterol 33(2):134-144 (Feb. 12, 2020).
Qin, H., et al., "The role of monoacylglycerol lipase (MAGL) in the cancer progress" Cell Biochem Biophys 70:33-36 (Mar. 16, 2014).
Rafinski, Z et al., "Enantioselective Synthesis of Chromanones Bearing Quaternary Substituted Stereocenters Catalyzed by (1R)-Camphor-Derived N-Heterocyclic Carbenes" J Org Chem 80(15):7468-7476 (Aug. 7, 2015).
Saleh, M.A., et al., "The Synthesis of 2,7 substituted Octahydro-2H-Pyrido[1,2-a] Pyrazines, Analogues of Quinolizidine and Piperazine Drugs" Tetrahedron 50(6):1811-1820 (Jan. 1, 1994).
Scalvini, L., et al., "Monoglyceride lipase: Structure and inhibitors" Chem Phys Lipids 197:13-24 (Jul. 26, 2015).
Senter, T., et al., "Progress towards small molecule menin-mixed lineage leukemia (MLL) interaction inhibitors with in vivo utility" Bioorg Med Chem Lett 25(13):2720-2725 (Jul. 1, 2015).
Surry, D., et al., "Biaryl Phosphane Ligands in Palladium-Catalyzed Amination" Angew Chem Int Ed Engl 47(34):6338-6361 (Aug. 11, 2008).
Ukrorgsyntez, Ltd., CAS Registry Database, 1941372-36-6, (Stereosearch—C20 H27 N3 03), p. 1; Creation Date Jun. 29, 2016.
USPTO, et al., "U.S. Appl. No. 17/569,749, filed Jan. 6, 2022".
USPTO, et al., "U.S. Appl. No. 17/692,632, filed Mar. 11, 2022".
USPTO, et al., "U.S. Appl. No. 17/497,633, filed Oct. 8, 2021".
USPTO, et al., "U.S. Appl. No. 17/700,987, filed Mar. 22, 2022".
Venkatesh, R., et al., "Novel benzothiazine-piperazine derivatives by peptide-coupling as potential anti-proliferative agents" Bioorg Med Chem Lett 27(2):354-359 (Jan. 15, 2017).
Viader, A., et al., "Metabolic Interplay between Astrocytes and Neurons Regulates Endocannabinoid Action" Cell Rep 12(5):798-808 (Aug. 4, 2015).

(56) References Cited

OTHER PUBLICATIONS

Walsh, D., et al., "Synthesis and antiallergy activity of 4-(diarylhydroxymethyl)-1-[3-(aryloxy)propyl]piperidines and structurally related compounds" J Med Chem 32(1):105-118 (Jan. 1, 1989).
Wang, J., et al., "Effect of monoacylglycerol lipase inhibition on intestinal permeability in chronic stress model" Biochem Biophys Res Commun 525(4):962-967 (May 14, 2020).
Wright, K., et al., "Differential expression of cannabinoid receptors in the human colon: cannabinoids promote epithelial wound healing" Gastroenterology 129(2):437-453 (Aug. 1, 2005).
Wu, W., et al., "Synthesis and structure-activity relationships of piperidine-based melanin-concentrating hormone receptor 1 antagonists" Bioorg Med Chem Lett 16(14):3668-3673 (Jul. 15, 2006).
Yin, J., et al., "ARS2/MAGL signaling in glioblastoma stem cells promotes self-renewal and M2-like polarization of tumor-associated macrophages" Nat Commun 11(1):2978(1-15) (Jun. 12, 2020).
Zhang, P., et al., "Silyl Radical Activation of Alkyl Halides in Metallaphotoredox Catalysis: A Unique Pathway for Cross-Electrophile Coupling" J Am Chem Soc 138(26):8084-8087 (Jul. 6, 2016).
Zhang, X., et al., "Direct Aldehyde C—H Arylation and Alkylation via the Combination of Nickel, Hydrogen Atom Transfer, and Photoredox Catalysis" J Am Chem Soc 139(33):11353-11356 (Aug. 23, 2017).
Zhong, P., et al., "Monoacylglycerol Lipase Inhibition Blocks Chronic Stress-Induced Depressive-Like Behaviors via Activation of mTOR Signaling" Neurosychopharmacology 39(7):1763-1776 (Feb. 19, 2014).
Arata, Y., et al., "Studies on 1-Azabicyclo Compounds. XIV. Synthesis of 1-Methyldecahydro-1, 4-diazecin-5-one from Octahydropyrido [1, 2-a] pyrazine Derivatives" Chem & Pharma Bull—JP 21(6):1248-1253 (Jun. 25, 1973).
Belikov, V.G. Pharmaceutical Chemistry—Tutorial "Part I: General Pharmaceutical Chemistry" (Eng. Transl.), Fourth, Revised edition, Moscow-RU:MEDPress-Inform,:27-29 ( 2007).
Brethous, L., et al., "Synthesis and nicotinic receptor activity of chemical space analogues of N-(3R)-1-azabicyclo[2.2.2]oct-3-yl-4-chlorobenzamide (PNU-282,987) and 1,4-diazabicyclo[3.2.2]nonane-4-carboxylic acid 4-bromophenyl ester (SSR180711)" ACS J Med Chem 55(10):4605-4618 (May 24, 2012).
Dyson, G., et al. Chemistry of Synthetic Medicinal Substances (Russian w/ English Translation), Moscow:: 12-19 (Jan. 1, 1964).
Kummerer, K., "Pharmaceuticals in the Environment" Ann Rev Environ Res 35:57-75 (Nov. 1, 2010).
Likhosherstov, A.M., et al., "Synthesis and antiarrhythmic activity of 1, 4-diazabicyclo [4. m.o] alkanyl amides of P-nitro-and P-aminobenzoic acids" Khimiko-Farmatsevticheskii Zhurnal [Russ Pharma Chem J] (Ru language version), 15(8):55-57 (Jan. 26, 1981).
Likhosherstov, A.M., et al., "Synthesis and antiarrhythmic activity of 1, 4-diazabicyclo [4. m.o] alkanyl amides of P-nitro-and P-aminobenzoic acids" Khimiko-Farmatsevticheskii Zhurnal [Russ Pharma Chem J] (English translation), 15(8):55-57 (Jan. 26, 1981).
Mikhlina, E.E., et al., "The properties and some reactions of 4-oxo-1, 5-diazabicyclo [4, 4, 0] decane and 5-oxo-1, 4-diazabicyclo [4, 4, 0] decane" Kimiya Geterotsiklicheskikh Soedinenii ((English translation)), 5(3):547-549 (May 1, 1969).
Mikhlina, E.E., et al., "The properties and some reactions of 4-oxo-1, 5-diazabicyclo [4, 4, 0] decane and 5-oxo-1, 4-diazabicyclo [4, 4, 0] decane" Kimiya Geterotsiklicheskikh Soedinenii ((Ru language version)), 5(3):547-549 (May 1, 1969).

* cited by examiner

HETEROCYCLIC MONOACYLGLYCEROL LIPASE (MAGL) INHIBITORS

CROSS-REFERENCE TO RELATED APPLICATIONS

This application is a continuation of International Application No. PCT/EP2020/068320, filed Jun. 30, 2020, which claims priority to EP Application No. 19184218.6, filed Jul. 3, 2019, the disclosures of which are incorporated herein by reference in their entireties.

FIELD OF THE INVENTION

The present invention relates to organic compounds useful for therapy or prophylaxis in a mammal, and in particular to monoacylglycerol lipase (MAGL) inhibitors for the treatment or prophylaxis of neuroinflammation, neurodegenerative diseases, pain, cancer, mental disorders, multiple sclerosis, Alzheimer's disease, Parkinson's disease, amyotrophic lateral sclerosis, traumatic brain injury, neurotoxicity, stroke, epilepsy, anxiety, migraine and/or depression in a mammal.

BACKGROUND OF THE INVENTION

Endocannabinoids (ECs) are signaling lipids that exert their biological actions by interacting with cannabinoid receptors (CBRs), CB1 and CB2. They modulate multiple physiological processes including neuroinflammation, neurodegeneration and tissue regeneration (Iannotti, F. A., et al., *Progress in lipid research* 2016, 62, 107-28.). In the brain, the main endocannabinoid, 2-arachidonoylglycerol (2-AG), is produced by diacyglycerol lipases (DAGL) and hydrolyzed by the monoacylglycerol lipase, MAGL. MAGL hydrolyses 85% of 2-AG; the remaining 15% being hydrolysed by ABHD6 and ABDH12 (Nomura, D. K., et al., *Science* 2011, 334, 809.). MAGL is expressed throughout the brain and in most brain cell types, including neurons, astrocytes, oligodendrocytes and microglia cells (Chanda, P. K., et al., *Molecular pharmacology* 2010, 78, 996; Viader, A., et al., *Cell reports* 2015, 12, 798.). 2-AG hydrolysis results in the formation of arachidonic acid (AA), the precursor of prostaglandins (PGs) and leukotrienes (LTs). Oxidative metabolism of AA is increased in inflamed tissues. There are two principal enzyme pathways of arachidonic acid oxygenation involved in inflammatory processes, the cyclo-oxygenase which produces PGs and the 5-lipoxygenase which produces LTs. Of the various cyclooxygenase products formed during inflammation, PGE2 is one of the most important. These products have been detected at sites of inflammation, e.g. in the cerebrospinal fluid of patients suffering from neurodegenerative disorders and are believed to contribute to inflammatory response and disease progression. Mice lacking MAGL (Mgll−/−) exhibit dramatically reduced 2-AG hydrolase activity and elevated 2-AG levels in the nervous system while other arachidonoyl-containing phospho- and neutral lipid species including anandamide (AEA), as well as other free fatty acids, are unaltered. Conversely, levels of AA and AA-derived prostaglandins and other eicosanoids, including prostaglandin E2 (PGE2), D2 (PGD2), F2 (PGF2), and thromboxane B2 (TXB2), are strongly decreased. Phospholipase $A_2$ ($PLA_2$) enzymes have been viewed as the principal source of AA, but $cPLA_2$-deficient mice have unaltered AA levels in their brain, reinforcing the key role of MAGL in the brain for AA production and regulation of the brain inflammatory process.

Neuroinflammation is a common pathological change characteristic of diseases of the brain including, but not restricted to, neurodegenerative diseases (e.g. multiple sclerosis, Alzheimer's disease, Parkinson disease, amyotrophic lateral sclerosis, traumatic brain injury, neurotoxicity, stroke, epilepsy and mental disorders such as anxiety and migraine). In the brain, production of eicosanoids and prostaglandins controls the neuroinflammation process. The pro-inflammatory agent lipopolysaccharide (LPS) produces a robust, time-dependent increase in brain eicosanoids that is markedly blunted in Mgll−/− mice. LPS treatment also induces a widespread elevation in pro-inflammatory cytokines including interleukin-1-a (IL-1-a), IL-1b, IL-6, and tumor necrosis factor-a (TNF-a) that is prevented in Mgll−/− mice.

Neuroinflammation is characterized by the activation of the innate immune cells of the central nervous system, the microglia and the astrocytes. It has been reported that anti-inflammatory drugs can suppress in preclinical models the activation of glia cells and the progression of disease including Alzheimer's disease and multiple sclerosis (Lleo A., *Cell Mol Life Sci.* 2007, 64, 1403.). Importantly, genetic and/or pharmacological disruption of MAGL activity also blocks LPS-induced activation of microglial cells in the brain (Nomura, D. K., et al., *Science* 2011, 334, 809.).

In addition, genetic and/or pharmacological disruption of MAGL activity was shown to be protective in several animal models of neurodegeneration including, but not restricted to, Alzheimer's disease, Parkinson's disease and multiple sclerosis. For example, an irreversible MAGL inhibitor has been widely used in preclinical models of neuroinflammation and neurodegeneration (Long, J. Z., et al., *Nature chemical biology* 2009, 5, 37.). Systemic injection of such inhibitor recapitulates the Mgll−/− mice phenotype in the brain, including an increase in 2-AG levels, a reduction in AA levels and related eicosanoids production, as well as the prevention of cytokines production and microglia activation following LPS-induced neuroinflammation (Nomura, D. K., et al., *Science* 2011, 334, 809.), altogether confirming that MAGL is a druggable target.

Consecutive to the genetic and/or pharmacological disruption of MAGL activity, the endogenous levels of the MAGL natural substrate in the brain, 2-AG, are increased. 2-AG has been reported to show beneficial effects on pain with, for example, anti-nociceptive effects in mice (Ignatowska-Jankowska B. et al., *J. Pharmacol. Exp. Ther.* 2015, 353, 424.) and on mental disorders, such as depression in chronic stress models (Zhong P. et al., *Neuropsychopharmacology* 2014, 39, 1763.).

Furthermore, oligodendrocytes (OLs), the myelinating cells of the central nervous system, and their precursors (OPCs) express the cannabinoid receptor 2 (CB2) on their membrane. 2-AG is the endogenous ligand of CB1 and CB2 receptors. It has been reported that both cannabinoids and pharmacological inhibition of MAGL attenuate OLs's and OPCs's vulnerability to excitotoxic insults and therefore may be neuroprotective (Bernal-Chico, A., et al., *Glia* 2015, 63, 163.). Additionally, pharmacological inhibition of MAGL increases the number of myelinating OLs in the brain of mice, suggesting that MAGL inhibition may promote differentiation of OPCs in myelinating OLs in vivo (Alpar, A., et al., *Nature communications* 2014, 5, 4421.). Inhibition of MAGL was also shown to promote remyelination and functional recovery in a mouse model of progressive multiple sclerosis (Feliu A. et al., *Journal of Neuroscience* 2017, 37 (35), 8385.).

Finally, in recent years, metabolism is talked highly important in cancer research, especially the lipid metabolism. Researchers believe that the de novo fatty acid synthesis plays an important role in tumor development. Many studies illustrated that endocannabinoids have anti-tumorigenic actions, including anti-proliferation, apoptosis induction and anti-metastatic effects. MAGL as an important decomposing enzyme for both lipid metabolism and the endocannabinoids system, additionally as a part of a gene expression signature, contributes to different aspects of tumourigenesis (Qin, H., et al., *Cell Biochem. Biophys.* 2014, 70, 33; Nomura D K et al., *Cell* 2009, 140(1), 49-61; Nomura D K et al., *Chem. Biol.* 2011, 18(7), 846-856).

In conclusion, suppressing the action and/or the activation of MAGL is a promising new therapeutic strategy for the treatment or prevention of neuroinflammation, neurodegenerative diseases, pain, cancer and mental disorders. Furthermore, suppressing the action and/or the activation of MAGL is a promising new therapeutic strategy for providing neuroprotection and myelin regeneration. Accordingly, there is a high unmet medical need for new MAGL inhibitors.

SUMMARY OF THE INVENTION

In a first aspect, the present invention provides compounds of Formula (I), or pharmaceutically acceptable salts thereof, (I)

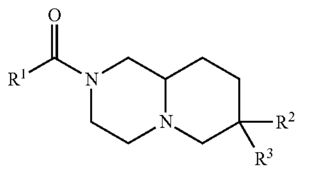

wherein $R^1$ to $R^3$ are as defined herein.

In a further aspect, the present invention provides a process of manufacturing the compounds of formula (I) as described herein, comprising:

(a) reacting an amine 12 or 14, wherein $R^2$ is as defined herein and $R^3$ is hydroxy (12) or hydrogen (14)

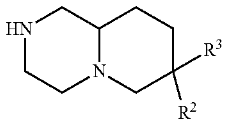

12, $R^3$ = OH
14, $R^3$ = H with a carboxylic acid 15, wherein $R^1$ is as defined herein

15

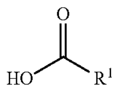

in the presence of a coupling reagent, such as HATU, DCC, EDCI, HOBt, TBTU or $T_3P$, and a base, such as Huenig's base, triethyl amine or DMAP, to afford said compound of formula (I) wherein $R^3$ is hydroxy or hydrogen; and optionally, provided $R^3$ is hydroxy;

(b) alkylating the alcohol $R^3$ by treating it with an appropriate base, such as NaH, KH, NaHMDS, LiHMDS or LDA, preferably with NaH, followed by addition of an electrophile, e.g. an alkyl- or cycloalkyl halide, such as MeI, EtI, iPrI or CyPrI to yield the corresponding compound of formula (I), wherein $R^3$ is alkoxy or cycloalkyloxy; or (c) transforming the alcohol $R^3$ into a halogen by reacting the compound of formula (I) wherein $R^3$ is hydroxy with (i) an acid, e.g. HCl, HBr, HI, $POCl_3$, $SOCl_2$ or $PBr_3$; or (ii) with a suitable amino sulfurane reagent such as DAST; or (iii) a sulfonylating reagent such as mesyl chloride, followed by reacting the intermediate sulfonate ester with a halogenide, e.g. NaF to yield the corresponding compound of formula (I), wherein $R^3$ is halogen.

In a further aspect, the present invention provides a compound of formula (I) as described herein, when manufactured according to the processes described herein.

In a further aspect, the present invention provides a compound of formula (I) as described herein, or a pharmaceutically acceptable salt thereof, for use as therapeutically active substance.

In a further aspect, the present invention provides a pharmaceutical composition comprising a compound of formula (I) as described herein, or a pharmaceutically acceptable salt thereof, and a therapeutically inert carrier.

In a further aspect, the present invention provides the use of a compound of formula (I) as described herein, or of a pharmaceutically acceptable salt thereof, for inhibiting monoacylglycerol lipase (MAGL) in a mammal.

In a further aspect, the present invention provides the use of a compound of formula (I) as described herein, or of a pharmaceutically acceptable salt thereof, for the treatment or prophylaxis of neuroinflammation, neurodegenerative diseases, pain, cancer and/or mental disorders in a mammal.

In a further aspect, the present invention provides the use of a compound of formula (I) as described herein, or of a pharmaceutically acceptable salt thereof, for the treatment or prophylaxis of multiple sclerosis, Alzheimer's disease, Parkinson's disease, amyotrophic lateral sclerosis, traumatic brain injury, neurotoxicity, stroke, epilepsy, anxiety, migraine, depression, hepatocellular carcinoma, colon carcinogenesis, ovarian cancer, neuropathic pain, chemotherapy induced neuropathy, acute pain, chronic pain and/or spasticity associated with pain in a mammal.

In a further aspect, the present invention provides a compound of formula (I) as described herein, or a pharmaceutically acceptable salt thereof, for use in a method of inhibiting monoacylglycerol lipase in a mammal.

In a further aspect, the present invention provides a compound of formula (I) as described herein, or a pharmaceutically acceptable salt thereof, for use in the treatment or prophylaxis of neuroinflammation, neurodegenerative diseases, pain, cancer and/or mental disorders in a mammal.

In a further aspect, the present invention provides a compound of formula (I) as described herein, or a pharmaceutically acceptable salt thereof, for use in the treatment or prophylaxis of multiple sclerosis, Alzheimer's disease, Parkinson's disease, amyotrophic lateral sclerosis, traumatic brain injury, neurotoxicity, stroke, epilepsy, anxiety, migraine, depression, hepatocellular carcinoma, colon carcinogenesis, ovarian cancer, neuropathic pain, chemotherapy induced neuropathy, acute pain, chronic pain and/or spasticity associated with pain in a mammal.

In a further aspect, the present invention provides the use of a compound of formula (I) as described herein, or of a pharmaceutically acceptable salt thereof, for the preparation of a medicament for inhibiting monoacylglycerol lipase in a mammal.

In a further aspect, the present invention provides the use of a compound of formula (I) as described herein, or of a pharmaceutically acceptable salt thereof, for the preparation of a medicament for the treatment or prophylaxis of neuroinflammation, neurodegenerative diseases, pain, cancer and/or mental disorders in a mammal.

In a further aspect, the present invention provides the use of a compound of formula (I) as described herein, or of a pharmaceutically acceptable salt thereof, for the preparation of a medicament for the treatment or prophylaxis of multiple sclerosis, Alzheimer's disease, Parkinson's disease, amyotrophic lateral sclerosis, traumatic brain injury, neurotoxicity, stroke, epilepsy, anxiety, migraine, depression, hepatocellular carcinoma, colon carcinogenesis, ovarian cancer, neuropathic pain, chemotherapy induced neuropathy, acute pain, chronic pain and/or spasticity associated with pain in a mammal.

In a further aspect, the present invention provides a method for inhibiting monoacylglycerol lipase in a mammal, which method comprises administering an effective amount of a compound of formula (I) as described herein, or a pharmaceutically acceptable salt thereof, to the mammal.

In a further aspect, the present invention provides a method for the treatment or prophylaxis of neuroinflammation, neurodegenerative diseases, pain, cancer and/or mental disorders in a mammal, which method comprises administering an effective amount of a compound of formula (I) as described herein, or a pharmaceutically acceptable salt thereof, to the mammal.

In a further aspect, the present invention provides a method for the treatment or prophylaxis of multiple sclerosis, Alzheimer's disease, Parkinson's disease, amyotrophic lateral sclerosis, traumatic brain injury, neurotoxicity, stroke, epilepsy, anxiety, migraine, depression, hepatocellular carcinoma, colon carcinogenesis, ovarian cancer, neuropathic pain, chemotherapy induced neuropathy, acute pain, chronic pain and/or spasticity associated with pain in a mammal, which method comprises administering an effective amount of a compound of formula (I) as described herein, or a pharmaceutically acceptable salt thereof, to the mammal.

DETAILED DESCRIPTION OF THE INVENTION

Definitions

Features, integers, characteristics, compounds, chemical moieties or groups described in conjunction with a particular aspect, embodiment or example of the invention are to be understood to be applicable to any other aspect, embodiment or example described herein, unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The term "alkyl" refers to a mono- or multivalent, e.g., a mono- or bivalent, linear or branched saturated hydrocarbon group of 1 to 6 carbon atoms ("$C_1$-$C_6$-alkyl"), e.g., 1, 2, 3, 4, 5, or 6 carbon atoms. In some embodiments, the alkyl group contains 1 to 3 carbon atoms, e.g., 1, 2 or 3 carbon atoms. Some non-limiting examples of alkyl include methyl, ethyl, propyl, 2-propyl (isopropyl), n-butyl, iso-butyl, sec-butyl, tert-butyl, and 2,2-dimethylpropyl. A particularly preferred, yet non-limiting example of alkyl is methyl.

The term "alkoxy" refers to an alkyl group, as previously defined, attached to the parent molecular moiety via an oxygen atom. In some preferred embodiments, the alkoxy group contains 1 to 6 carbon atoms ("$C_{1-6}$-alkoxy"), e.g. 1, 2, 3, 4, 5, or 6 carbon atoms. In other embodiments, the alkoxy group contains 1 to 4 carbon atoms. In still other embodiments, the alkoxy group contains 1 to 3 carbon atoms. Some non-limiting examples of alkoxy groups include methoxy, ethoxy, n-propoxy, isopropoxy, n-butoxy, isobutoxy, 1,1-dimethylpropoxy, 2,2-dimethylpropoxy, and tert-butoxy. A particularly preferred, yet non-limiting example of alkoxy is methoxy.

The term "halogen" or "halo" refers to fluoro (F), chloro (Cl), bromo (Br), or iodo (I). Preferably, the term "halogen" or "halo" refers to fluoro (F), chloro (Cl) or bromo (Br). Particularly preferred, yet non-limiting examples of "halogen" or "halo" are fluoro (F) and chloro (Cl).

The term "cycloalkyl" as used herein refers to a saturated or partly unsaturated monocyclic or bicyclic hydrocarbon group of 3 to 14 ring carbon atoms ("$C_{3-12}$-cycloalkyl"), preferably 3-12 ring carbon atoms, more preferably 3-10 ring carbon atoms, yet more preferably 3-8 ring carbon atoms, most preferably 3-6 ring carbon atoms. In some preferred embodiments, the cycloalkyl group is a saturated monocyclic hydrocarbon group of 3 to 8 ring carbon atoms. "Bicyclic cycloalkyl" refers to cycloalkyl moieties consisting of two saturated carbocycles having two carbon atoms in common, i.e., the bridge separating the two rings is either a single bond or a chain of one or two ring atoms, and to spirocyclic moieties, i.e., the two rings are connected via one common ring atom. In one embodiment, the cycloalkyl group is a saturated monocyclic hydrocarbon group of 3 to 6 ring carbon atoms, e.g., of 3, 4, 5 or 6 carbon atoms. Some non-limiting examples of cycloalkyl include cyclopropyl, cyclobutyl, cyclopentyl, cyclohexyl, cycloheptyl, and 1-bicyclo[1.1.1]pentanyl.

The term "heterocyclyl" as used herein refers to a saturated or partly unsaturated mono- or bicyclic, preferably monocyclic ring system of 3 to 14 ring atoms ("$C_2$-$C_{13}$-heterocyclyl"), preferably 5 to 14 ring atoms, more preferably 3 to 8 ring atoms, wherein 1, 2, or 3 of said ring atoms are heteroatoms selected from N, O and S, the remaining ring atoms being carbon. Preferably, 1 to 2 of said ring atoms are selected from N and O, the remaining ring atoms being carbon. "Bicyclic heterocyclyl" refers to heterocyclic moieties consisting of two cycles having two ring atoms in common, i.e., the bridge separating the two rings is either a single bond or a chain of one or two ring atoms, and to spirocyclic moieties, i.e., the two rings are connected via one common ring atom. Some non-limiting examples of monocyclic heterocyclyl groups include 1,2-dihydropyridin-5-yl, azetidin-3-yl, azetidin-2-yl, 2-azaspiro[3.3]heptan-2-yl, 2,6-diazaspiro[3.3]heptan-2-yl, 2-azaspiro[3.4]octan-2-yl, 5-oxa-2-azaspiro[3.4]octan-2-yl, pyrrolidinyl (e.g. pyrrolidin-1-yl), thiomorpholino, oxetan-3-yl, oxetan-2-yl, tetrahydrofuranyl (e.g. tetrahydrofuran-2-yl), tetrahydropyranyl (e.g. tetrahydropyran-2-yl), 1-piperidinyl, 2-piperidinyl, 3-piperidinyl, 4-piperidinyl, piperazinyl (e.g. piperazin-1-yl), morpholino, morpholin-2-yl and morpholin-3-yl.

The term "aryl" refers to a monocyclic, bicyclic, or tricyclic carbocyclic ring system having a total of 6 to 14 ring members ("$C_{6-14}$-aryl"), preferably, 6 to 12 ring members, and more preferably 6 to 10 ring members, and wherein at least one ring in the system is aromatic. A preferred, yet non-limiting example of aryl includes phenyl.

The term "heteroaryl" refers to a mono- or multivalent, monocyclic, bicyclic or tricyclic, preferably bicyclic ring system having a total of 5 to 14 ring members ("$C_{1-13}$-heteroaryl"), preferably, 5 to 12 ring members, more preferably 5 to 10 ring members, most preferably 5 to 6 ring members, wherein at least one ring in the system is aromatic, and at least one ring in the system contains one or more heteroatoms. Preferably, "heteroaryl" refers to a 5-10 membered heteroaryl comprising 1, 2, 3 or 4 heteroatoms independently selected from O, S and N. Most preferably, "heteroaryl" refers to a 5-10 membered heteroaryl comprising 1 to 2 heteroatoms independently selected from O and N. Some non-limiting examples of heteroaryl include pyridazinyl (e.g., pyridazin-4-yl), 2-pyridyl, 3-pyridyl, 4-pyridyl, pyrimidin-2-yl, pyrimidin-4-yl, pyrimidin-5-yl, pyrimidin-6-yl, 1,3-benzoxazol-2-yl, 1,3-benzoxazol-4-yl, 1,3-benzoxazol-5-yl, 1,3-benzoxazol-6-yl, 1,3-benzoxazol-7-yl, 1H-indazol-3-yl, 1H-indazol-4-yl, oxadiazolyl (e.g. 1,2,4-oxadiazol-3-yl, 1,3,4-oxadiazol-2-yl), pyrazolyl (e.g. 1H-pyrazol-4-yl), triazolyl (e.g. 1H-1,2,4-triazol-3-yl, 1H-triazol-4-yl, 2H-triazol-4-yl), and tetrazolyl (e.g. 2H-tetrazol-5-yl).

The term "cycloalkyloxy" refers to a cycloalkyl group as previously defined, attached to the parent molecular moiety via an oxygen atom.

The term "hydroxy" refers to an —OH group.

The term "amino" refers to an —$NH_2$ group.

The term "oxo" refers to a double bonded oxygen (=O).

The term "alkoxycarbonyl" refers to a group alkyl-O—C(O)— (commonly referred to as "carboxylic acid ester"), wherein alkyl is as defined herein.

The term "carboxy" refers to a group —C(O)OH (commonly referred to as "carboxylic acid").

The term "alkenyl" denotes a mono- or bivalent linear or branched hydrocarbon group of 2 to 6 carbon atoms comprising at least one C—C double bond ("$C_2$-$C_6$-alkenyl"), e.g. 1 or 2 C—C double bonds. In particular embodiments, alkenyl has 2 to 4 carbon atoms with at least one C—C double bond, e.g. 1 or 2 C—C double bonds. Examples of alkenyl include ethenyl, propenyl, prop-2-enyl, isopropenyl, n-butenyl (e.g. (Z)-but-1-enyl), iso-butenyl, allyl, 2-methyl-allyl, 2-methylprop-1-enyl, and propa-1,2-dienyl.

The term "hydroxycycloalkyl" refers to a cycloalkyl group as defined herein, wherein at least one of the hydrogen atoms of the cycloalkyl group has been replaced by a hydroxy group. Preferably, "hydroxycycloalkyl" refers to a cycloalkyl group wherein 1, 2 or 3 hydrogen atoms, most preferably 1 hydrogen atom of the alkyl group have been replaced by a hydroxy group. A preferred, yet non-limiting example of a hydroxycycloalkyl group is hydroxycyclopropyl (e.g., 1-hydroxycyclopropyl).

The term "pharmaceutically acceptable salt" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, in particular hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition, these salts may be prepared by addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyimine resins and the like. Particular pharmaceutically acceptable salts of compounds of formula (I) are hydrochloride salts.

The term "protective group" (PG) denotes the group which selectively blocks a reactive site in a multifunctional compound such that a chemical reaction can be carried out selectively at another unprotected reactive site in the meaning conventionally associated with it in synthetic chemistry. Protective groups can be removed at the appropriate point. Exemplary protective groups are amino-protective groups, carboxy-protective groups or hydroxy-protective groups. Particular protective groups are the tert-butoxycarbonyl (Boc), benzyloxycarbonyl (Cbz), fluorenylmethoxycarbonyl (Fmoc) and benzyl (Bn). Further particular protective groups are the tert-butoxycarbonyl (Boc) and the fluorenylmethoxycarbonyl (Fmoc). More particular protective group is the tert-butoxycarbonyl (Boc). Exemplary protective groups and their application in organic synthesis are described, for example, in "Protective Groups in Organic Chemistry" by T. W. Greene and P. G. M. Wutts, 5th Ed., 2014, John Wiley & Sons, N.Y.

The compounds of formula (I) can contain several asymmetric centers and can be present in the form of optically pure enantiomers, mixtures of enantiomers such as, for example, racemates, optically pure diastereioisomers, mixtures of diastereoisomers, diastereoisomeric racemates or mixtures of diastereoisomeric racemates.

According to the Cahn-Ingold-Prelog Convention, the asymmetric carbon atom can be of the "R" or "S" configuration.

The abbreviation "MAGL" refers to the enzyme monoacylglycerol lipase. The terms "MAGL" and "monoacylglycerol lipase" are used herein interchangeably.

The term "treatment" as used herein includes: (1) inhibiting the state, disorder or condition (e.g. arresting, reducing or delaying the development of the disease, or a relapse thereof in case of maintenance treatment, of at least one clinical or subclinical symptom thereof); and/or (2) relieving the condition (i.e., causing regression of the state, disorder or condition or at least one of its clinical or subclinical symptoms). The benefit to a patient to be treated is either statistically significant or at least perceptible to the patient or to the physician. However, it will be appreciated that when a medicament is administered to a patient to treat a disease, the outcome may not always be effective treatment.

The term "prophylaxis" as used herein includes: preventing or delaying the appearance of clinical symptoms of the state, disorder or condition developing in a mammal and especially a human that may be afflicted with or predisposed to the state, disorder or condition but does not yet experience or display clinical or subclinical symptoms of the state, disorder or condition.

The term "neuroinflammation" as used herein relates to acute and chronic inflammation of the nervous tissue, which is the main tissue component of the two parts of the nervous system; the brain and spinal cord of the central nervous system (CNS), and the branching peripheral nerves of the peripheral nervous system (PNS). Chronic neuroinflammation is associated with neurodegenerative diseases such as Alzheimer's disease, Parkinson's disease and multiple sclerosis. Acute neuroinflammation usually follows injury to the central nervous system immediately, e.g., as a result of traumatic brain injury (TBI).

The term "traumatic brain injury" ("TBI", also known as "intracranial injury"), relates to damage to the brain resulting from external mechanical force, such as rapid acceleration or deceleration, impact, blast waves, or penetration by a projectile.

The term "neurodegenerative diseases" relates to diseases that are related to the progressive loss of structure or function of neurons, including death of neurons. Examples of neurodegenerative diseases include, but are not limited to, multiple sclerosis, Alzheimer's disease, Parkinson's disease and amyotrophic lateral sclerosis.

The term "mental disorders" (also called mental illnesses or psychiatric disorders) relates to behavioral or mental patterns that may cause suffering or a poor ability to function in life. Such features may be persistent, relapsing and remitting, or occur as a single episode. Examples of mental disorders include, but are not limited to, anxiety and depression.

The term "pain" relates to an unpleasant sensory and emotional experience associated with actual or potential tissue damage. Examples of pain include, but are not limited to, nociceptive pain, chronic pain (including idiopathic pain), neuropathic pain including chemotherapy induced neuropathy, phantom pain and phsychogenic pain. A particular example of pain is neuropathic pain, which is caused by damage or disease affecting any part of the nervous system involved in bodily feelings (i.e., the somatosensory system). In one embodiment, "pain" is neuropathic pain resulting from amputation or thoracotomy. In one embodiment, "pain" is chemotherapy induced neuropathy.

The term "neurotoxicity" relates to toxicity in the nervous system. It occurs when exposure to natural or artificial toxic substances (neurotoxins) alter the normal activity of the nervous system in such a way as to cause damage to nervous tissue. Examples of neurotoxicity include, but are not limited to, neurotoxicity resulting from exposure to substances used in chemotherapy, radiation treatment, drug therapies, drug abuse, and organ transplants, as well as exposure to heavy metals, certain foods and food additives, pesticides, industrial and/or cleaning solvents, cosmetics, and some naturally occurring substances.

The term "cancer" refers to a disease characterized by the presence of a neoplasm or tumor resulting from abnormal uncontrolled growth of cells (such cells being "cancer cells"). As used herein, the term cancer explicitly includes, but is not limited to, hepatocellular carcinoma, colon carcinogenesis and ovarian cancer.

The term "mammal" as used herein includes both humans and non-humans and includes but is not limited to humans, non-human primates, canines, felines, murines, bovines, equines, and porcines. In a particularly preferred embodiment, the term "mammal" refers to humans.

Compounds of the Invention

In a first aspect (A1), the present invention provides compounds of Formula (I)

(I)

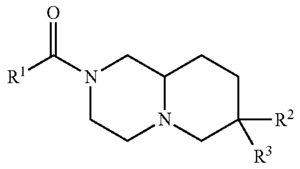

or pharmaceutically acceptable salts thereof, wherein:

$R^1$ is selected from the group consisting of (i) $C_6$-$C_{14}$-aryl optionally substituted with 1-2 substituents independently selected from the group consisting of $C_{1-6}$-alkoxy, halogen, and a group

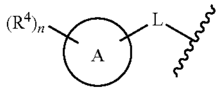

;

(ii) 5- to 6-membered heteroaryl optionally substituted with 1-2 substituents independently selected from the group consisting of halogen, hydroxy, $C_{1-6}$-alkoxy, —$B(OH)_2$, 5- to 6-membered heteroaryl, $C_{1-6}$-alkyl, and amino; and (iii) 5- to 14-membered heterocyclyl optionally substituted with 1-3 substituents independently selected from the group consisting of halogen, $C_{1-6}$-alkyl, and oxo;

$R^2$ is selected from the group consisting of (i) $C_{1-6}$-alkyl optionally substituted with 1-3 substituents independently selected from halogen;

(ii) $C_{3-14}$-cycloalkyl;

(iii) $C_6$-$C_{14}$-aryl optionally substituted with 1-2 substituents independently selected from halogen;

(iv) 5- to 14-membered heteroaryl optionally substituted with 1-3 substituents independently selected from halogen, $C_{1-6}$-alkyl, halo-$C_{1-6}$-alkyl, and oxo; and (v) 5- to 14-membered heteroaryloxy optionally substituted with 1-3 substituents independently selected from halogen, $C_{1-6}$-alkyl, halo-$C_{1-6}$-alkyl, and oxo; and (vi) 5- to 14-membered heterocyclyl optionally substituted with 1-3 substituents independently selected from halogen, $C_{1-6}$-alkyl, halo-$C_{1-6}$-alkyl, and oxo;

$R^3$ is selected from the group consisting of hydrogen, halogen, $C_{1-6}$-alkoxy, $C_{3-14}$-cycloalkyloxy, and hydroxy;

$R^4$ is selected from the group consisting of hydrogen, halogen, $C_{1-6}$-alkyl, hydroxy-$C_{1-6}$-alkyl, $C_{1-6}$-alkoxycarbonyl, $C_{1-6}$-alkoxycarbonyl-NH—, hydroxy, amino, carboxy, $C_{1-6}$-alkyl-C(O)—NH—, $C_{2-6}$-alkenyl-C(O)—NH—, carboxy-NH—, oxo, $C_{3-14}$-cycloalkyl, and hydroxy-$C_{3-14}$-cycloalkyl;

L is selected from the group consisting of a covalent bond and —CH═CH—;

A is selected from the group consisting of $C_6$-$C_{14}$-aryl, 5- to 14-membered heteroaryl, and 5- to 14-membered heterocyclyl; and n is 1, 2, 3, or 4.

The invention further provides the following enumerated embodiments (E) according to the first Aspect A1:

E1 The compound of formula (I) according to A1, or a pharmaceutically acceptable salt thereof, wherein:

$R^1$ is selected from the group consisting of (i) $C_6$-$C_{14}$-aryl optionally substituted with 1-2 substituents independently selected from the group consisting of $C_{1-6}$-alkoxy, halogen, and a group

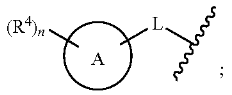

(ii) 5- to 6-membered heteroaryl optionally substituted with 1-2 substituents independently selected from the group consisting of halogen, $C_{1-6}$-alkoxy, $C_{1-6}$-alkyl, and amino; and (iii) 5- to 14-membered heterocyclyl optionally substituted with 1-3 substituents independently selected from the group consisting of halogen, $C_{1-6}$-alkyl, and oxo;

$R^2$ is selected from the group consisting of (i) $C_{1-6}$-alkyl optionally substituted with 1-3 substituents independently selected from halogen;

(ii) $C_{3-14}$-cycloalkyl;

(iii) $C_6$-$C_{14}$-aryl optionally substituted with 1-2 substituents independently selected from halogen;

(iv) 5- to 14-membered heteroaryl optionally substituted with 1-3 substituents independently selected from halogen, $C_{1-6}$-alkyl, halo-$C_{1-6}$-alkyl, and oxo; and (v) 5- to 14-membered heterocyclyl optionally substituted with 1-3 substituents independently selected from halogen, $C_{1-6}$-alkyl, halo-$C_{1-6}$-alkyl, and oxo;

$R^3$ is selected from the group consisting of hydrogen, halogen, $C_{1-6}$-alkoxy, $C_{3-14}$-cycloalkyloxy, and hydroxy;

$R^4$ is selected from the group consisting of hydrogen, halogen, $C_{1-6}$-alkyl, $C_{1-6}$-alkoxycarbonyl, $C_{1-6}$-alkoxycarbonyl-NH—, hydroxy, amino, carboxy, $C_{1-6}$-alkyl-C(O)—NH—, $C_{2-6}$-alkenyl-C(O)—NH—, carboxy-NH—, oxo, $C_{3-14}$-cycloalkyl, and hydroxy-$C_{3-14}$-cycloalkyl;

L is selected from the group consisting of a covalent bond and —CH═CH—;

A is selected from the group consisting of $C_6$-$C_{14}$-aryl, 5- to 14-membered heteroaryl, and 5- to 14-membered heterocyclyl; and n is 1, 2, 3, or 4.

E2 The compound of formula (I) according to A1 or E1, or a pharmaceutically acceptable salt thereof, with the proviso that the compound of formula (I) is not (4-fluorophenyl)-[7-(4-fluorophenyl)-1,3,4,6,7,8,9,9a-octahydropyrido[1,2-a]pyrazin-2-yl]methanone.

E3 The compound of formula (I) according to A1 or E1, or a pharmaceutically acceptable salt thereof with the proviso that the compound of formula (I) is not selected from the group consisting of:

(4-fluorophenyl)-[7-(4-fluorophenyl)-1,3,4,6,7,8,9,9a-octahydropyrido[1,2-a]pyrazin-2-yl]methanone;

[(7R,9aR)-7-(4-chlorophenyl)-1,3,4,6,7,8,9,9a-octahydropyrido[1,2-a]pyrazin-2-yl]-(2-bromo-3-methoxyphenyl)methanone;

[(7R,9aR)-7-(4-chlorophenyl)-1,3,4,6,7,8,9,9a-octahydropyrido[1,2-a]pyrazin-2-yl]-(2-bromo-3-methoxyphenyl)methanone;hydrochloride;

[(7R,9aR)-7-phenyl-1,3,4,6,7,8,9,9a-octahydropyrido[1,2-a]pyrazin-2-yl]-(2-bromo-3-methoxyphenyl)methanone;

[(7R,9aR)-7-(4-chlorophenyl)-1,3,4,6,7,8,9,9a-octahydropyrido[1,2-a]pyrazin-2-yl]-(2-chloro-3-methoxyphenyl)methanone;

[(7R,9aR)-7-(4-chlorophenyl)-1,3,4,6,7,8,9,9a-octahydropyrido[1,2-a]pyrazin-2-yl]-(2-methoxyphenyl)methanone;

[(7R,9aR)-7-(4-chlorophenyl)-1,3,4,6,7,8,9,9a-octahydropyrido[1,2-a]pyrazin-2-yl]-(2-chloro-6-fluorophenyl)methanone;

[(7R,9aR)-7-(4-chlorophenyl)-1,3,4,6,7,8,9,9a-octahydropyrido[1,2-a]pyrazin-2-yl]-(2-chlorophenyl)methanone;

[(7R,9aR)-7-(4-chlorophenyl)-1,3,4,6,7,8,9,9a-octahydropyrido[1,2-a]pyrazin-2-yl]-(4-chloro-6-methylpyridin-3-yl)methanone;

[(7R,9aR)-7-phenyl-1,3,4,6,7,8,9,9a-octahydropyrido[1,2-a]pyrazin-2-yl]-(2-chloro-3-propan-2-yloxyphenyl)methanone;hydrochloride;

[(7R,9aR)-7-phenyl-1,3,4,6,7,8,9,9a-octahydropyrido[1,2-a]pyrazin-2-yl]-(4-chloro-1-methylpyrrolo[2,3-b]pyridin-5-yl)methanone;

[(7R,9aR)-7-phenyl-1,3,4,6,7,8,9,9a-octahydropyrido[1,2-a]pyrazin-2-yl]-(4-chloro-1-propan-2-ylpyrrolo[2,3-b]pyridin-5-yl)methanone;

[(7S,9aS)-7-(4-chlorophenyl)-1,3,4,6,7,8,9,9a-octahydropyrido[1,2-a]pyrazin-2-yl]-(2-bromo-3-methoxyphenyl)methanone;

[(7R,9aR)-7-phenyl-1,3,4,6,7,8,9,9a-octahydropyrido[1,2-a]pyrazin-2-yl]-(3-chloro-2-methoxypyridin-4-yl)methanone;

[(7R,9aR)-7-(4-chlorophenyl)-1,3,4,6,7,8,9,9a-octahydropyrido[1,2-a]pyrazin-2-yl]-(4-chloro-1-methylpyrrolo[2,3-b]pyridin-5-yl)methanone;

[(7R,9aR)-7-(4-chlorophenyl)-1,3,4,6,7,8,9,9a-octahydropyrido[1,2-a]pyrazin-2-yl]-(4-chloro-1-methylpyrazolo[3,4-b]pyridin-5-yl)methanone;

[(7R,9aR)-7-(3,4-dichlorophenyl)-1,3,4,6,7,8,9,9a-octahydropyrido[1,2-a]pyrazin-2-yl]-(2-bromo-3-methoxyphenyl)methanone;

[(7S,9aS)-7-(3,4-dichlorophenyl)-1,3,4,6,7,8,9,9a-octahydropyrido[1,2-a]pyrazin-2-yl]-(2-bromo-3-methoxyphenyl)methanone;

[(7R,9aR)-7-(3-chloro-4-fluorophenyl)-1,3,4,6,7,8,9,9a-octahydropyrido[1,2-a]pyrazin-2-yl]-(2-chloro-3-methoxyphenyl)methanone;

[(7S,9aS)-7-(3-chloro-4-fluorophenyl)-1,3,4,6,7,8,9,9a-octahydropyrido[1,2-a]pyrazin-2-yl]-(2-chloro-3-methoxyphenyl)methanone;

[(7R,9aR)-7-(4-chlorophenyl)-1,3,4,6,7,8,9,9a-octahydropyrido[1,2-a]pyrazin-2-yl]-(4-chloro-5-methoxypyridin-3-yl)methanone;

(4-chloro-3-methyl-[1,2]oxazolo[5,4-b]pyridin-5-yl)-[rac-(7R,9aR)-7-(3-chloro-4-fluorophenyl)-1,3,4,6,7,8,9,9a-octahydropyrido[1,2-a]pyrazin-2-yl]methanone;

[(7R,9aR)-7-(3-chloro-4-fluorophenyl)-1,3,4,6,7,8,9,9a-octahydropyrido[1,2-a]pyrazin-2-yl]-(4-chloro-3-methyl-[1,2]oxazolo[5,4-b]pyridin-5-yl)methanone;

[(7S,9aS)-7-(3-chloro-4-fluorophenyl)-1,3,4,6,7,8,9,9a-octahydropyrido[1,2-a]pyrazin-2-yl]-(4-chloro-3-methyl-[1,2]oxazolo[5,4-b]pyridin-5-yl)methanone;

(4-chloro-3-methyl-1H-indazol-5-yl)-[rac-(7R,9aR)-7-(3-chloro-4-fluorophenyl)-1,3,4,6,7,8,9,9a-octahydropyrido[1,2-a]pyrazin-2-yl]methanone;

(4-chloro-[1,2]thiazolo[5,4-b]pyridin-5-yl)-[rac-(7R,9aR)-7-(3-chloro-4-fluorophenyl)-1,3,4,6,7,8,9,9a-octahydropyrido[1,2-a]pyrazin-2-yl]methanone;

(4-chloro-3-methyl-1H-indazol-5-yl)-[rac-(7R,9aR)-7-(4-chlorophenyl)-7-hydroxy-3,4,6,8,9,9a-hexahydro-1H-pyrido[1,2-a]pyrazin-2-yl]methanone;

(4-chloro-3-methyl-1H-indazol-5-yl)-[rac-(7R,9aS)-7-(4-chlorophenyl)-7-hydroxy-3,4,6,8,9,9a-hexahydro-1H-pyrido[1,2-a]pyrazin-2-yl]methanone;

[(7S,9aR)-7-(4-chlorophenyl)-7-hydroxy-3,4,6,8,9,9a-hexahydro-1H-pyrido[1,2-a]pyrazin-2-yl]-(4-chloro-3-methyl-1H-indazol-5-yl)methanone;

[(7R,9aS)-7-(4-chlorophenyl)-7-hydroxy-3,4,6,8,9,9a-hexahydro-1H-pyrido[1,2-a]pyrazin-2-yl]-(4-chloro-3-methyl-1H-indazol-5-yl)methanone;

(2-chloro-3-methoxyphenyl)-[rac-(7R,9aR)-7-(4-chlorophenyl)-7-hydroxy-3,4,6,8,9,9a-hexahydro-1H-pyrido[1,2-a]pyrazin-2-yl]methanone;

[(7S,9aS)-7-(4-chlorophenyl)-7-hydroxy-3,4,6,8,9,9a-hexahydro-1H-pyrido[1,2-a]pyrazin-2-yl]-(2-chloro-3-methoxyphenyl)methanone;

[(7R,9aR)-7-(4-chlorophenyl)-7-hydroxy-3,4,6,8,9,9a-hexahydro-1H-pyrido[1,2-a]pyrazin-2-yl]-(2-chloro-3-methoxyphenyl)methanone;

(2-chloro-3-methoxyphenyl)-[rac-(7R,9aS)-7-(4-chlorophenyl)-7-hydroxy-3,4,6,8,9,9a-hexahydro-1H-pyrido[1,2-a]pyrazin-2-yl]methanone;

[(7S,9aR)-7-(4-chlorophenyl)-7-hydroxy-3,4,6,8,9,9a-hexahydro-1H-pyrido[1,2-a]pyrazin-2-yl]-(2-chloro-3-methoxyphenyl)methanone;

[(7R,9aS)-7-(4-chlorophenyl)-7-hydroxy-3,4,6,8,9,9a-hexahydro-1H-pyrido[1,2-a]pyrazin-2-yl]-(2-chloro-3-methoxyphenyl)methanone;

[2-chloro-3-(2-oxa-6-azaspiro[3.3]heptan-6-yl)phenyl]-[rac-(7R,9aR)-7-(4-chlorophenyl)-7-hydroxy-3,4,6,8,9,9a-hexahydro-1H-pyrido[1,2-a]pyrazin-2-yl]methanone;

[2-chloro-3-(2-oxa-6-azaspiro[3.3]heptan-6-yl)phenyl]-[rac-(7R,9aS)-7-(4-chlorophenyl)-7-hydroxy-3,4,6,8,9,9a-hexahydro-1H-pyrido[1,2-a]pyrazin-2-yl]methanone;

(2-chloro-3-methoxyphenyl)-[rac-(7R,9aR)-7-(4-chlorophenyl)-7-fluoro-3,4,6,8,9,9a-hexahydro-1H-pyrido[1,2-a]pyrazin-2-yl]methanone;

(2-chloro-3-methoxyphenyl)-[rac-(7R,9aS)-7-(4-chlorophenyl)-7-fluoro-3,4,6,8,9,9a-hexahydro-1H-pyrido[1,2-a]pyrazin-2-yl]methanone;

(2-chloro-3-methoxyphenyl)-[rac-(7R,9aR)-7-(4-chlorophenyl)-7-methoxy-3,4,6,8,9,9a-hexahydro-1H-pyrido[1,2-a]pyrazin-2-yl]methanone;

(2-chloro-3-methoxyphenyl)-[rac-(7R,9aS)-7-(4-chlorophenyl)-7-methoxy-3,4,6,8,9,9a-hexahydro-1H-pyrido[1,2-a]pyrazin-2-yl]methanone;

(2-chloro-3-methoxyphenyl)-[rac-(7R,9aS)-7-methyl-1,3,4,6,7,8,9,9a-octahydropyrido[1,2-a]pyrazin-2-yl]methanone;

(2-chloro-3-methoxyphenyl)-[rac-(7R,9aR)-7-methyl-1,3,4,6,7,8,9,9a-octahydropyrido[1,2-a]pyrazin-2-yl]methanone;

[(7R,9aR)-7-(4-chlorophenyl)-1,3,4,6,7,8,9,9a-octahydropyrido[1,2-a]pyrazin-2-yl]-(6-methoxypyridin-2-yl)methanone; and (6-amino-4-chloropyridin-3-yl)-[rac-(7R,9aR)-7-(3-chloro-4-fluorophenyl)-1,3,4,6,7,8,9,9a-octahydropyrido[1,2-a]pyrazin-2-yl]methanone.

E4 The compound of formula (I) according to any one of A1 and E2 to E3, or a pharmaceutically acceptable salt thereof, wherein $R^1$ is selected from the group consisting of (i) $C_6$-$C_{14}$-aryl substituted with 1-2 substituents independently selected from the group consisting of $C_{1-6}$-alkoxy, halogen, and a group

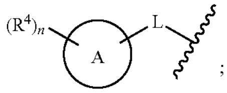

;

(ii) 5- to 6-membered heteroaryl optionally substituted with 1-2 substituents independently selected from the group consisting of halogen, hydroxy, $C_{1-6}$-alkoxy, —$B(OH)_2$, 5- to 6-membered heteroaryl, $C_{1-6}$-alkyl, and amino; and (iii) 5- to 14-membered heterocyclyl optionally substituted with 1-3 substituents independently selected from the group consisting of halogen, $C_{1-6}$-alkyl, and oxo.

E5 The compound of formula (I) according to any one of A1 and E2 to E3, or a pharmaceutically acceptable salt thereof, wherein $R^1$ is selected from the group consisting of (i) $C_6$-$C_{14}$-aryl substituted with 1-2 substituents independently selected from the group consisting of $C_{1-6}$-alkoxy, halogen, and a group

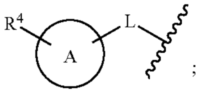

;

(ii) 5- to 6-membered heteroaryl substituted with 1-2 substituents independently selected from the group consisting of halogen, $C_{1-6}$-alkoxy, $C_{1-6}$-alkyl, and amino; and (iii) 5- to 14-membered heterocyclyl optionally substituted with 1-3 substituents independently selected from the group consisting of halogen, $C_{1-6}$-alkyl, and oxo.

E6 The compound of formula (I) according to any one of A1 and E2 to E3, or a pharmaceutically acceptable salt thereof, wherein $R^1$ is $C_6$-$C_{14}$-aryl substituted with 1-2 substituents independently selected from the group consisting of $C_{1-6}$-alkoxy, halogen, and a group

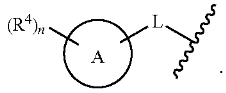

.

E7 The compound of formula (I) according to any one of A1 and E2 to E3, or a pharmaceutically acceptable salt thereof, wherein $R^1$ is $C_6$-$C_{14}$-aryl substituted with 1-2 substituents independently selected from the group consisting of $C_{1-6}$-alkoxy, halogen, and a group

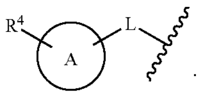

E8 The compound of formula (I) according to any one of A1 and E2 to E3, or a pharmaceutically acceptable salt thereof, wherein $R^1$ is phenyl substituted with 1-2 substituents independently selected from the group consisting of chloro, fluoro, methoxy and a group

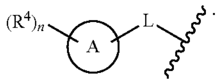

E9 The compound of formula (I) according to any one of A1 and E2 to E3, or a pharmaceutically acceptable salt thereof, wherein $R^1$ is phenyl substituted with 1-2 substituents independently selected from the group consisting of chloro, fluoro, methoxy and a group

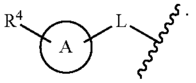

E10 The compound of formula (I) according to any one of A1 and E2 to E9, or a a pharmaceutically acceptable salt thereof, wherein $R^2$ is selected from the group consisting of (i) $C_{1-6}$-alkyl optionally substituted with 1-3 substituents independently selected from halogen;

(ii) $C_{3-14}$-cycloalkyl;

(iii) $C_6$-$C_{14}$-aryl substituted with 1-2 substituents independently selected from halogen;

(iv) 5- to 14-membered heteroaryl substituted with halo-$C_{1-6}$-alkyl; and (v) 5- to 14-membered heteroaryloxy substituted with halogen.

E11 The compound of formula (I) according to any one of A1 and E2 to E9, or a a pharmaceutically acceptable salt thereof, wherein $R^2$ is selected from the group consisting of (i) $C_{1-6}$-alkyl optionally substituted with 1-3 substituents independently selected from halogen;

(ii) $C_{3-14}$-cycloalkyl;

(iii) $C_6$-$C_{14}$-aryl substituted with 1-2 substituents independently selected from halogen; and (iv) 5- to 14-membered heteroaryl substituted with halo-$C_{1-6}$-alkyl.

E12 The compound of formula (I) according to any one of A1 and E2 to E9, or a pharmaceutically acceptable salt thereof, wherein $R^2$ is selected from the group consisting of (i) halo-$C_6$-$C_{14}$-aryl; and (ii) 5- to 14-membered heteroaryl substituted with halo-$C_{1-6}$-alkyl.

E13 The compound of formula (I) according to any one of A1 and E2 to E9, or a pharmaceutically acceptable salt thereof, wherein $R^2$ is selected from the group consisting of (i) chlorophenyl;

(ii) 3-chloro-4-fluoro-phenyl; and (iii) pyridyl substituted with $CF_3$.

E14 The compound of formula (I) according to any one of A1 and E2 to E9, or a pharmaceutically acceptable salt thereof, wherein $R^2$ is selected from the group consisting of (iv) chlorophenyl; and (v) pyridyl substituted with $CF_3$.

E15 The compound of formula (I) according to any one of A1 and E2 to E14, or a pharmaceutically acceptable salt thereof, wherein $R^3$ is hydrogen or hydroxy.

E16 The compound of formula (I) according to any one of A1 and E2 to E14, or a pharmaceutically acceptable salt thereof, wherein $R^3$ is hydroxy.

E17 The compound of formula (I) according to any one of A1 and E2 to E16, or a pharmaceutically acceptable salt thereof, wherein $R^4$ is selected from the group consisting of hydrogen, halogen, $C_{1-6}$-alkyl, hydroxy-$C_{1-6}$-alkyl, $C_{1-6}$-alkoxycarbonyl, $C_{1-6}$-alkoxycarbonyl-NH—, hydroxy and oxo.

E18 The compound of formula (I) according to any one of A1 and E2 to E16, or a pharmaceutically acceptable salt thereof, wherein $R^4$ is selected from the group consisting of hydrogen, halogen, $C_{1-6}$-alkyl, $C_{1-6}$-alkoxycarbonyl, $C_{1-6}$-alkoxycarbonyl-NH—, hydroxy and oxo.

E19 The compound of formula (I) according to any one of A1 and E2 to E16, or a pharmaceutically acceptable salt thereof, wherein $R^4$ is selected from the group consisting of hydrogen, halogen, and hydroxy.

E20 The compound of formula (I) according to any one of A1 and E2 to E16, or a pharmaceutically acceptable salt thereof, wherein $R^4$ is selected from the group consisting of hydrogen, fluoro, and hydroxy.

E21 The compound of formula (I) according to any one of A1 and E2 to E20, or a pharmaceutically acceptable salt thereof, wherein L is a covalent bond.

E22 The compound of formula (I) according to any one of A1 and E2 to E21, or a pharmaceutically acceptable salt thereof, wherein A is selected from the group consisting of 5- to 14-membered heteroaryl and 5- to 14-membered heterocyclyl.

E23 The compound of formula (I) according to any one of A1 and E2 to E21, or a pharmaceutically acceptable salt thereof, wherein A is selected from the group consisting of pyrazolyl and azetidinyl.

E24 The compound of formula (I) according to any one of A1 and E2 to E3, or a pharmaceutically acceptable salt thereof, wherein:

$R^1$ is selected from the group consisting of (i) $C_6$-$C_{14}$-aryl substituted with 1-2 substituents independently selected from the group consisting of $C_{1-6}$-alkoxy, halogen, and a group

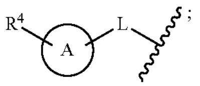

(ii) 5- to 6-membered heteroaryl substituted with 1-2 substituents independently selected from the group consisting of halogen, $C_{1-6}$-alkoxy, $C_{1-6}$-alkyl, and amino; and (iii) 5- to 14-membered heterocyclyl optionally substituted with 1-3 substituents independently selected from the group consisting of halogen, $C_{1-6}$-alkyl, and oxo;

$R^2$ is selected from the group consisting of (i) $C_{1-6}$-alkyl optionally substituted with 1-3 substituents independently selected from halogen;

(ii) $C_{3-14}$-cycloalkyl;

(iii) $C_6$-$C_{14}$-aryl substituted with 1-2 substituents independently selected from halogen; and (iv) 5- to 14-membered heteroaryl substituted with halo-$C_{1-6}$-alkyl;

$R^3$ is hydrogen or hydroxy;

$R^4$ is selected from the group consisting of hydrogen, halogen, $C_{1-6}$-alkyl, $C_{1-6}$-alkoxycarbonyl, $C_{1-6}$-alkoxycarbonyl-NH—, hydroxy and oxo;

L is selected from the group consisting of a covalent bond and —CH═CH—; and

A is selected from the group consisting of $C_6$-$C_{14}$-aryl, 5- to 14-membered heteroaryl, and 5- to 14-membered heterocyclyl.

E25 The compound of formula (I) according to A1, E2 and E3, or a pharmaceutically acceptable salt thereof, wherein:

$R^1$ is $C_6$-$C_{14}$-aryl substituted with 1-2 substituents independently selected from the group consisting of $C_{1-6}$-alkoxy, halogen, and a group

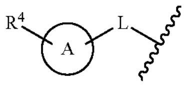 ;

$R^2$ is selected from the group consisting of (i) halo-$C_6$-$C_{14}$-aryl; and (ii) 5- to 14-membered heteroaryl substituted with halo-$C_{1-6}$-alkyl;

$R^3$ is hydroxy;

$R^4$ is selected from the group consisting of hydrogen, halogen, and hydroxy;

L is a covalent bond; and

A is selected from the group consisting of 5- to 14-membered heteroaryl, and 5- to 14-membered heterocyclyl.

E26 The compound of formula (I) according to A1, E2 and E3, or a pharmaceutically acceptable salt thereof, wherein:

$R^1$ is phenyl substituted with 1-2 substituents independently selected from the group consisting of chloro, fluoro, methoxy, and a group

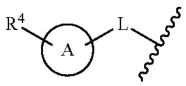 ;

$R^2$ is selected from the group consisting of (i) chlorophenyl; and (ii) pyridyl substituted with $CF_3$;

$R^3$ is hydroxy;

$R^4$ is selected from the group consisting of hydrogen, fluoro, and hydroxy;

L is a covalent bond; and

A is selected from the group consisting of pyrazolyl and azetidinyl.

E27 The compound of formula (I) according to A1, E2 and E3, or a pharmaceutically acceptable salt thereof, wherein:

$R^1$ is selected from the group consisting of (i) $C_6$-$C_{14}$-aryl substituted with 1-2 substituents independently selected from the group consisting of $C_{1-6}$-alkoxy, halogen, and a group

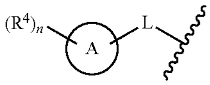 ;

(ii) 5- to 6-membered heteroaryl substituted with 1-2 substituents independently selected from the group consisting of halogen, $C_{1-6}$-alkoxy, $C_{1-6}$-alkyl, and amino; and (iii) 5- to 14-membered heterocyclyl optionally substituted with 1-3 substituents independently selected from the group consisting of halogen, $C_{1-6}$-alkyl, and oxo;

$R^2$ is selected from the group consisting of (i) $C_{1-6}$-alkyl optionally substituted with 1-3 substituents independently selected from halogen;

(ii) $C_{3-14}$-cycloalkyl;

(iii) $C_6$-$C_{14}$-aryl substituted with 1-2 substituents independently selected from halogen; and (iv) 5- to 14-membered heteroaryl substituted with halo-$C_{1-6}$-alkyl;

$R^3$ is hydrogen or hydroxy;

$R^4$ is selected from the group consisting of hydrogen, halogen, $C_{1-6}$-alkyl, $C_{1-6}$-alkoxycarbonyl, $C_{1-6}$-alkoxycarbonyl-NH—, hydroxy and oxo;

L is selected from the group consisting of a covalent bond and —CH═CH—;

A is selected from the group consisting of $C_6$-$C_{14}$-aryl, 5- to 14-membered heteroaryl, and 5- to 14-membered heterocyclyl; and n is 1 or 2.

E28 The compound of formula (I) according to A1, E2 and E3, or a pharmaceutically acceptable salt thereof, wherein:

$R^1$ is $C_6$-$C_{14}$-aryl substituted with 1-2 substituents independently selected from the group consisting of $C_{1-6}$-alkoxy, halogen, and a group

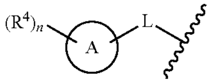 ;

$R^2$ is selected from the group consisting of (i) halo-$C_6$-$C_{14}$-aryl; and (ii) 5- to 14-membered heteroaryl substituted with halo-$C_{1-6}$-alkyl;

$R^3$ is hydroxy;

$R^4$ is selected from the group consisting of hydrogen, halogen, and hydroxy;

L is a covalent bond;

A is selected from the group consisting of 5- to 14-membered heteroaryl, and 5- to 14-membered heterocyclyl; and n is 1 or 2.

E29 The compound of formula (I) according to A1, E2 and E3, or a pharmaceutically acceptable salt thereof, wherein:

$R^1$ is phenyl substituted with 1-2 substituents independently selected from the group consisting of chloro, fluoro, methoxy, and a group

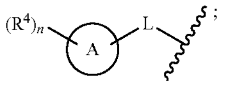

$R^2$ is selected from the group consisting of
(i) chlorophenyl;
(ii) 3-chloro-4-fluoro-phenyl; and
(iii) pyridyl substituted with $CF_3$;
$R^3$ is hydroxy;
$R^4$ is selected from the group consisting of hydrogen, fluoro, and hydroxy;
L is a covalent bond;
A is selected from the group consisting of pyrazolyl and azetidinyl; and
n is 1 or 2.

E30 The compound of formula (I) according to A1, or a pharmaceutically acceptable salt thereof, wherein the compound of formula (I) is selected from the group consisting of:
[(7S,9aR)-7-(3-chloro-4-fluorophenyl)-7-hydroxy-3,4,6,8,9,9a-hexahydro-TH-pyrido[1,2-a]pyrazin-2-yl]-(2-chloro-3-methoxyphenyl)methanone;
[(7R,9aS)-7-(3-chloro-4-fluorophenyl)-7-hydroxy-3,4,6,8,9,9a-hexahydro-TH-pyrido[1,2-a]pyrazin-2-yl]-(2-chloro-3-methoxyphenyl)methanone;
[(7S,9aR)-7-(4-chlorophenyl)-7-hydroxy-3,4,6,8,9,9a-hexahydro-1H-pyrido[1,2-a]pyrazin-2-yl]-[2-chloro-3-(1H-pyrazol-5-yl)phenyl]methanone;
[(7R,9aS)-7-(4-chlorophenyl)-7-hydroxy-3,4,6,8,9,9a-hexahydro-1H-pyrido[1,2-a]pyrazin-2-yl]-[2-chloro-3-(1H-pyrazol-5-yl)phenyl]methanone;
[(7S,9aR)-7-(4-chlorophenyl)-7-hydroxy-3,4,6,8,9,9a-hexahydro-TH-pyrido[1,2-a]pyrazin-2-yl]-[2-chloro-3-(3-fluoro-1H-pyrazol-4-yl)phenyl]methanone;
[(7R,9aS)-7-(4-chlorophenyl)-7-hydroxy-3,4,6,8,9,9a-hexahydro-TH-pyrido[1,2-a]pyrazin-2-yl]-[2-chloro-3-(3-fluoro-1H-pyrazol-4-yl)phenyl]methanone;
[(7S,9aR)-7-(4-chlorophenyl)-7-hydroxy-3,4,6,8,9,9a-hexahydro-1H-pyrido[1,2-a]pyrazin-2-yl]-(2-chloro-6-methoxypyridin-3-yl)methanone;
[(7S,9aR)-7-(4-chlorophenyl)-7-hydroxy-3,4,6,8,9,9a-hexahydro-TH-pyrido[1,2-a]pyrazin-2-yl]-(6-amino-2-methylpyridin-3-yl)methanone;
[(7S,9aR)-7-(4-chlorophenyl)-7-hydroxy-3,4,6,8,9,9a-hexahydro-TH-pyrido[1,2-a]pyrazin-2-yl]-[2-chloro-3-(3-hydroxyazetidin-1-yl)phenyl]methanone;
[(7S,9aR)-7-(4-chlorophenyl)-7-hydroxy-3,4,6,8,9,9a-hexahydro-1H-pyrido[1,2-a]pyrazin-2-yl]-[2-fluoro-3-(3-hydroxyazetidin-1-yl)phenyl]methanone;
5-[(7R,9aS)-7-(4-chlorophenyl)-7-hydroxy-3,4,6,8,9,9a-hexahydro-TH-pyrido[1,2-a]pyrazine-2-carbonyl]-6-chloro-1-methylpyridin-2-one;
5-[(7S,9aR)-7-(4-chlorophenyl)-7-hydroxy-3,4,6,8,9,9a-hexahydro-1H-pyrido[1,2-a]pyrazine-2-carbonyl]-6-chloro-1-methylpyridin-2-one;
3-[3-[(7S,9aR)-7-(4-chlorophenyl)-7-hydroxy-3,4,6,8,9,9a-hexahydro-1H-pyrido[1,2-a]pyrazine-2-carbonyl]-2-chlorophenyl]-1,3-oxazolidin-2-one;
1-[3-[(7S,9aR)-7-(4-chlorophenyl)-7-hydroxy-3,4,6,8,9,9a-hexahydro-1H-pyrido[1,2-a]pyrazine-2-carbonyl]-2-chlorophenyl]imidazolidin-2-one;
[(7S,9aR)-7-(4-chlorophenyl)-7-hydroxy-3,4,6,8,9,9a-hexahydro-1H-pyrido[1,2-a]pyrazin-2-yl]-[2-fluoro-3-(4-methyl-1H-pyrazol-3-yl)phenyl]methanone;
[(7S,9aR)-7-(4-chlorophenyl)-7-hydroxy-3,4,6,8,9,9a-hexahydro-1H-pyrido[1,2-a]pyrazin-2-yl]-[2-chloro-3-(4-methyl-1H-pyrazol-5-yl)phenyl]methanone;
[(7S,9aR)-7-(4-chlorophenyl)-7-hydroxy-3,4,6,8,9,9a-hexahydro-1H-pyrido[1,2-a]pyrazin-2-yl]-[3-(4-methyl-1H-pyrazol-3-yl)phenyl]methanone;
[(7R,9aR)-7-hydroxy-7-[5-(trifluoromethyl)pyridin-2-yl]-3,4,6,8,9,9a-hexahydro-1H-pyrido[1,2-a]pyrazin-2-yl]-(2-chloro-3-methoxyphenyl)methanone;
[(7S,9aS)-7-hydroxy-7-[5-(trifluoromethyl)pyridin-2-yl]-3,4,6,8,9,9a-hexahydro-1H-pyrido[1,2-a]pyrazin-2-yl]-(2-chloro-3-methoxyphenyl)methanone;
[(7R,9aR)-7-hydroxy-7-[5-(trifluoromethyl)pyridin-2-yl]-3,4,6,8,9,9a-hexahydro-1H-pyrido[1,2-a]pyrazin-2-yl]-[2-chloro-3-(1H-pyrazol-5-yl)phenyl]methanone;
[(7S,9aR)-7-(4-chlorophenyl)-7-hydroxy-3,4,6,8,9,9a-hexahydro-1H-pyrido[1,2-a]pyrazin-2-yl]-(2-fluoro-3-morpholin-4-ylphenyl)methanone;
tert-butyl4-[3-[(7S,9aR)-7-(4-chlorophenyl)-7-hydroxy-3,4,6,8,9,9a-hexahydro-1H-pyrido[1,2-a]pyrazine-2-carbonyl]-2-fluorophenyl]piperazine-1-carboxylate;
[(7S,9aR)-7-(4-chlorophenyl)-7-hydroxy-3,4,6,8,9,9a-hexahydro-1H-pyrido[1,2-a]pyrazin-2-yl]-(2-fluoro-3-piperazin-1-ylphenyl)methanone;
(2-chloro-3-methoxyphenyl)-[rac-(7R,9aS)-7-hydroxy-7-(2-methylpropyl)-3,4,6,8,9,9a-hexahydro-1H-pyrido[1,2-a]pyrazin-2-yl]methanone;
(2-chloro-3-methoxyphenyl)-[rac-(7R,9aS)-7-cyclopentyl-7-hydroxy-3,4,6,8,9,9a-hexahydro-1H-pyrido[1,2-a]pyrazin-2-yl]methanone;
(2-chloro-3-methoxyphenyl)-[rac-(7R,9aR)-7-hydroxy-7-(trifluoromethyl)-3,4,6,8,9,9a-hexahydro-1H-pyrido[1,2-a]pyrazin-2-yl]methanone;
[(7R,9aR)-7-(4-chlorophenyl)-1,3,4,6,7,8,9,9a-octahydropyrido[1,2-a]pyrazin-2-yl]-[2-bromo-3-[(Z)-2-phenylethenyl]phenyl]methanone;
[(7R,9aR)-7-(4-chlorophenyl)-1,3,4,6,7,8,9,9a-octahydropyrido[1,2-a]pyrazin-2-yl]-[2-bromo-3-[(E)-2-phenylethenyl]phenyl]methanone;
tert-butylN-[4-[(E)-2-[3-[(7R,9aR)-7-(4-chlorophenyl)-1,3,4,6,7,8,9,9a-octahydropyrido[1,2-a]pyrazine-2-carbonyl]-2-bromophenyl]ethenyl]phenyl]carbamate;
N-[4-[(E)-2-[3-[(7R,9aR)-7-(4-chlorophenyl)-1,3,4,6,7,8,9,9a-octahydropyrido[1,2-a]pyrazine-2-carbonyl]-2-bromophenyl]ethenyl]phenyl]prop-2-enamide;
4-[(E)-2-[3-[(7R,9aR)-7-(4-chlorophenyl)-1,3,4,6,7,8,9,9a-octahydropyrido[1,2-a]pyrazine-2-carbonyl]-2-bromo-phenyl]vinyl]-N-methyl-benzamide;
[(7R,9aR)-7-hydroxy-7-[5-(trifluoromethyl)pyridin-2-yl]-3,4,6,8,9,9a-hexahydro-1H-pyrido[1,2-a]pyrazin-2-yl]-[2-chloro-3-(3-hydroxyazetidin-1-yl)phenyl]methanone;
[(7S,9aR)-7-(4-chlorophenyl)-7-hydroxy-3,4,6,8,9,9a-hexahydro-1H-pyrido[1,2-a]pyrazin-2-yl]-(2-chloro-3-hydroxyphenyl)methanone;

4-(3-((7S,9aR)-7-(4-chlorophenyl)-7-hydroxyoctahydro-2H-pyrido[1,2-a]pyrazine-2-carbonyl)-2-fluorophenyl)piperazin-2-one;

4-[3-[(7S,9aR)-7-(4-chlorophenyl)-7-hydroxy-3,4,6,8,9,9a-hexahydro-1H-pyrido[1,2-a]pyrazine-2-carbonyl]-2-chlorophenyl]piperazin-2-one;

[(7S,9aR)-7-(4-chlorophenyl)-7-hydroxy-3,4,6,8,9,9a-hexahydro-1H-pyrido[1,2-a]pyrazin-2-yl]-[2-chloro-3-(6-oxa-1-azaspiro[3.3]heptan-1-yl)phenyl]methanone;

[(7S,9aS)-7-hydroxy-7-[5-(trifluoromethyl)pyridin-2-yl]-3,4,6,8,9,9a-hexahydro-1H-pyrido[1,2-a]pyrazin-2-yl]-[2-chloro-3-(difluoromethoxy)phenyl]methanone;

[(7R,9aR)-7-hydroxy-7-[5-(trifluoromethyl)pyridin-2-yl]-3,4,6,8,9,9a-hexahydro-1H-pyrido[1,2-a]pyrazin-2-yl]-[2-chloro-3-(difluoromethoxy)phenyl]methanone;

[(7S,9aR)-7-(3-chloro-4-fluorophenyl)-7-hydroxy-3,4,6,8,9,9a-hexahydro-1H-pyrido[1,2-a]pyrazin-2-yl]-[2-fluoro-3-(3-hydroxyazetidin-1-yl)phenyl]methanone;

[(7S,9aR)-7-(3-chloro-4-fluorophenyl)-7-hydroxy-3,4,6,8,9,9a-hexahydro-1H-pyrido[1,2-a]pyrazin-2-yl]-[2-chloro-3-(3-hydroxyazetidin-1-yl)phenyl]methanone;

[(7R,9aR)-7-hydroxy-7-[5-(trifluoromethyl)pyridin-2-yl]-3,4,6,8,9,9a-hexahydro-1H-pyrido[1,2-a]pyrazin-2-yl]-(2-chloro-3-fluorophenyl)methanone;

[(7S,9aS)-7-hydroxy-7-[5-(trifluoromethyl)pyridin-2-yl]-3,4,6,8,9,9a-hexahydro-1H-pyrido[1,2-a]pyrazin-2-yl]-(2-chloro-3-fluorophenyl)methanone;

[(7S,9aR)-7-(3-chloro-4-fluorophenyl)-7-hydroxy-3,4,6,8,9,9a-hexahydro-1H-pyrido[1,2-a]pyrazin-2-yl]-[2-chloro-3-[(3 S)-3-hydroxypyrrolidin-1-yl]phenyl]methanone;

[(7S,9aR)-7-(3-chloro-4-fluorophenyl)-7-hydroxy-3,4,6,8,9,9a-hexahydro-1H-pyrido[1,2-a]pyrazin-2-yl]-[2-chloro-3-[(3R)-3-hydroxypyrrolidin-1-yl]phenyl]methanone;

[(7S,9aR)-7-(4-chlorophenyl)-7-hydroxy-3,4,6,8,9,9a-hexahydro-1H-pyrido[1,2-a]pyrazin-2-yl]-[2-chloro-3-[(3R)-3-hydroxypyrrolidin-1-yl]phenyl]methanone;

[(7S,9aR)-7-(4-chlorophenyl)-7-hydroxy-3,4,6,8,9,9a-hexahydro-1H-pyrido[1,2-a]pyrazin-2-yl]-[2-chloro-3-(3-hydroxy-3-methylazetidin-1-yl)phenyl]methanone;

[(7S,9aR)-7-(3-chloro-4-fluorophenyl)-7-hydroxy-3,4,6,8,9,9a-hexahydro-1H-pyrido[1,2-a]pyrazin-2-yl]-[2-chloro-3-[(3S)-3-hydroxypiperidin-1-yl]phenyl]methanone;

[(7S,9aR)-7-(3-chloro-4-fluorophenyl)-7-hydroxy-3,4,6,8,9,9a-hexahydro-1H-pyrido[1,2-a]pyrazin-2-yl]-[2-chloro-3-[(3R)-3-hydroxypiperidin-1-yl]phenyl]methanone;

[(7S,9aR)-7-(4-chlorophenyl)-7-hydroxy-3,4,6,8,9,9a-hexahydro-1H-pyrido[1,2-a]pyrazin-2-yl]-[2-chloro-3-(4-hydroxypiperidin-1-yl)phenyl]methanone;

[2-chloro-3-(3-hydroxy-3-methylpyrrolidin-1-yl)phenyl]-[rac-(7R,9aS)-7-(4-chlorophenyl)-7-hydroxy-3,4,6,8,9,9a-hexahydro-1H-pyrido[1,2-a]pyrazin-2-yl]methanone;

[(7S,9aR)-7-(3-chloro-4-fluorophenyl)-7-hydroxy-3,4,6,8,9,9a-hexahydro-1H-pyrido[1,2-a]pyrazin-2-yl]-[2-chloro-3-[(3S,4S)-3,4-dihydroxypyrrolidin-1-yl]phenyl]methanone;

[(7S,9aR)-7-(3-chloro-4-fluorophenyl)-7-hydroxy-3,4,6,8,9,9a-hexahydro-1H-pyrido[1,2-a]pyrazin-2-yl]-[2-chloro-3-[3-fluoro-3-(hydroxymethyl)azetidin-1-yl]phenyl]methanone;

[(7S,9aR)-7-(3-chloro-4-fluorophenyl)-7-hydroxy-3,4,6,8,9,9a-hexahydro-1H-pyrido[1,2-a]pyrazin-2-yl]-[2-chloro-3-[3-(hydroxymethyl)azetidin-1-yl]phenyl]methanone;

[(7S,9aR)-7-(3-chloro-4-fluorophenyl)-7-hydroxy-3,4,6,8,9,9a-hexahydro-1H-pyrido[1,2-a]pyrazin-2-yl]-[2-chloro-3-(1H-pyrazol-3-yl)phenyl]methanone;

[(7S,9aR)-7-(3-chloro-4-fluorophenyl)-7-hydroxy-3,4,6,8,9,9a-hexahydro-1H-pyrido[1,2-a]pyrazin-2-yl]-[2-fluoro-3-(1H-pyrazol-3-yl)phenyl]methanone;

[(7S,9aR)-7-(4-chlorophenyl)-7-hydroxy-3,4,6,8,9,9a-hexahydro-1H-pyrido[1,2-a]pyrazin-2-yl]-[2-fluoro-3-(1,2-thiazol-3-yl)phenyl]methanone;

[(7S,9aR)-7-(3-chloro-4-fluorophenyl)-7-hydroxy-3,4,6,8,9,9a-hexahydro-1H-pyrido[1,2-a]pyrazin-2-yl]-[2-chloro-3-(4-fluoro-1H-pyrazol-5-yl)phenyl]methanone;

[(7S,9aR)-7-(3-chloro-4-fluorophenyl)-7-hydroxy-3,4,6,8,9,9a-hexahydro-1H-pyrido[1,2-a]pyrazin-2-yl]-[2-chloro-3-(1,2,4-thiadiazol-3-yl)phenyl]methanone;

[(7S,9aR)-7-(3,4-difluorophenyl)-7-hydroxy-3,4,6,8,9,9a-hexahydro-1H-pyrido[1,2-a]pyrazin-2-yl]-(2-chloro-3-methoxyphenyl)methanone;

[(7R,9aS)-7-(3,4-difluorophenyl)-7-hydroxy-3,4,6,8,9,9a-hexahydro-1H-pyrido[1,2-a]pyrazin-2-yl]-(2-chloro-3-methoxyphenyl)methanone;

[(7S,9aR)-7-(3,4-difluorophenyl)-7-hydroxy-3,4,6,8,9,9a-hexahydro-1H-pyrido[1,2-a]pyrazin-2-yl]-[2-fluoro-3-(1H-pyrazol-5-yl)phenyl]methanone;

[(7S,9aR)-7-(3,4-difluorophenyl)-7-hydroxy-3,4,6,8,9,9a-hexahydro-1H-pyrido[1,2-a]pyrazin-2-yl]-[2-fluoro-3-(4-fluoro-1H-pyrazol-5-yl)phenyl]methanone;

[(7S,9aR)-7-(3,4-difluorophenyl)-7-hydroxy-3,4,6,8,9,9a-hexahydro-1H-pyrido[1,2-a]pyrazin-2-yl]-[2-chloro-3-(3-hydroxyazetidin-1-yl)phenyl]methanone;

[(7R,9aR)-7-hydroxy-7-[5-(trifluoromethyl)pyridin-2-yl]-3,4,6,8,9,9a-hexahydro-1H-pyrido[1,2-a]pyrazin-2-yl]-[2-chloro-3-(4-fluoro-1H-pyrazol-5-yl)phenyl]methanone;

[(7S,9aR)-7-(3-chloro-4-fluorophenyl)-7-hydroxy-3,4,6,8,9,9a-hexahydro-1H-pyrido[1,2-a]pyrazin-2-yl]-(2,3-dihydro-1H-indol-4-yl)methanone;

[(7S,9aR)-7-(4-chlorophenyl)-7-hydroxy-3,4,6,8,9,9a-hexahydro-1H-pyrido[1,2-a]pyrazin-2-yl]-[4-chloro-5-(1H-pyrazol-3-yl)pyridin-3-yl]methanone;

[(7S,9aR)-7-(4-chlorophenyl)-7-hydroxy-3,4,6,8,9,9a-hexahydro-1H-pyrido[1,2-a]pyrazin-2-yl]-[2-chloro-3-(1,2-thiazol-3-yl)phenyl]methanone;

[(7S,9aR)-7-(4-chlorophenyl)-7-hydroxy-3,4,6,8,9,9a-hexahydro-1H-pyrido[1,2-a]pyrazin-2-yl]-[2-chloro-3-(1,2-thiazol-4-yl)phenyl]methanone;

[(7R,9aR)-7-hydroxy-7-[5-(trifluoromethyl)pyridin-2-yl]-3,4,6,8,9,9a-hexahydro-1H-pyrido[1,2-a]pyrazin-2-yl]-[2-chloro-3-(1,2-thiazol-3-yl)phenyl]methanone;

[(7S,9aR)-7-(4-chlorophenyl)-7-hydroxy-3,4,6,8,9,9a-hexahydro-1H-pyrido[1,2-a]pyrazin-2-yl]-[4-methyl-5-(1H-pyrazol-3-yl)pyridin-3-yl]methanone;

(2-chloro-3-methoxyphenyl)-[rac-(7R,9aS)-7-hydroxy-7-[6-(trifluoromethyl)pyridin-3-yl]-3,4,6,8,9,9a-hexahydro-1H-pyrido[1,2-a]pyrazin-2-yl]methanone; and (2-chloro-3-methoxyphenyl)-[rac-(7R,9aR)-7-hydroxy-7-[6-(trifluoromethyl)pyridin-3-yl]-3,4,6,8,9,9a-hexahydro-1H-pyrido[1,2-a]pyrazin-2-yl]methanone.

E31 The compound of formula (I) according to A1, or a pharmaceutically acceptable salt thereof, wherein the compound of formula (I) is selected from the group consisting of:

[(7S,9aR)-7-(3-chloro-4-fluorophenyl)-7-hydroxy-3,4,6,8,9,9a-hexahydro-1H-pyrido[1,2-a]pyrazin-2-yl]-(2-chloro-3-methoxyphenyl)methanone;

[(7S,9aR)-7-(4-chlorophenyl)-7-hydroxy-3,4,6,8,9,9a-hexahydro-1H-pyrido[1,2-a]pyrazin-2-yl]-[2-chloro-3-(1H-pyrazol-5-yl)phenyl]methanone;

[(7S,9aR)-7-(4-chlorophenyl)-7-hydroxy-3,4,6,8,9,9a-hexahydro-1H-pyrido[1,2-a]pyrazin-2-yl]-[2-chloro-3-(3-fluoro-1H-pyrazol-4-yl)phenyl]methanone;

[(7S,9aR)-7-(4-chlorophenyl)-7-hydroxy-3,4,6,8,9,9a-hexahydro-1H-pyrido[1,2-a]pyrazin-2-yl]-[2-chloro-3-(3-hydroxyazetidin-1-yl)phenyl]methanone;

[(7S,9aR)-7-(4-chlorophenyl)-7-hydroxy-3,4,6,8,9,9a-hexahydro-1H-pyrido[1,2-a]pyrazin-2-yl]-[2-fluoro-3-(3-hydroxyazetidin-1-yl)phenyl]methanone;

[(7R,9aR)-7-hydroxy-7-[5-(trifluoromethyl)pyridin-2-yl]-3,4,6,8,9,9a-hexahydro-1H-pyrido[1,2-a]pyrazin-2-yl]-(2-chloro-3-methoxyphenyl)methanone;

[(7R,9aR)-7-hydroxy-7-[5-(trifluoromethyl)pyridin-2-yl]-3,4,6,8,9,9a-hexahydro-1H-pyrido[1,2-a]pyrazin-2-yl]-[2-chloro-3-(1H-pyrazol-5-yl)phenyl]methanone;

[(7S,9aR)-7-(3-chloro-4-fluorophenyl)-7-hydroxy-3,4,6,8,9,9a-hexahydro-1H-pyrido[1,2-a]pyrazin-2-yl]-[2-chloro-3-(3-hydroxyazetidin-1-yl)phenyl]methanone;

[(7S,9aR)-7-(3-chloro-4-fluorophenyl)-7-hydroxy-3,4,6,8,9,9a-hexahydro-1H-pyrido[1,2-a]pyrazin-2-yl]-[2-chloro-3-[(3R)-3-hydroxypyrrolidin-1-yl]phenyl]methanone;

[(7S,9aR)-7-(3-chloro-4-fluorophenyl)-7-hydroxy-3,4,6,8,9,9a-hexahydro-1H-pyrido[1,2-a]pyrazin-2-yl]-[2-chloro-3-[(3S,4S)-3,4-dihydroxypyrrolidin-1-yl]phenyl]methanone;

[(7S,9aR)-7-(3-chloro-4-fluorophenyl)-7-hydroxy-3,4,6,8,9,9a-hexahydro-1H-pyrido[1,2-a]pyrazin-2-yl]-[2-chloro-3-(1H-pyrazol-3-yl)phenyl]methanone;

[(7S,9aR)-7-(3-chloro-4-fluorophenyl)-7-hydroxy-3,4,6,8,9,9a-hexahydro-1H-pyrido[1,2-a]pyrazin-2-yl]-[2-fluoro-3-(1H-pyrazol-3-yl)phenyl]methanone;

[(7S,9aR)-7-(3-chloro-4-fluorophenyl)-7-hydroxy-3,4,6,8,9,9a-hexahydro-1H-pyrido[1,2-a]pyrazin-2-yl]-[2-chloro-3-(4-fluoro-1H-pyrazol-5-yl)phenyl]methanone;

[(7S,9aR)-7-(3,4-difluorophenyl)-7-hydroxy-3,4,6,8,9,9a-hexahydro-1H-pyrido[1,2-a]pyrazin-2-yl]-(2-chloro-3-methoxyphenyl)methanone;

[(7S,9aR)-7-(3,4-difluorophenyl)-7-hydroxy-3,4,6,8,9,9a-hexahydro-1H-pyrido[1,2-a]pyrazin-2-yl]-[2-fluoro-3-(1H-pyrazol-5-yl)phenyl]methanone; and

[(7R,9aR)-7-hydroxy-7-[5-(trifluoromethyl)pyridin-2-yl]-3,4,6,8,9,9a-hexahydro-1H-pyrido[1,2-a]pyrazin-2-yl]-[2-chloro-3-(4-fluoro-1H-pyrazol-5-yl)phenyl]methanone.

In a further embodiment, the present invention provides a compound of formula (I) as described herein, or a pharmaceutically acceptable salt thereof, wherein $R^1$ is selected from the group consisting of (i) $C_6$-$C_{14}$-aryl substituted with 1-2 substituents independently selected from the group consisting of $C_{1-6}$-alkoxy, halogen, and a group

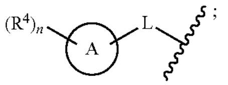

(ii) 5- to 6-membered heteroaryl substituted with 1-2 substituents independently selected from the group consisting of halogen, $C_{1-6}$-alkoxy, $C_{1-6}$-alkyl, and amino; and (iii) 5- to 14-membered heterocyclyl optionally substituted with 1-3 substituents independently selected from the group consisting of halogen, $C_{1-6}$-alkyl, and oxo;

$R^4$ is selected from the group consisting of hydrogen, halogen, $C_{1-6}$-alkyl, $C_{1-6}$-alkoxycarbonyl, $C_{1-6}$-alkoxycarbonyl-NH—, hydroxy and oxo;

L is selected from the group consisting of a covalent bond and —CH═CH—;

A is selected from the group consisting of $C_6$-$C_{14}$-aryl, 5- to 14-membered heteroaryl, and 5- to 14-membered heterocyclyl; and n is 1 or 2.

In a further embodiment, the present invention provides a compound of formula (I) as described herein, or a pharmaceutically acceptable salt thereof, wherein $R^1$ is selected from the group consisting of (i) $C_6$-$C_{14}$-aryl substituted with 1-2 substituents independently selected from the group consisting of $C_{1-6}$-alkoxy, halogen, and a group

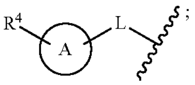

(ii) 5- to 6-membered heteroaryl substituted with 1-2 substituents independently selected from the group consisting of halogen, $C_{1-6}$-alkoxy, $C_{1-6}$-alkyl, and amino; and (iii) 5- to 14-membered heterocyclyl optionally substituted with 1-3 substituents independently selected from the group consisting of halogen, $C_{1-6}$-alkyl, and oxo;

$R^4$ is selected from the group consisting of hydrogen, halogen, $C_{1-6}$-alkyl, $C_{1-6}$-alkoxycarbonyl, $C_{1-6}$-alkoxycarbonyl-NH—, hydroxy and oxo;

L is selected from the group consisting of a covalent bond and —CH═CH—; and

A is selected from the group consisting of $C_6$-$C_{14}$-aryl, 5- to 14-membered heteroaryl, and 5- to 14-membered heterocyclyl.

In a preferred embodiment, the present invention provides a compound of formula (I) as described herein, or a pharmaceutically acceptable salt thereof, wherein $R^1$ is $C_6$-$C_{14}$-aryl substituted with 1-2 substituents independently selected from the group consisting of $C_{1-6}$-alkoxy, halogen, and a group

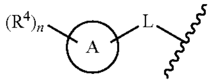
;

$R^4$ is selected from the group consisting of hydrogen, halogen, and hydroxy;

L is a covalent bond;

A is selected from the group consisting of 5- to 14-membered heteroaryl, and 5- to 14-membered heterocyclyl; and n is 1 or 2.

In a preferred embodiment, the present invention provides a compound of formula (I) as described herein, or a pharmaceutically acceptable salt thereof, wherein $R^1$ is $C_6$-$C_{14}$-aryl substituted with 1-2 substituents independently selected from the group consisting of $C_{1-6}$-alkoxy, halogen, and a group

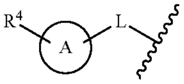
;

$R^4$ is selected from the group consisting of hydrogen, halogen, and hydroxy;

L is a covalent bond; and

A is selected from the group consisting of 5- to 14-membered heteroaryl, and 5- to 14-membered heterocyclyl.

In a particularly preferred embodiment, the present invention provides a compound of formula (I) as described herein, or a pharmaceutically acceptable salt thereof, wherein $R^1$ is phenyl substituted with 1-2 substituents independently selected from the group consisting of chloro, fluoro, methoxy, and a group

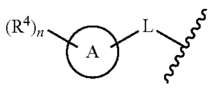
;

$R^4$ is selected from the group consisting of hydrogen, fluoro, and hydroxy;

L is a covalent bond;

A is selected from the group consisting of pyrazolyl and azetidinyl; and n is 1 or 2.

In a particularly preferred embodiment, the present invention provides a compound of formula (I) as described herein, or a pharmaceutically acceptable salt thereof, wherein $R^1$ is phenyl substituted with 1-2 substituents independently selected from the group consisting of chloro, fluoro, methoxy, and a group

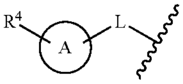
;

$R^4$ is selected from the group consisting of hydrogen, fluoro, and hydroxy;

L is a covalent bond; and

A is selected from the group consisting of pyrazolyl and azetidinyl.

In one embodiment, the present invention provides a compound of formula (I) as described herein, or a pharmaceutically acceptable salt thereof, wherein $R^2$ is selected from the group consisting of (i) $C_{1-6}$-alkyl optionally substituted with 1-3 substituents independently selected from halogen;

(ii) $C_{3-14}$-cycloalkyl;

(iii) $C_6$-$C_{14}$-aryl substituted with 1-2 substituents independently selected from halogen; and (iv) 5- to 14-membered heteroaryl substituted with halo-$C_{1-6}$-alkyl; and $R^3$ is hydrogen or hydroxy.

In a preferred embodiment, the present invention provides a compound of formula (I) as described herein, or a pharmaceutically acceptable salt thereof, wherein $R^2$ is selected from the group consisting of (i) halo-$C_6$-$C_{14}$-aryl; and (ii) 5- to 14-membered heteroaryl substituted with halo-$C_{1-6}$-alkyl; and $R^3$ is hydroxy.

In a particularly preferred embodiment, the present invention provides a compound of formula (I) as described herein, or a pharmaceutically acceptable salt thereof, wherein $R^2$ is selected from the group consisting of (i) chlorophenyl; and (ii) pyridyl substituted with $CF_3$; and $R^3$ is hydroxy.

In one embodiment, there is provided a compound of formula (I) as described herein, wherein the compound of formula (I) is a compound of formula (II)

(II)

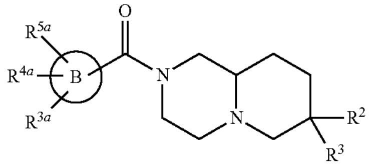

or a pharmaceutically acceptable salt thereof, wherein:

(a) B is phenyl;

$R^2$ is phenyl substituted with one or more halogen atoms;

$R^3$ is selected from the group consisting of hydrogen, halogen, alkoxy, cycloalkyloxy, and hydroxy;

$R^{3a}$ is hydrogen or halogen;

$R^{4a}$ is selected from the group consisting of (i) heterocyclyl optionally substituted with a substituent selected from the group consisting of hydroxy, oxo, alkoxycarbonyl, and hydroxycycloalkyl; and
(ii) heteroaryl; and
$R^{5a}$ is hydrogen; or
(b) B is phenyl;
$R^2$ is selected from the group consisting of
(i) heterocyclyl optionally substituted with 1-3 substituents selected from the group consisting of halogen, alkyl, and haloalkyl;
(ii) heteroaryl optionally substituted with 1-3 substituents selected from the group consisting of halogen, alkyl, and haloalkyl; and
(iii) cycloalkyl optionally substituted with 1-3 substituents selected from the group consisting of halogen, alkyl, and haloalkyl;
$R^3$ is selected from the group consisting of hydrogen, halogen, alkoxy, cycloalkyloxy, and hydroxy; and
$R^{3a}$, $R^{4a}$, and $R^{5a}$ are independently selected from hydrogen, halogen, alkoxy, and heteroaryl; or
(c) B is phenyl;
$R^2$ is

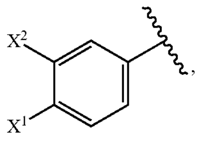

wherein $X^1$ and $X^2$ are each independently halogen;
$R^3$ is hydroxy; and
$R^{3a}$, $R^{4a}$, and $R^{5a}$ are independently selected from hydrogen, halogen, amino, alkyl, and alkoxy;
(d) B is heteroaryl or heterocyclyl;
$R^2$ is phenyl substituted with one or more halogen atoms;
$R^3$ is hydroxy; and
$R^{3a}$, $R^{4a}$, and $R^{5a}$ are independently selected from hydrogen, halogen, alkyl, alkoxy, amino, and oxo; or
(e) B is phenyl;
$R^2$ is alkyl or haloalkyl;
$R^3$ is hydroxy; and
$R^{3a}$, $R^{4a}$, and $R^{5a}$ are independently selected from hydrogen, halogen and alkoxy; with the proviso that the compound of formula (I) is not:

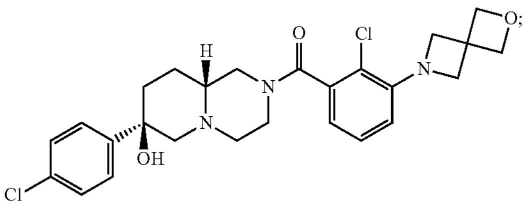

; or

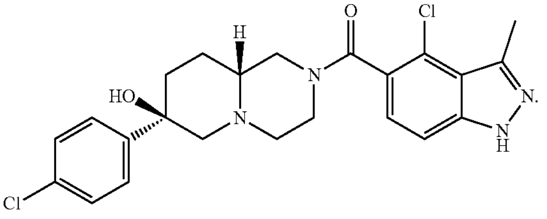

.

In one embodiment, there is provided a compound of formula (I) as described herein, wherein the compound of formula (I) is a compound of formula (II)

(II)

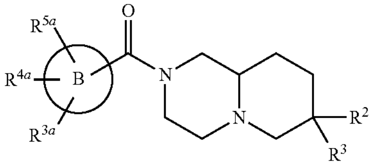

or a pharmaceutically acceptable salt thereof, wherein:
(a) B is phenyl;
$R^2$ is phenyl substituted with one or more halogen atoms;
$R^3$ is selected from the group consisting of hydrogen, halogen, alkoxy, cycloalkyloxy, and hydroxy;
$R^{3a}$ is hydrogen or halogen;
$R^{4a}$ is selected from the group consisting of
(i) heterocyclyl optionally substituted with a substituent selected from the group consisting of hydroxy, oxo, alkoxycarbonyl, and hydroxycycloalkyl; and
(ii) heteroaryl; and
$R^{5a}$ is hydrogen; or
(b) B is phenyl;
$R^2$ is selected from the group consisting of
(i) heterocyclyl optionally substituted with 1-3 substituents selected from the group consisting of halogen, alkyl, and haloalkyl;
(ii) heteroaryl optionally substituted with 1-3 substituents selected from the group consisting of halogen, alkyl, and haloalkyl; and
(iii) cycloalkyl optionally substituted with 1-3 substituents selected from the group consisting of halogen, alkyl, and haloalkyl;
$R^3$ is selected from the group consisting of hydrogen, halogen, alkoxy, cycloalkyloxy, and hydroxy; and
$R^{3a}$, $R^{4a}$, and $R^{5a}$ are independently selected from hydrogen, halogen, alkoxy, and heteroaryl; or
(c) B is phenyl;
$R^2$ is

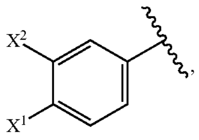

wherein $X^1$ and $X^2$ are each independently halogen;
$R^3$ is selected from the group consisting of hydrogen, halogen, alkoxy, cycloalkyloxy, and hydroxy; and
$R^{3a}$, $R^{4a}$, and $R^{5a}$ are independently selected from hydrogen, halogen, amino, alkyl, and alkoxy;
(d) B is heteroaryl or heterocyclyl;
$R^2$ is phenyl substituted with one or more halogen atoms;
$R^3$ is selected from the group consisting of hydrogen, halogen, alkoxy, cycloalkyloxy, and hydroxy; and
$R^{3a}$, $R^{4a}$, and $R^{5a}$ are independently selected from hydrogen, halogen, alkyl, alkoxy, amino, and oxo; or
(e) B is phenyl;
$R^2$ is alkyl or haloalkyl;
$R^3$ is selected from the group consisting of hydrogen, halogen, alkoxy, cycloalkyloxy, and hydroxy; and $R^{3a}$, $R^{4a}$, and $R^{5a}$ are independently selected from hydrogen, halogen and alkoxy; with the proviso that the compound of formula (I) is not:
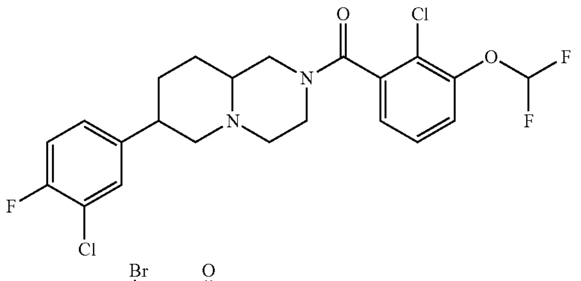
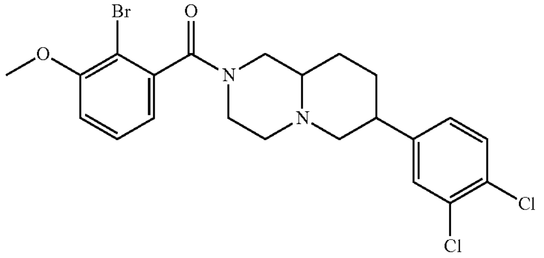
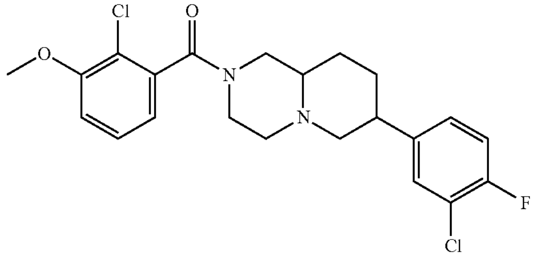
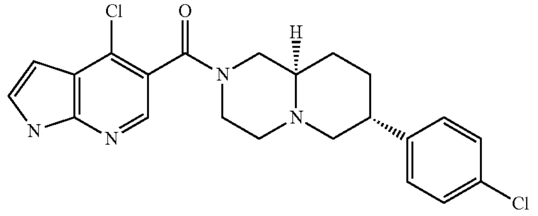
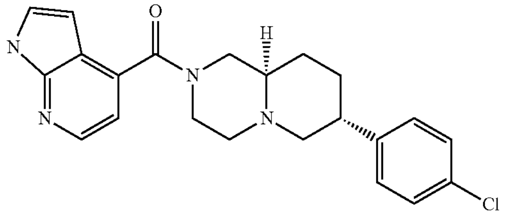
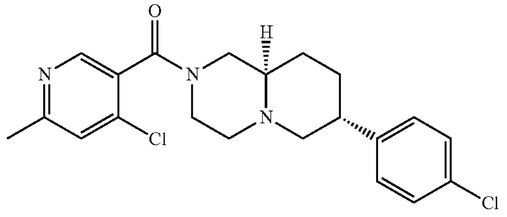
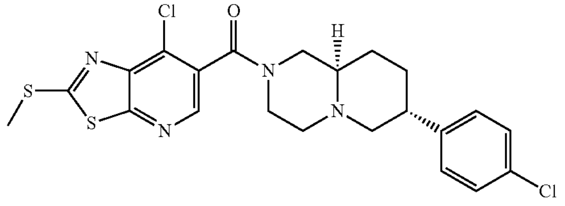
-continued
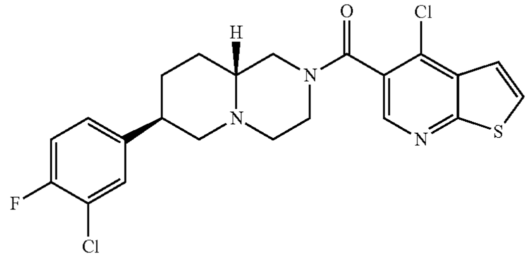
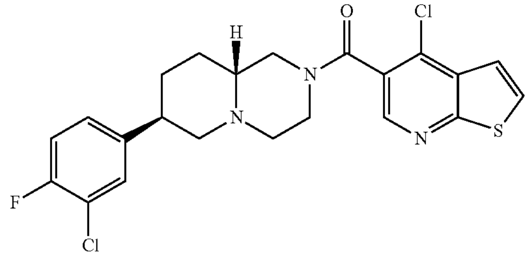
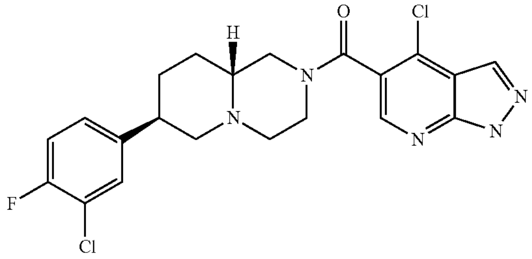
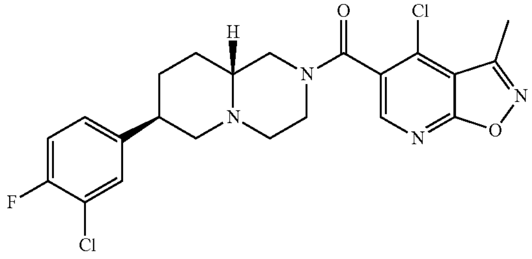
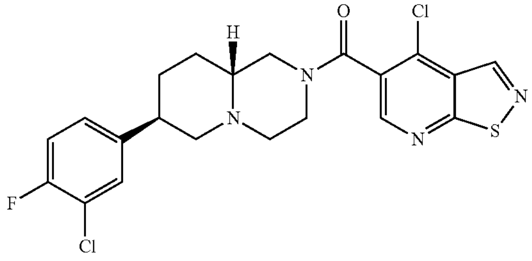
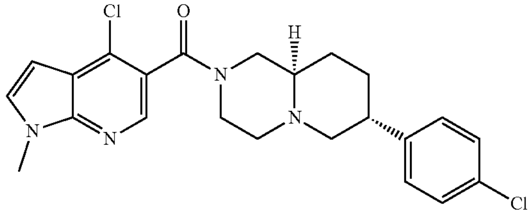
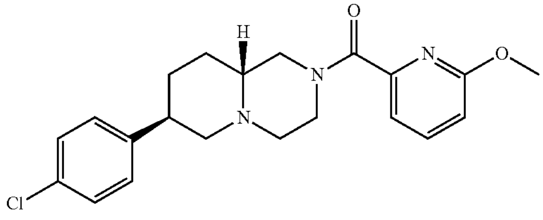

-continued
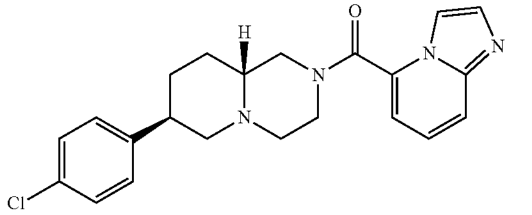
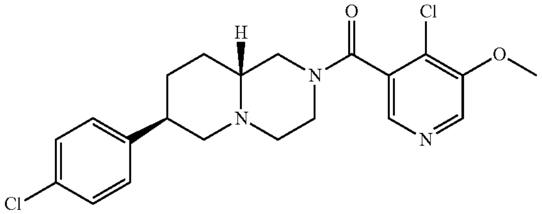
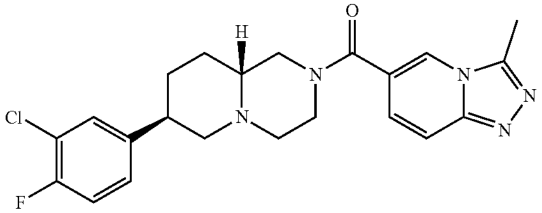
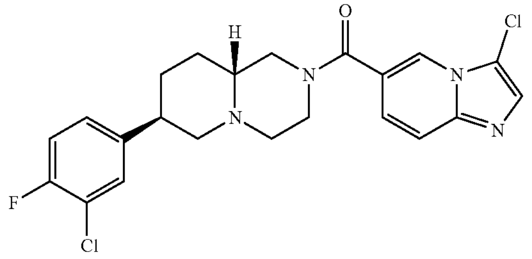
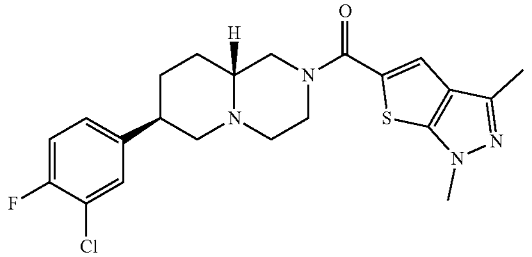
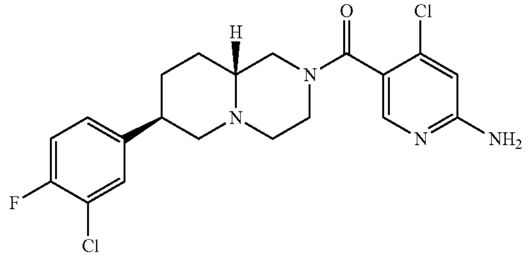
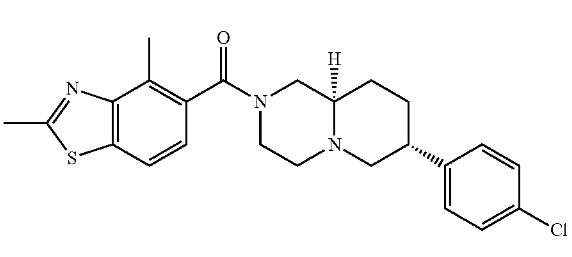
-continued
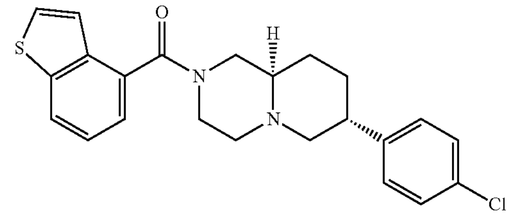
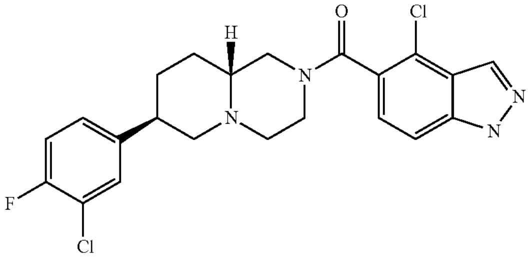
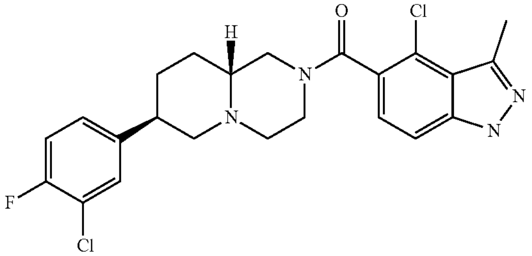
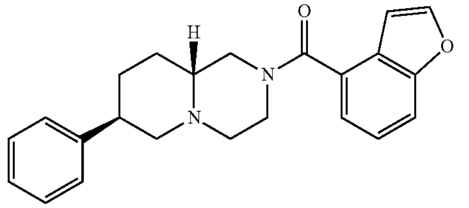
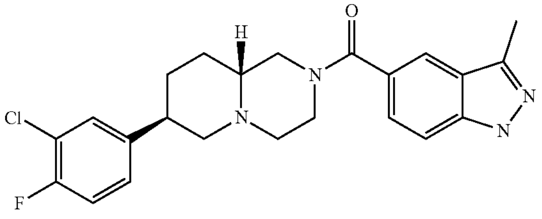
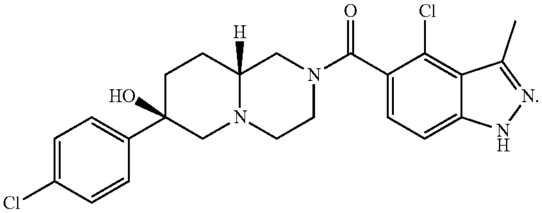
and
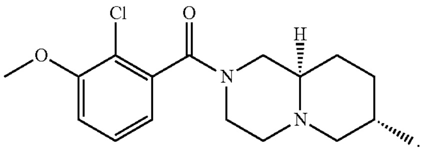
In a preferred embodiment, the present invention provides compounds of formula (I) as described herein, wherein the compounds of formula (I) are of formula (Ia) or (Ib)

(Ia)

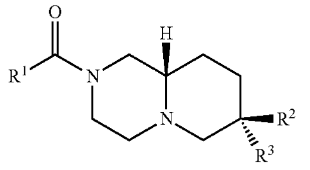

(Ib)

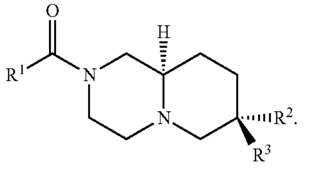

In one embodiment, the present invention provides compounds of formula (I) as described herein, wherein the compounds of formula (I) are of formula (Ic) or (Id)

(Ic)

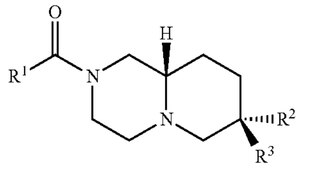

(Id)

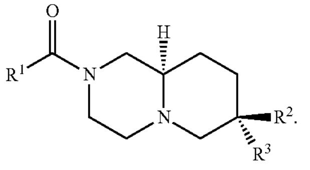

In a particular embodiment, the present invention provides pharmaceutically acceptable salts of the compounds of formula (I) as described herein, especially hydrochloride salts. In a further particular embodiment, the present invention provides compounds according to formula (I) as described herein.

In some embodiments, the compounds of formula (I) are isotopically-labeled by having one or more atoms therein replaced by an atom having a different atomic mass or mass number. Such isotopically-labeled (i.e., radiolabeled) compounds of formula (I) are considered to be within the scope of this disclosure. Examples of isotopes that can be incorporated into the compounds of formula (I) include isotopes of hydrogen, carbon, nitrogen, oxygen, phosphorous, sulfur, fluorine, chlorine, and iodine, such as, but not limited to, $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. Certain isotopically-labeled compounds of formula (I), for example, those incorporating a radioactive isotope, are useful in drug and/or substrate tissue distribution studies. The radioactive isotopes tritium, i.e. $^{3}H$, and carbon-14, i.e., $^{14}C$, are particularly useful for this purpose in view of their ease of incorporation and ready means of detection. For example, a compound of formula (I) can be enriched with 1, 2, 5, 10, 25, 50, 75, 90, 95, or 99 percent of a given isotope.

Substitution with heavier isotopes such as deuterium, i.e. $^{2}H$, may afford certain therapeutic advantages resulting from greater metabolic stability, for example, increased in vivo half-life or reduced dosage requirements.

Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds of formula (I) can generally be prepared by conventional techniques known to those skilled in the art or by processes analogous to those described in the Examples as set out below using an appropriate isotopically-labeled reagent in place of the non-labeled reagent previously employed.

Processes of Manufacturing

The preparation of compounds of formula (I) of the present invention may be carried out in sequential or convergent synthetic routes. Syntheses of the invention are shown in the following general schemes. The skills required for carrying out the reaction and purification of the resulting products are known to those persons skilled in the art. The substituents and indices used in the following description of the processes have the significance given herein, unless indicated to the contrary.

If one of the starting materials, intermediates or compounds of formula (I) contain one or more functional groups which are not stable or are reactive under the reaction conditions of one or more reaction steps, appropriate protective groups (as described e.g., in "Protective Groups in Organic Chemistry" by T. W. Greene and P. G. M. Wutts, 5th Ed., 2014, John Wiley & Sons, N.Y.) can be introduced before the critical step applying methods well known in the art. Such protective groups can be removed at a later stage of the synthesis using standard methods described in the literature.

If starting materials or intermediates contain stereogenic centers, compounds of formula (I) can be obtained as mixtures of diastereomers or enantiomers, which can be separated by methods well known in the art e.g., chiral HPLC, chiral SFC or chiral crystallization. Racemic compounds can e.g., be separated into their antipodes via diastereomeric salts by crystallization with optically pure acids or by separation of the antipodes by specific chromatographic methods using either a chiral adsorbent or a chiral eluent. It is equally possible to separate starting materials and intermediates containing stereogenic centers to afford diastereomerically/enantiomerically enriched starting materials and intermediates. Using such diastereomerically/enantiomerically enriched starting materials and intermediates in the synthesis of compounds of formula (I) will typically lead to the respective diastereomerically/enantiomerically enriched compounds of formula (I).

A person skilled in the art will acknowledge that in the synthesis of compounds of formula (I)—insofar not desired otherwise—an "orthogonal protection group strategy" will be applied, allowing the cleavage of several protective groups one at a time each without affecting other protective groups in the molecule. The principle of orthogonal protection is well known in the art and has also been described in literature (e.g. Barany and R. B. Merrifield, *J. Am. Chem. Soc.* 1977, 99, 7363; H. Waldmann et al., *Angew. Chem. Int. Ed. Engl.* 1996, 35, 2056).

A person skilled in the art will acknowledge that the sequence of reactions may be varied depending on reactivity and nature of the intermediates.

In more detail, the compounds of formula (I) can be manufactured by the methods given below, by the methods given in the examples or by analogous methods. Appropriate reaction conditions for the individual reaction steps are known to a person skilled in the art. Also, for reaction conditions described in literature affecting the described reactions see for example: *Comprehensive Organic Trans-*

*formations: A Guide to Functional Group Preparations,* 2nd Edition, Richard C. Larock. John Wiley & Sons, New York, N.Y. 1999). It was found convenient to carry out the reactions in the presence or absence of a solvent. There is no particular restriction on the nature of the solvent to be employed, provided that it has no adverse effect on the reaction or the reagents involved and that it can dissolve the reagents, at least to some extent. The described reactions can take place over a wide range of temperatures, and the precise reaction temperature is not critical to the invention. It is convenient to carry out the described reactions in a temperature range between −78° C. to reflux. The time required for the reaction may also vary widely, depending on many factors, notably the reaction temperature and the nature of the reagents. However, a period of from 0.5 hours to several days will usually suffice to yield the described intermediates and compounds. The reaction sequence is not limited to the one displayed in the schemes, however, depending on the starting materials and their respective reactivity, the sequence of reaction steps can be freely altered.

If starting materials or intermediates are not commercially available or their synthesis not described in literature, they can be prepared in analogy to existing procedures for close analogues or as outlined in the experimental section.

Compounds of formula (I) wherein $R^1$, $R^2$, and $R^3$ are as defined herein, in particular wherein $R^3$ is hydroxy, alkoxy or halogen, more particularly hydroxy, methoxy or F, may be synthesized according to the general procedure outlined in Scheme 1.

Scheme 1

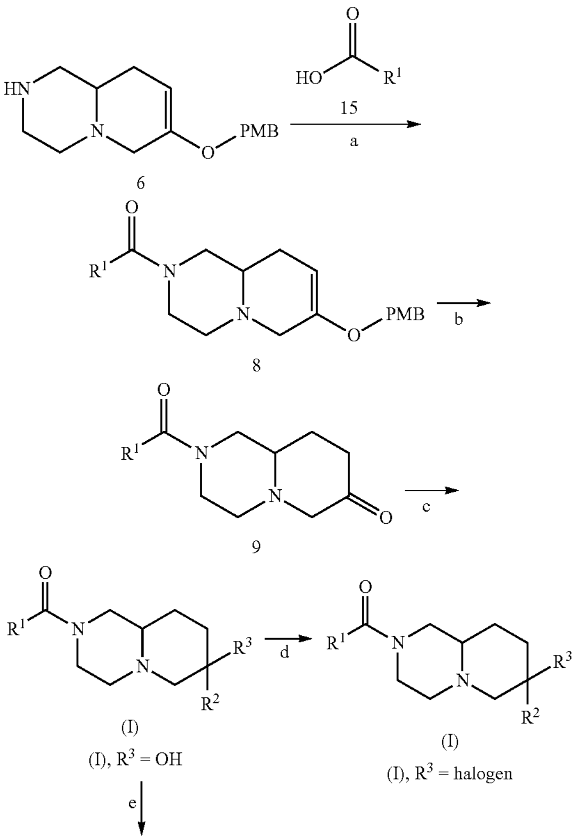

6
8
9
(I)
(I), $R^3$ = OH
(I)
(I), $R^3$ = halogen

-continued

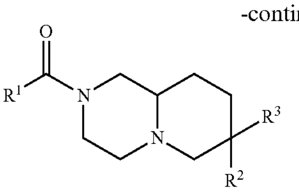

(I)

(I), $R^3$ = OMe

Accordingly, the PMB protected secondary amine 6 (obtainable e.g. by the general procedure outlined in Scheme 3), can be acylated with a suitable carboxylic acid 15 using coupling reagents such as, DCC, HATU, EDCI, HOBt or TBTU, preferably $T_3P$ and a base like Huenig's base, triethyl amine or DMAP in a suitable solvent like N,N-dimethylformamide, DMA, DCM or dioxane, preferably between 0° C. and 50° C. to afford the corresponding intermediate 8 (Scheme 1, step a). Removal of the PMB protective group using acidic conditions, such as treatment with neat AcOH, TfOH, MsOH, TsOH, or preferably TFA in a solvent like toluene or DCM, optionally in the presence of anisole or 1,3 dimethoxybenzene, preferably in DCM and in a temperature range between room temperature and the boiling point of the reaction mixture, preferably at room temperature gives the ketone compound 9 (see e.g. intermediate I-5, step b). Treatment of ketone intermediates 9 with a phenyl or an alkyl Grignard reagent or with trimethyl (trifluoromethyl)silane and TBAF reagents in a solvent like diethylether or THF, preferably THF eventually in presence of a Lewis acid such as LiCl, $MgCl_2$, $AlCl_3$, preferably $CeCl_3$ and in a temperature range between −78° C. and 25° C., preferably at 0° C. affords the corresponding compound of formula (I), wherein $R^1$ and $R^2$ are as defined herein, and wherein $R^3$ is hydroxy (step c). Alternatively, treatment of a suitable heteroaryl bromide reagent, such as 2-bromo-5-(trifluoromethyl)pyridine, with a n-BuLi solution in hexanes in a solvent like diethylether, THF, toluene or a mixture thereof, preferably toluene and in a temperature range between −78° C. and 25° C., preferably at −78° C. in presence of the ketone intermediate 9 affords the corresponding compound of formula (I), wherein $R^1$ and $R^2$ are as defined herein and wherein $R^3$ is hydroxy (step c). The tertiary alcohol moiety of (I) may be further transformed to a halogen, preferably to F, using conditions known in the art (e.g. by reacting (I) with HCl, HBr, HI, $POCl_3$, $SOCl_2$ or $PBr_3$ or with a suitable amino sulfurane reagent such as DAST or by first converting the alcohol of (I) to a sulfonate ester, such as mesylate, in the first stage, followed by reacting said sulfonate ester with e.g. NaF), to yield compound of formula (I), wherein $R^1$ and $R^2$ are as defined herein and wherein $R^3$ is halogen (Scheme 1, step d). In addition, compounds of formula (I) wherein $R^3$ is one halogen may be transformed to compounds of formula (I) wherein $R^3$ is another halogen by methods known in the art. The tertiary alcohol moiety of (I) may be further transformed to an alkoxy, preferably to methoxy, by treatment with an appropriate base, such as NaH, KH, NaHMDS, LiHMDS or LDA, preferably with NaH in a solvent like DMF, THF, dioxane, or a mixture thereof, preferably DMF and in a temperature range between −78° C. and room temperature, preferably at 0° C., followed by addition of an electrophile, e.g. an alkyl or cycloalkyl halide, such as MeI, EtI, iPrI or CyPrI to give the corresponding compound of formula (I), wherein $R^1$ and $R^2$ are as defined herein and wherein $R^3$ is methoxy (Scheme 1, step e).

Alternatively, compounds of formula (I) wherein $R^1$, $R^2$, and $R^3$ are as defined herein, in particular wherein $R^3$ is hydroxy, halogen or alkoxy, more particularly hydroxy, F or methoxy, may be synthesized according to the general procedure outlined in Scheme 2a.

Scheme 2a

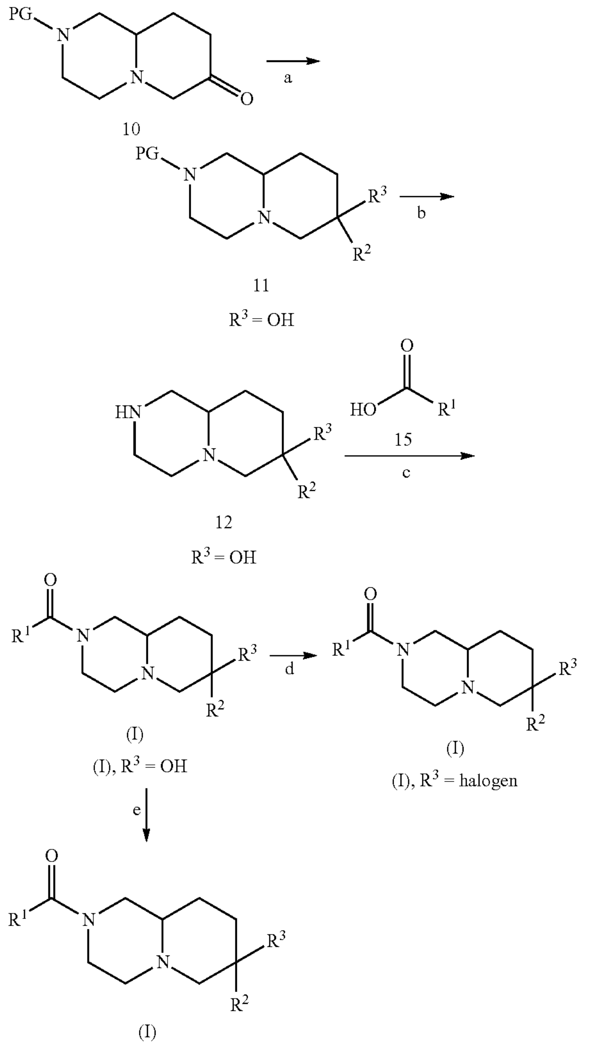

10

11

$R^3$ = OH

12

$R^3$ = OH (I)

(I), $R^3$ = OH (I)

(I), $R^3$ = halogen (I)

(I), $R^3$ = OMe

Accordingly, treatment of protected ketone intermediate 10 (obtainable e.g. by the general procedure outlined in Scheme 3), wherein PG is a protective group, such as Boc (see e.g. intermediate I-1) with a phenyl or an alkyl Grignard reagent or with trimethyl(trifluoromethyl)silane and TBAF reagents in a solvent like diethylether or THF, preferably THF eventually in presence of a Lewis acid such as LiCl, $MgCl_2$, $AlCl_3$, preferably $CeCl_3$ and in a temperature range between −78° C. and 25° C., preferably at 0° C. affords the corresponding intermediate 11, wherein $R^1$ and $R^2$ are as defined herein and wherein $R^3$ is hydroxy (Scheme 2a, step a). Alternatively, treatment of a suitable heteroaryl bromide reagent, such as 2-bromo-5-(trifluoromethyl)pyridine (see e.g. intermediate I-4A) or 5-bromo-2-(trifluoromethyl)pyridine, with a n-BuLi solution in hexanes in a solvent like diethylether, THF, toluene or a mixture thereof, preferably toluene and in a temperature range between −78° C. and 25° C., preferably at −78° C. in presence of the protected ketone intermediate 10 affords the corresponding intermediate 11, wherein $R^1$ and $R^2$ are as defined herein and wherein $R^3$ is hydroxy (Scheme 2a, step a). Removal of the BOC protective group under suitable conditions, e.g. using acidic conditions, such as treatment with HCl in a solvent like EtOAc or MeOH or treatment with TFA in DCM, preferably at around room temperature affords the amine intermediates 12 (step b, see e.g. intermediate I-2A). Subsequent, amide coupling reaction with carboxylic acid compounds 15, wherein $R^1$ is as defined herein, can be accomplished by using coupling reagents such as DCC, EDCI, HOBt, TBTU, $T_3P$, preferably HATU and a base like Huenig's base, triethyl amine or DMAP in a suitable solvent solvent like N,N-dimethylformamide, DMA, DCM or dioxane, preferably between 0° C. and room temperature gives compounds of formula (I) (Scheme 2a, step c). The tertiary alcohol moiety of (I) may be further transformed to a halogen, preferably to F, using conditions known in the art (e.g. by reacting (I) with HCl, HBr, HI, $POCl_3$, $SOCl_2$ or $PBr_3$ or with a suitable amino sulfurane reagent such as DAST or by first converting the alcohol of (I) to a sulfonate ester, such as mesylate, in the first stage, followed by reacting said sulfonate ester with e.g. NaF), to yield compound of formula (I), wherein $R^1$ and $R^2$ are as defined herein and wherein $R^3$ is halogen (Scheme 2a, step d). In addition, compounds of formula (I) wherein $R^3$ is one halogen may be transformed to compounds of formula (I) wherein $R^3$ is another halogen by methods known in the art. The tertiary alcohol moiety of (I) may be further transformed to an alkoxy, preferably to methoxy, by treatment with an appropriate base, such as NaH, KH, NaHMDS, LiHMDS or LDA, preferably with NaH in a solvent like DMF, THF, dioxane, or a mixture thereof, preferably DMF and in a temperature range between −78° C. and room temperature, preferably at 0° C., followed by addition of an electrophile, e.g. an alkyl or cycloalkyl halide, such as MeI to give the corresponding compound of formula (I), wherein $R^1$ and $R^2$ are as defined herein and wherein $R^3$ is methoxy (Scheme 2a, step e).

Alternatively, compounds of formula (I) wherein $R^1$, $R^2$, and $R^3$ are as defined herein, in particular wherein $R^3$ is hydrogen, may be synthesized according to the general procedure outlined in Scheme 2b.

Scheme 2b

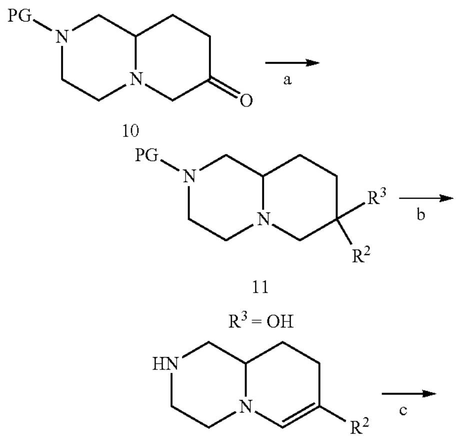

10

11

$R^3$ = OH

13

-continued

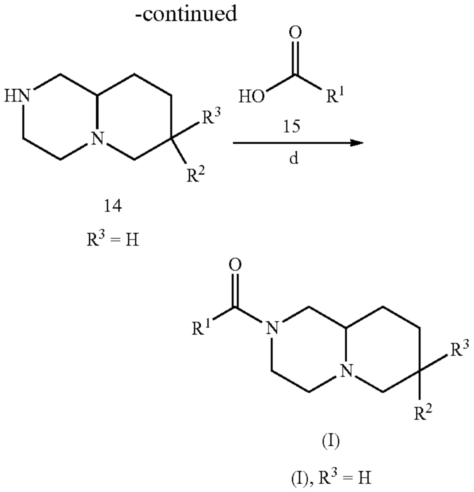

14

$R^3$ = H (I)

(I), $R^3$ = H

Treatment of protected ketone intermediates 10 (obtainable e.g. by the general procedure outlined in Scheme 3), wherein PG is a protective group, such as Boc (see e.g. intermediate I-1) with a phenyl or an alkyl Grignard reagent in a solvent like diethylether or THF, preferably THF eventually in presence of a Lewis acid such as LiCl, $MgCl_2$, $AlCl_3$, preferably $CeCl_3$ and in a temperature range between −78° C. and 25° C., preferably at 0° C. affords the corresponding intermediate 11, wherein $R^1$ and $R^2$ are as defined herein and wherein $R^3$ is hydroxy (Scheme 2b, step a). Alternatively, treatment of a suitable heteroaryl bromide reagent, such as 2-bromo-5-(trifluoromethyl)pyridine (see e.g. intermediate I-4A), with a n-BuLi solution in hexanes in a solvent like diethylether, THF, toluene or a mixture thereof, preferably toluene and in a temperature range between −78° C. and 25° C., preferably at −78° C. in presence of the protected ketone intermediate 10 affords the corresponding intermediate 11, wherein $R^1$ and $R^2$ are as defined herein and wherein $R^3$ is hydroxy (Scheme 2b, step a).

Following dehydration reaction of the hydroxy intermediate with concomitant cleavage of the protective group PG, in presence of an acid such as HCl, TsOH or MsOH, preferably MsOH in a solvent like DCM, MeOH, EtOH, toluene or a mixture thereof, preferably in DCM and in a temperature range between 0° C. and the boiling point of the solvent, preferably at room temperature, gives the enamine intermediates 13 (Scheme 2b, step b). Subsequent heterogeneous catalytic hydrogenation of the alkene using a transition metal catalyst such as $PtO_2$ or Pd/C in presence of MgO, preferably $PtO_2$ in a solvent like THF, MeOH, EtOH, EtOAc, preferably THF in presence of AcOH at around room temperature and under 4 bars pressure of hydrogen, gives the amine intermediates 14 (Scheme 2b, step c, see e.g. intermediate I-6). Finally, amide coupling reaction with carboxylic acid compounds 15, wherein $R^1$ is as defined herein, can be accomplished by using coupling reagents such as DCC, EDCI, HOBt, TBTU, $T_3P$, preferably HATU and a base like Huenig's base, triethyl amine or DMAP in a suitable solvent solvent like N,N-dimethylformamide, DMA, DCM or dioxane, preferably between 0° C. and room temperature gives compounds of formula (I) (step d).

Intermediates 6 and 10 may be synthesized by a variety of conditions, which may be exemplified by the general procedure outlined in Scheme 3.

Scheme 3

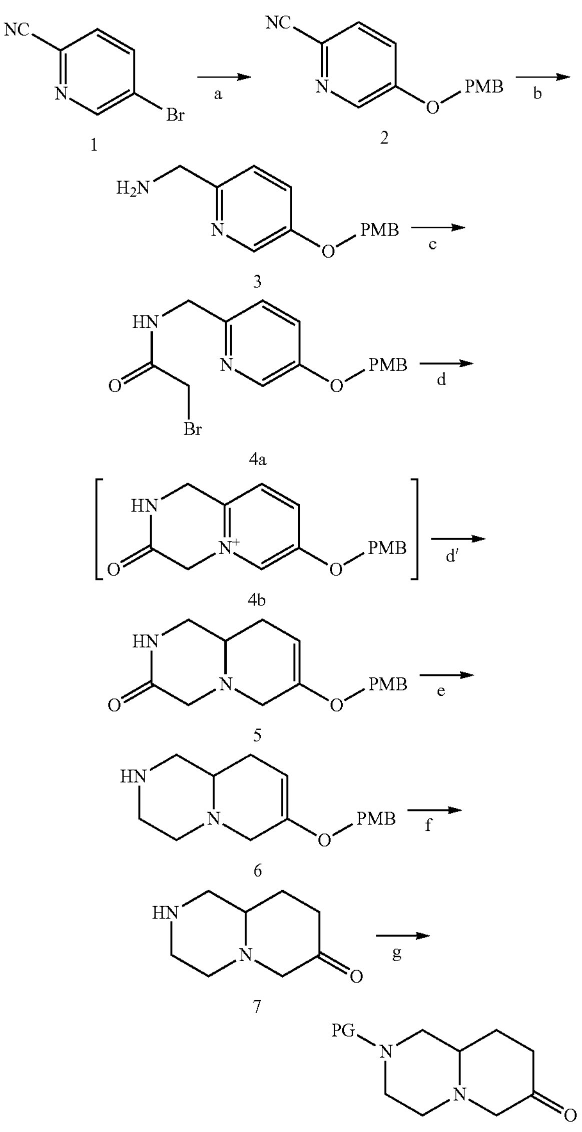

1 2 3 4a 4b 5 6 7 10

Starting from commercially available 3-bromo-6-pyridinecarbonitrile (1), a nucleophilic aromatic substitution reaction can be performed using 4-methoxybenzyl alcohol in presence of a suitable base, such as NaOH, KOH, KH, preferably with NaH in a solvent like DMF, THF, dioxane, or a mixture thereof, preferably in a mixture of DMF and THF and in a temperature range preferably between 0° C. and room temperature, to give the corresponding PMB protected compound 2 (Scheme 3, step a). Reduction of the nitrile group can be achieved using a suitable reducing agent such as borane, lithium borohydride or lithium aluminium hydride in a solvent like ether, DME, THF or a mixture thereof and in a temperature range between 0° C. and the boiling point of the solvent, or preferably using catalytic hydrogenation conditions such as Raney Nickel in a solvent like MeOH in presence of ammonium hydroxide around 50° C. and under 3.5 bar of hydrogen atmosphere, to give the corresponding amine 3 (Scheme 3, step b). Following, amide coupling reaction with bromoacetic acid using a suitable coupling agent such as DCC, DCI or preferably EDCI in a solvent like DCM, THF, DMF, DCE or $CH_3CN$, preferably DCM and in a temperature range between 0° C. and the boiling point of the solvent, preferably at room temperature gives the amide compound 4a (Scheme 3, step c). Subsequent heating of intermediate 4a in a solvent like EtOH, MeOH, preferably $CH_3CN$ and preferably around 50° C. gives the pyridinium intermediate 4b (Scheme 3, step d). Following treatment with a suitable reducing agent, such as sodium borohydride in a solvent like MeOH, preferably at around round temperature gives the lactam compound 5 (Scheme 3, step d'). Reduction of the amide using a suitable reducing agent such as borane, lithium borohydride or preferably lithium aluminium hydride in a solvent like ether, DME or a mixture thereof, preferably THF and in a temperature range between 0° C. and the boiling point of the reaction mixture, preferably at reflux, gives the corresponding amine compound 6 (Scheme 3, step e). Following removal of the PMB protective group using acidic conditions, such as treatment with neat AcOH, TfOH, MsOH, TsOH, or preferably TFA in a solvent like toluene or DCM, optionally in the presence of anisole or 1,3 dimethoxybenzene, preferably in DCM and in a temperature range between room temperature and the boiling point of the reaction mixture, preferably at room temperature gives the ketone compound 7 (Scheme 3, step f). Finally, the secondary amine in 7 is protected with a suitable protective group (Scheme 3, step g) to afford intermediate 10. Thus, for example, treatment with di-tert-butyldicarbonate optionally in presence of a base such as DMAP, TEA, $NaHCO_3$ or preferably $Na_2CO_3$ in a suitable solvent like $CH_3CN$, DCM, dioxane or THF, preferably in $CH_3CN$ and in a temperature range between 0° C. and room temperature, preferably at room temperature yields the Boc protected ketone intermediate I-1.

In one embodiment, carboxylic acid compound 15 is an intermediate of type A, B or C. Intermediates of type A, B, and C can be prepared e.g., as exemplified by the synthetic procedures outlined in Scheme 4.

Scheme 4

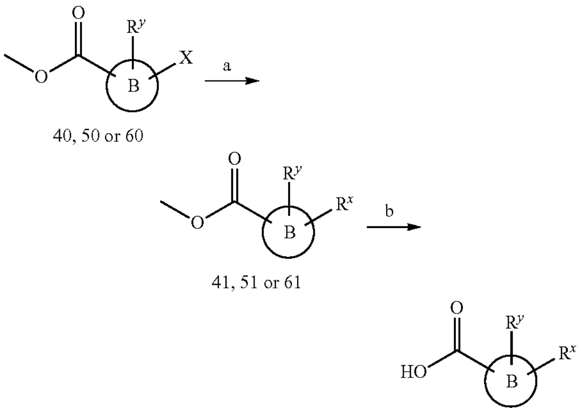

40, 50 or 60

41, 51 or 61

A, B or C

Ester compounds 40, wherein B is aryl, in particular phenyl, X is a halogen, preferably bromine, or a triflate, and $R^y$ is halogen or alkoxy, can be transformed to intermediates 41, wherein $R^x$ is an N-bound heterocycle, by applying cross-coupling reactions such as Buchwald-Hartwig cross-coupling. Treatment of intermediates 40 with suitable amines, such as azetidin-3-ol or morpholine, using a suitable catalyst system such as $Pd_2(dba)_3$ or $Pd(OAc)_2$ and Xantphos, Davephos or BINAP in the presence of a base such as $Cs_2CO_3$ or $K_3PO_4$ in an appropriate solvent such as dioxane or toluene at temperatures ranging from room temperature up to the boiling point of the solvent, optionally applying microwave heating, yields ester compounds 41 (Scheme 4, step a).

Alternatively, ester compounds 40, wherein X, B and $R^y$ are as defined above, can be transformed to intermediates 51, wherein $R^x$ is a C-bound heterocycle, by applying Suzuki cross-coupling reactions. Treatment of intermediates 40 with a suitable boronic acid or ester, e.g. heterocyclyl boronic acids or esters such as tert-butyl 3-(4,4,5,5-tetramethyl-1,3,2-dioxaborolan-2-yl)-1H-pyrazole-1-carboxylate or tert-butyl 4-methyl-3-(4,4,5,5-tetramethyl-1,3,2-dioxaborolan-2-yl)-1H-pyrazole-1-carboxylate, using a suitable catalyst (e.g. bis(triphenylphosphine)palladium (II) chloride, dichloro[1,1'-bis(diphenylphosphino)-ferrocene]palladium (II) dichloromethane adduct, tetrakis(triphenylphosphine) palladium(0) or palladium(II)acetate with triphenylphosphine) in an appropriate solvent (e.g. dioxane, DME, water, toluene, DMF or mixtures thereof) and a suitable base (e.g. $Na_2CO_3$, $NaHCO_3$, KF, $K_2CO_3$ or $NEt_3$) at temperatures between room temperature and the boiling point of the reaction mixture, yields ester compounds 51 (Scheme 4, step a).

Ester compounds 50, wherein B is aryl, in particular phenyl, X is a boronic acid or a boronic acid ester and $R^y$ is alkoxy or halogen can be transformed to intermediates 51, wherein $R^x$ is a C-bound heterocycle, by applying Suzuki cross-coupling reactions. Treatment of intermediates 50 with a suitable organic halide or triflate, e.g. with a bromo-substituted heteroaryl, such as 4-bromo-3-fluoro-1H-pyrazole, using a suitable catalyst (e.g. bis(di-tert-butyl(4-dimethylaminophenyl)phosphine)dichloropalladium(II), bis (triphenylphosphine)palladium (II) chloride, dichloro[1,1'-bis(diphenylphosphino)-ferrocene]palladium(II) dichloromethane adduct, tetrakis(triphenylphosphine)palladium(0) or palladium(II)acetate with triphenylphosphine) in an appropriate solvent (e.g. dioxane, DME, water, toluene, DMF or mixtures thereof) and a suitable base (e.g. $Na_2CO_3$, $NaHCO_3$, KF, $K_2CO_3$ or $NEt_3$) at temperatures between room temperature and the boiling point of the reaction mixture, optionally applying microwave heating, yields ester compounds 51 (Scheme 4, step a).

Ester compounds 60, wherein B is aryl, in particular phenyl, X is a halogen selected from iodine, bromine and chlorine, preferably iodine and $R^y$ is $C_{1-6}$-alkoxy or halogen can be transformed to intermediates 61, wherein $R^x$ is an amide-bound heterocycle is, by applying cross-coupling reactions such as the Ullmann cross-coupling. Treatment of intermediates 60 with a suitable building block bearing an amide motif, e.g. cyclic ureas or carbamates such as imidazolidin-2-one or oxazolidin-2-one, using a suitable catalyst system such as copper(I) iodide and N,N'-dimethylethane-1,2-diamine in the presence of a base such as $Cs_2CO_3$ or $K_2CO_3$ in an appropriate solvent such as dioxane or acetonitrile at temperatures ranging from room temperature up to the boiling point of the solvent, yields ester compounds 61 (Scheme 4, step a).

Finally, alkaline hydrolysis of the ester moiety of intermediates 41, 51 or 61 with a suitable base, such as aqueous lithium, sodium or potassium hydroxide, preferably lithium hydroxide, in a solvent like MeOH, EtOH, THF or a mixture thereof and in a temperature range between 0° C. and the boiling point of the reaction mixture, preferably at around room temperature gives intermediates of type A, B or C (Scheme 4, step b).

In one aspect, the present invention provides a process of manufacturing the compounds of formula (I) as described in any one of the schemes disclosed herein.

In a further aspect, the present invention provides a process of manufacturing the compounds of formula (I) as described herein, comprising:

(a) reacting a compound 9, wherein $R^1$ is as defined herein,

9

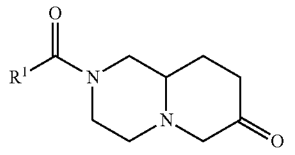

with an organolithium reagent $R^2Li$ or an organomagnesium reagent $R^2MgX$, wherein X is a halogen, to form a tertiary alcohol of formula (I) wherein $R^2$ is as defined herein and $R^3$ is hydroxy; and optionally (b) alkylating the alcohol $R^3$ by treating it with an appropriate base, such as NaH, KH, NaHMDS, LiHMDS or LDA, preferably with NaH, followed by addition of an electrophile, e.g. an alkyl- or cycloalkyl halide, such as MeI, EtI, iPrI or CyPrI to yield the corresponding compound of formula (I), wherein $R^3$ is alkoxy or cycloalkyloxy; or (c) transforming the alcohol $R^3$ into a halogen by reacting the compound of formula (I) wherein $R^3$ is hydroxy with (i) an acid, e.g. HCl, HBr, HI, $POCl_3$, $SOCl_2$ or $PBr_3$; or (ii) with a suitable amino sulfurane reagent such as DAST; or (iii) a sulfonylating reagent such as mesyl chloride, followed by reacting the intermediate sulfonate ester with a halogenide, e.g. NaF to yield the corresponding compound of formula (I), wherein $R^3$ is halogen.

In a further aspect, the present invention provides a process of manufacturing the compounds of formula (I) as described herein, comprising:

(a) reacting an amine 12 or 14, wherein $R^2$ is as defined herein and $R^3$ is hydroxy (12) or hydrogen (14)

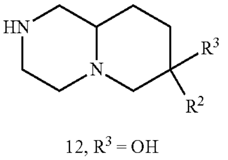

12, $R^3$ = OH
14, $R^3$ = H with a carboxylic acid 15, wherein $R^1$ is as defined herein

15

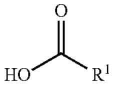

in the presence of a coupling reagent, such as HATU, DCC, EDCI, HOBt, TBTU or $T_3P$, and a base, such as Huenig's base, triethyl amine or DMAP, to afford said compound of formula (I) wherein $R^3$ is hydroxy or hydrogen; and optionally, provided $R^3$ is hydroxy;

(b) alkylating the alcohol $R^3$ by treating it with an appropriate base, such as NaH, KH, NaHMDS, LiHMDS or LDA, preferably with NaH, followed by addition of an electrophile, e.g. an alkyl- or cycloalkyl halide, such as MeI, EtI, iPrI or CyPrI to yield the corresponding compound of formula (I), wherein $R^3$ is alkoxy or cycloalkyloxy; or (c) transforming the alcohol $R^3$ into a halogen by reacting the compound of formula (I) wherein $R^3$ is hydroxy with (i) an acid, e.g. HCl, HBr, HI, $POCl_3$, $SOCl_2$ or $PBr_3$; or (ii) with a suitable amino sulfurane reagent such as DAST; or (iii) a sulfonylating reagent such as mesyl chloride, followed by reacting the intermediate sulfonate ester with a halogenide, e.g. NaF to yield the corresponding compound of formula (I), wherein $R^3$ is halogen.

In yet a further aspect, the present invention provides a compound of formula (I) as described herein, when manufactured according to any one of the processes described herein.

MAGL Inhibitory Activity

Compounds of the present invention are MAGL inhibitors. Thus, in one aspect, the present invention provides the use of compounds of formula (I) as described herein for inhibiting MAGL in a mammal.

In a further aspect, the present invention provides compounds of formula (I) as described herein for use in a method of inhibiting MAGL in a mammal.

In a further aspect, the present invention provides the use of compounds of formula (I) as described herein for the preparation of a medicament for inhibiting MAGL in a mammal.

In a further aspect, the present invention provides a method for inhibiting MAGL in a mammal, which method comprises administering an effective amount of a compound of formula (I) as described herein to the mammal.

Compounds were profiled for MAGL inhibitory activity by determining the enzymatic activity by following the hydrolysis of the natural substrate 2-arachidonoylglycerol (2-AG) resulting in arachidonic acid, which can be followed by mass spectrometry. This assay is hereinafter abbreviated "2-AG assay".

The 2-AG assay was carried out in 384 well assay plates (PP, Greiner Cat #784201) in a total volume of 20 μL. Compound dilutions were made in 100% DMSO (VWR Chemicals 23500.297) in a polypropylene plate in 3-fold dilution steps to give a final concentration range in the assay from 12.5 μM to 0.8 pM. 0.25 μL compound dilutions (100% DMSO) were added to 9 μL MAGL in assay buffer (50 mM TRIS (GIBCO, 15567-027), 1 mM EDTA (Fluka, 03690-100 mL), 0.01% (v/v) Tween. After shaking, the plate was incubated for 15 min at RT. To start the reaction, 10 μL 2-arachidonoylglycerol in assay buffer was added. The final concentrations in the assay was 50 pM MAGL and 8 μM 2-arachidonoylglyerol. After shaking and 30 min incubation at RT, the reaction was quenched by the addition of 40 L of ACN containing 4 μM of d8-arachidonic acid. The amount of arachidonic acid was traced by an online SPE system (Agilent Rapidfire) coupled to a triple quadrupole mass spectrometer (Agilent 6460). A C18 SPE cartridge (G9205A) was used in an ACN/water liquid setup. The mass spectrometer was operated in negative electrospray mode following the mass transitions 303.1→259.1 for arachidonic acid and 311.1→267.0 for d8-arachidonic acid. The activity of the compounds was calculated based on the ratio of intensities [arachidonic acid/d8-arachidonic acid].
TABLE 1
| Example | Systematic Name | IC50 MAGL [nM] |
|---|---|---|
| 1 | 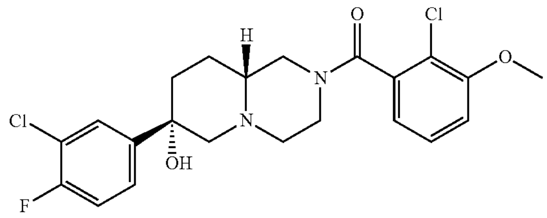 [SMILES: COc1cccc(C(=O)N2CCN3C[C@@](O)(c4ccc(F)c(Cl)c4)CC[C@@H]3C2)c1Cl] | 4.48 |
| 2 | 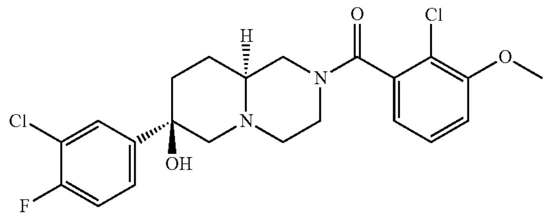 [SMILES: COc1cccc(C(=O)N2CCN3C[C@](O)(c4ccc(F)c(Cl)c4)CC[C@H]3C2)c1Cl] | 18.79 |
| 3 | 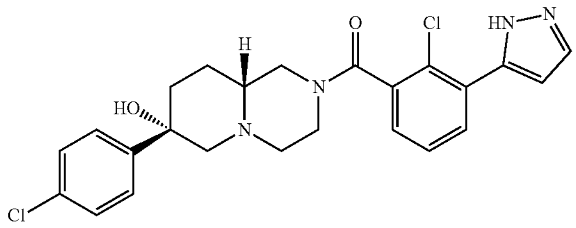 [SMILES: O=C(c1cccc(-c2ccn[nH]2)c1Cl)N1CCN2C[C@@](O)(c3ccc(Cl)cc3)CC[C@@H]2C1] | 4.31 |
| 4 | 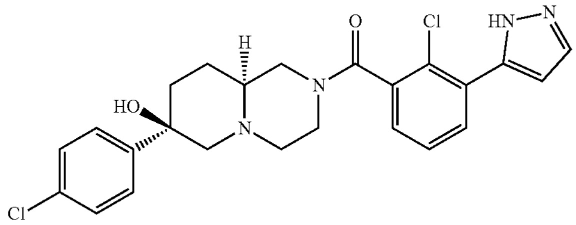 [SMILES: O=C(c1cccc(-c2ccn[nH]2)c1Cl)N1CCN2C[C@](O)(c3ccc(Cl)cc3)CC[C@H]2C1] | 76.33 |
| 5 | 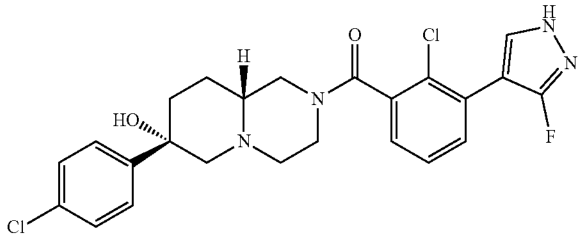 [SMILES: O=C(c1cccc(-c2c[nH]nc2F)c1Cl)N1CCN2C[C@@](O)(c3ccc(Cl)cc3)CC[C@@H]2C1] | 1.95 |
| 6 | 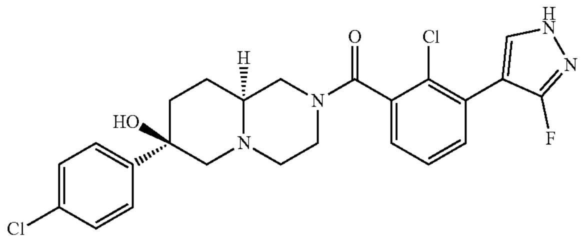 [SMILES: O=C(c1cccc(-c2c[nH]nc2F)c1Cl)N1CCN2C[C@](O)(c3ccc(Cl)cc3)CC[C@H]2C1] | 17.22 |

TABLE 1-continued
| Example | Systematic Name | IC50 MAGL [nM] |
|---|---|---|
| 7 | 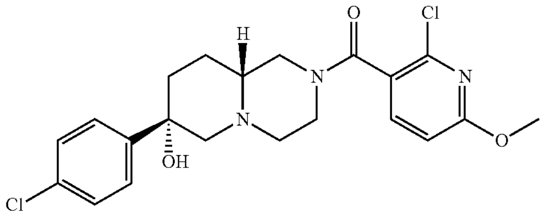 [SMILES: COc1ccc(C(=O)N2CCN3C[C@@](O)(c4ccc(Cl)cc4)CC[C@@H]3C2)c(Cl)n1] | 397.83 |
| 8 | 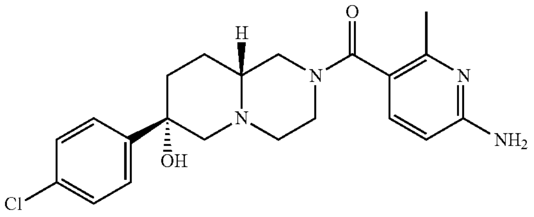 [SMILES: Cc1nc(N)ccc1C(=O)N1CCN2C[C@@](O)(c3ccc(Cl)cc3)CC[C@@H]2C1] | 2956.04 |
| 9 | 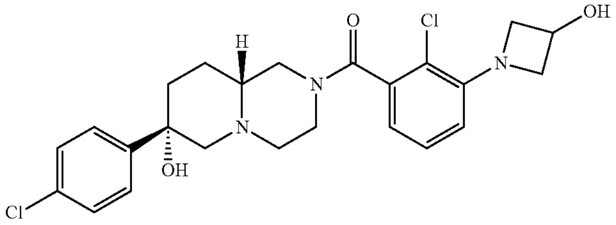 [SMILES: O=C(c1cccc(N2CC(O)C2)c1Cl)N1CCN2C[C@@](O)(c3ccc(Cl)cc3)CC[C@@H]2C1] | 16.21 |
| 10 | 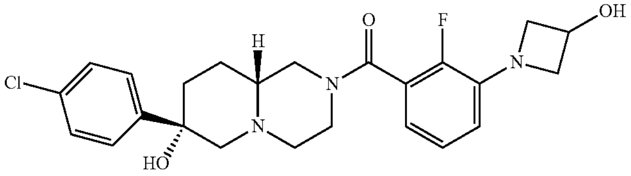 [SMILES: O=C(c1cccc(N2CC(O)C2)c1F)N1CCN2C[C@@](O)(c3ccc(Cl)cc3)CC[C@@H]2C1] | 58.17 |
| 11 | 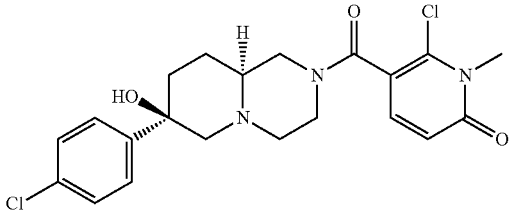 [SMILES: Cn1c(Cl)c(C(=O)N2CCN3C[C@](O)(c4ccc(Cl)cc4)CC[C@H]3C2)ccc1=O] | 775 |
| 12 | 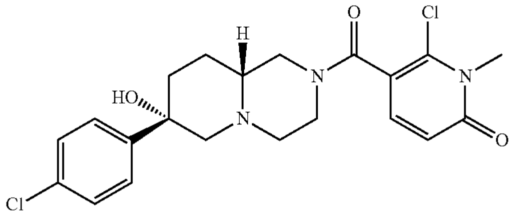 [SMILES: Cn1c(Cl)c(C(=O)N2CCN3C[C@@](O)(c4ccc(Cl)cc4)CC[C@@H]3C2)ccc1=O] | 4457.18 |
| 13 | 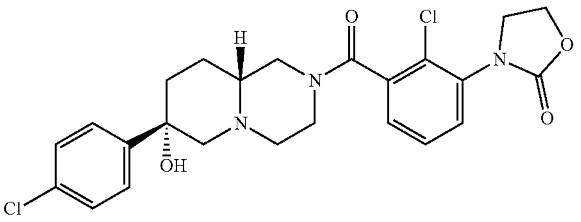 [SMILES: O=C(c1cccc(N2CCOC2=O)c1Cl)N1CCN2C[C@@](O)(c3ccc(Cl)cc3)CC[C@@H]2C1] | 1188.31 |

TABLE 1-continued
| Example | Systematic Name | IC50 MAGL [nM] |
| --- | --- | --- |
| 14 | 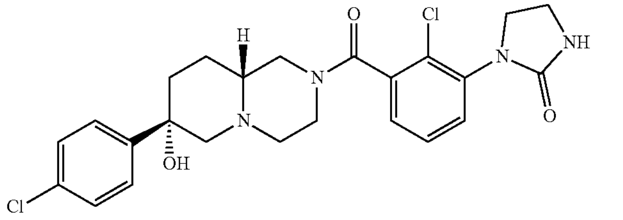 [SMILES: O=C(c1cccc(N2CCNC2=O)c1Cl)N1CCN2C[C@@](O)(c3ccc(Cl)cc3)CC[C@@H]2C1] | 2156.20 |
| 15 | 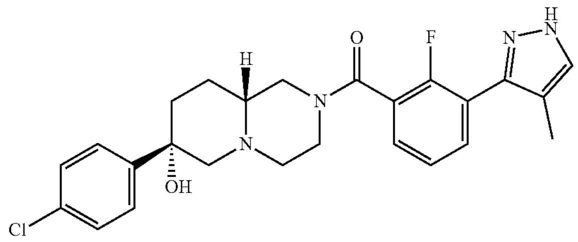 [SMILES: Cc1c[nH]nc1-c1cccc(C(=O)N2CCN3C[C@@](O)(c4ccc(Cl)cc4)CC[C@@H]3C2)c1F] | 168.38 |
| 16 | 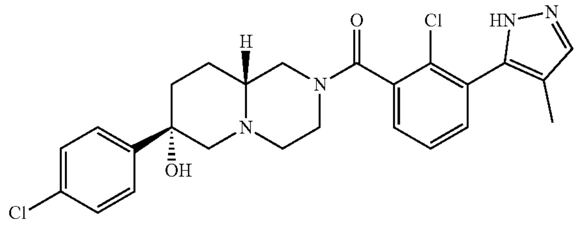 [SMILES: Cc1cn[nH]c1-c1cccc(C(=O)N2CCN3C[C@@](O)(c4ccc(Cl)cc4)CC[C@@H]3C2)c1Cl] | 10.31 |
| 17 | 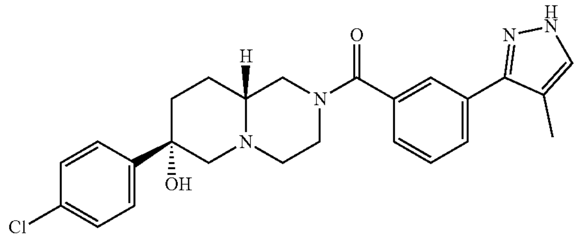 [SMILES: Cc1c[nH]nc1-c1cccc(C(=O)N2CCN3C[C@@](O)(c4ccc(Cl)cc4)CC[C@@H]3C2)c1] | 254.62 |
| 18 | 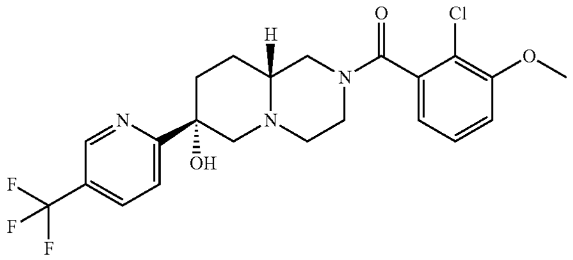 [SMILES: COc1cccc(C(=O)N2CCN3C[C@@](O)(c4ccc(C(F)(F)F)cn4)CC[C@@H]3C2)c1Cl] | 97.19 |
| 19 | 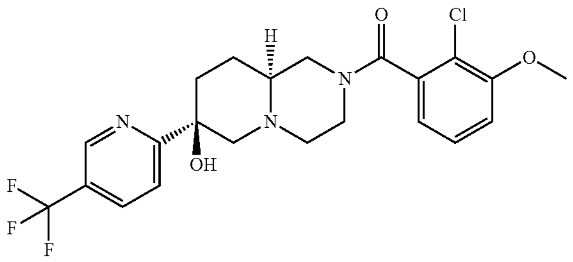 [SMILES: COc1cccc(C(=O)N2CCN3C[C@](O)(c4ccc(C(F)(F)F)cn4)CC[C@H]3C2)c1Cl] | 149.92 |

TABLE 1-continued
| Example | Systematic Name | IC50 MAGL [nM] |
| --- | --- | --- |
| 20 | 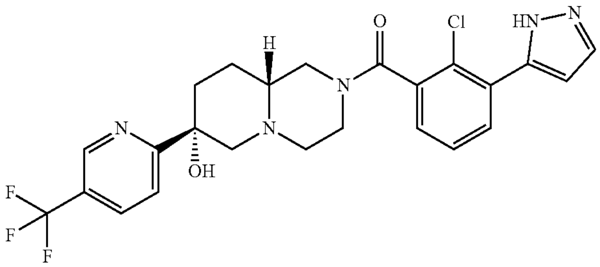 [SMILES: O=C(c1cccc(-c2ccn[nH]2)c1Cl)N1CCN2C[C@@](O)(c3ccc(C(F)(F)F)cn3)CC[C@@H]2C1] | 11.51 |
| 21 | 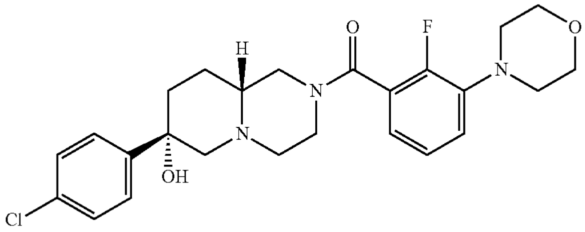 [SMILES: O=C(c1cccc(N2CCOCC2)c1F)N1CCN2C[C@@](O)(c3ccc(Cl)cc3)CC[C@@H]2C1] | 351.34 |
| 22 | 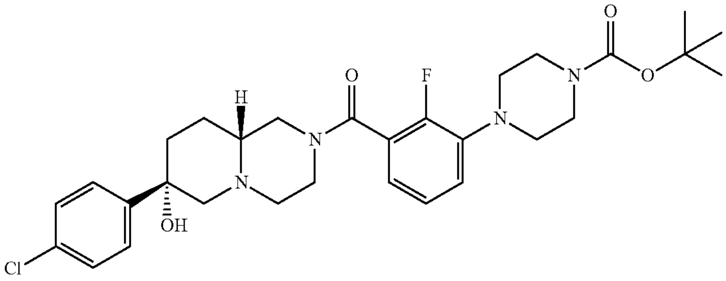 [SMILES: CC(C)(C)OC(=O)N1CCN(c2cccc(C(=O)N3CCN4C[C@@](O)(c5ccc(Cl)cc5)CC[C@@H]4C3)c2F)CC1] | 837.95 |
| 23 | 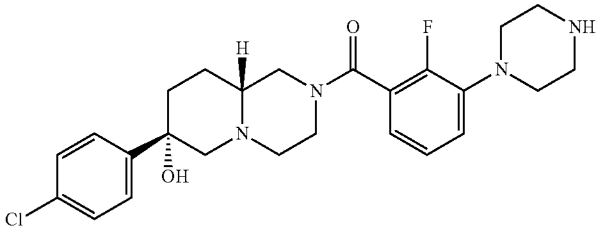 [SMILES: O=C(c1cccc(N2CCNCC2)c1F)N1CCN2C[C@@](O)(c3ccc(Cl)cc3)CC[C@@H]2C1] | 655.9 |
| 24 | 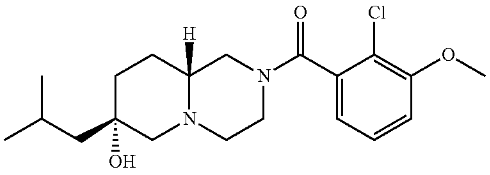 [SMILES: COc1cccc(C(=O)N2CCN3C[C@@](O)(CC(C)C)CC[C@@H]3C2)c1Cl] | 625.52 |
| 25 | 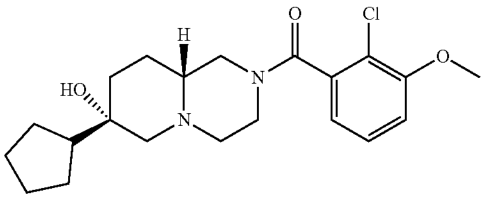 [SMILES: COc1cccc(C(=O)N2CCN3C[C@@](O)(C4CCCC4)CC[C@@H]3C2)c1Cl] | 547.70 |

TABLE 1-continued
| Example | Systematic Name | IC50 MAGL [nM] |
|---|---|---|
| 26 | 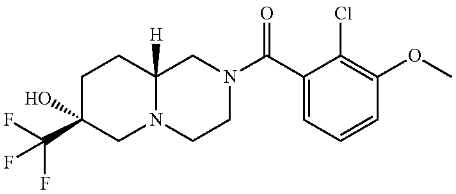 [SMILES: COc1cccc(C(=O)N2CCN3C[C@@](O)(C(F)(F)F)CC[C@@H]3C2)c1Cl] | 677.89 |
| 27 | 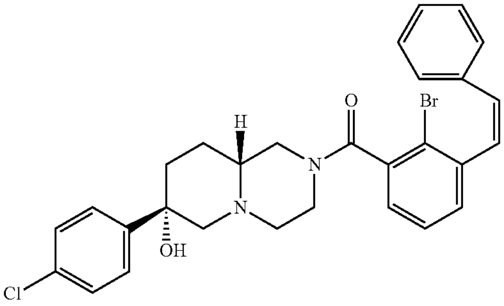 [SMILES: O=C(c1cccc(/C=C\c2ccccc2)c1Br)N1CCN2C[C@@](O)(c3ccc(Cl)cc3)CC[C@@H]2C1] | 10.52 |
| 28 | 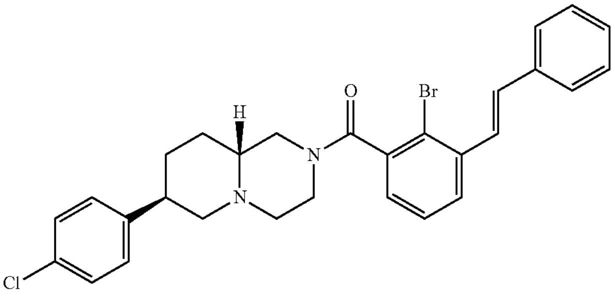 [SMILES: O=C(c1cccc(/C=C/c2ccccc2)c1Br)N1CCN2C[C@@H](c3ccc(Cl)cc3)CC[C@@H]2C1] | 168.76 |
| 29 | 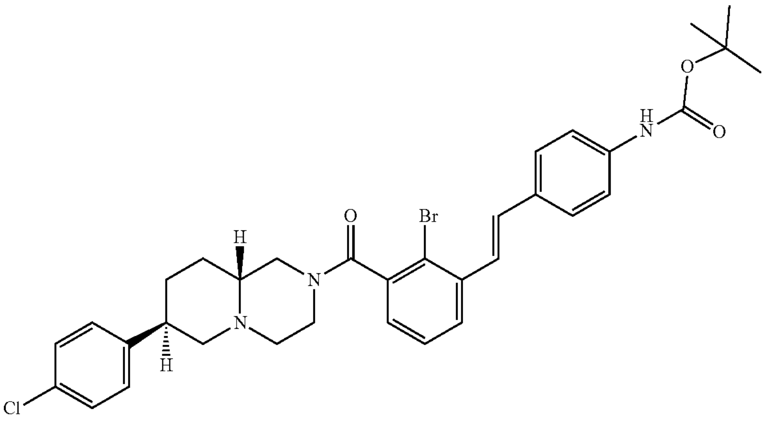 [SMILES: CC(C)(C)OC(=O)Nc1ccc(/C=C/c2cccc(C(=O)N3CCN4C[C@@H](c5ccc(Cl)cc5)CC[C@@H]4C3)c2Br)cc1] | 7.62 |

TABLE 1-continued
| Example | Systematic Name | IC50 MAGL [nM] |
| --- | --- | --- |
| 30 | 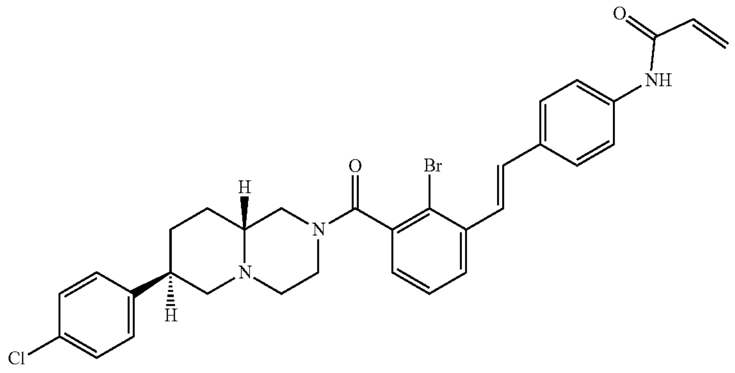 [SMILES: C=CC(=O)Nc1ccc(/C=C/c2cccc(C(=O)N3CCN4C[C@@H](c5ccc(Cl)cc5)CC[C@@H]4C3)c2Br)cc1] | 18.5 |
| 31 | 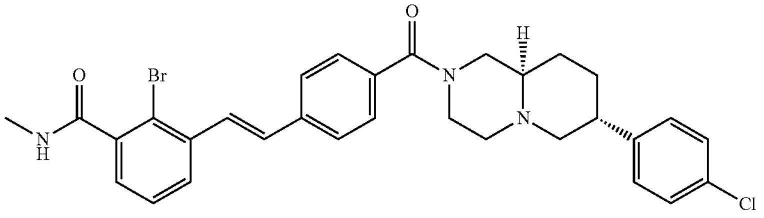 [SMILES: CNC(=O)c1cccc(/C=C/c2ccc(C(=O)N3CCN4C[C@@H](c5ccc(Cl)cc5)CC[C@@H]4C3)cc2)c1Br] | 3.72 |
| 32 | 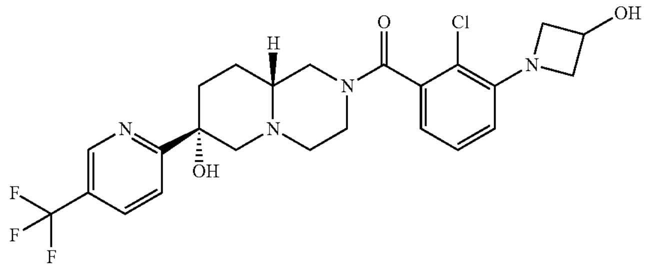 [SMILES: O=C(c1cccc(N2CC(O)C2)c1Cl)N1CCN2C[C@@](O)(c3ccc(C(F)(F)F)cn3)CC[C@@H]2C1] | 72.66 |
| 33 | 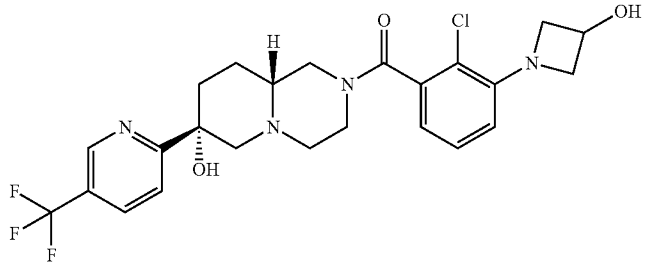 [SMILES: O=C(c1cccc(N2CC(O)C2)c1Cl)N1CCN2C[C@@](O)(c3ccc(C(F)(F)F)cn3)CC[C@@H]2C1] | 158.50 |
| 34 | 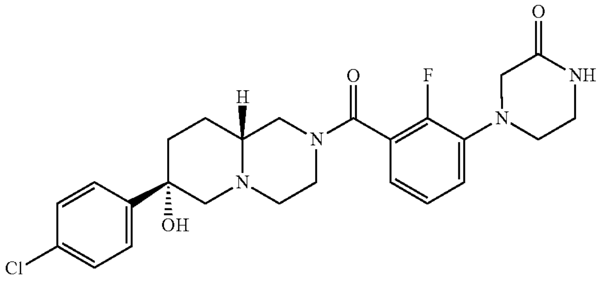 [SMILES: O=C1CN(c2cccc(C(=O)N3CCN4C[C@@](O)(c5ccc(Cl)cc5)CC[C@@H]4C3)c2F)CCN1] | 144.54 |

TABLE 1-continued
| Example | Systematic Name | IC50 MAGL [nM] |
|---|---|---|
| 35 | 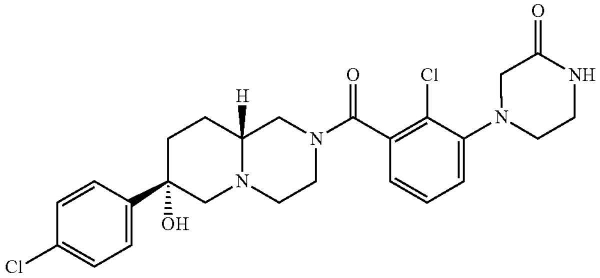 [SMILES: O=C1CN(c2cccc(C(=O)N3CCN4C[C@@](O)(c5ccc(Cl)cc5)CC[C@@H]4C3)c2Cl)CCN1] | 85.97 |
| 36 | 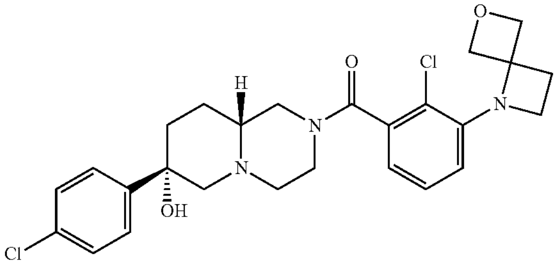 [SMILES: O=C(c1cccc(N2CCC23COC3)c1Cl)N1CCN2C[C@@](O)(c3ccc(Cl)cc3)CC[C@@H]2C1] | 76.01 |
| 37 | 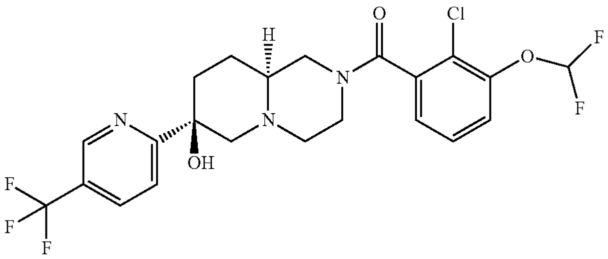 [SMILES: O=C(c1cccc(OC(F)F)c1Cl)N1CCN2C[C@](O)(c3ccc(C(F)(F)F)cn3)CC[C@H]2C1] | 898.09 |
| 38 | 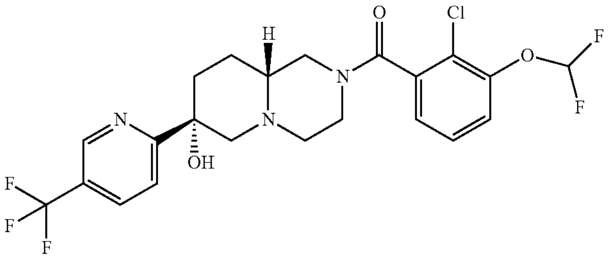 [SMILES: O=C(c1cccc(OC(F)F)c1Cl)N1CCN2C[C@@](O)(c3ccc(C(F)(F)F)cn3)CC[C@@H]2C1] | 327.31 |
| 39 | 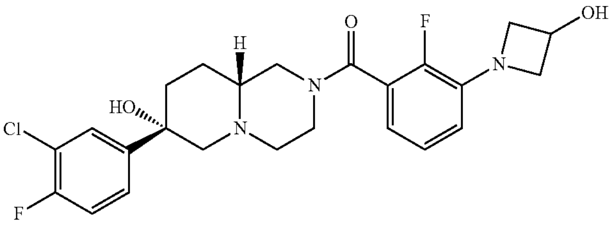 [SMILES: O=C(c1cccc(N2CC(O)C2)c1F)N1CCN2C[C@@](O)(c3ccc(F)c(Cl)c3)CC[C@@H]2C1] | 38.45 |
| 40 | 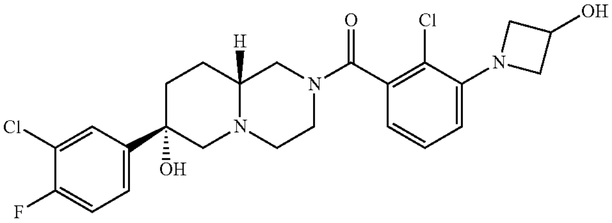 [SMILES: O=C(c1cccc(N2CC(O)C2)c1Cl)N1CCN2C[C@@](O)(c3ccc(F)c(Cl)c3)CC[C@@H]2C1] | 6.91 |

TABLE 1-continued
| Example | Systematic Name | IC50 MAGL [nM] |
|---|---|---|
| 41 | 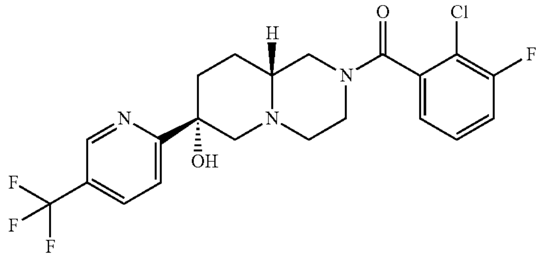 [SMILES: O=C(c1cccc(F)c1Cl)N1CCN2C[C@@](O)(c3ccc(C(F)(F)F)cn3)CC[C@@H]2C1] | 392.46 |
| 42 | 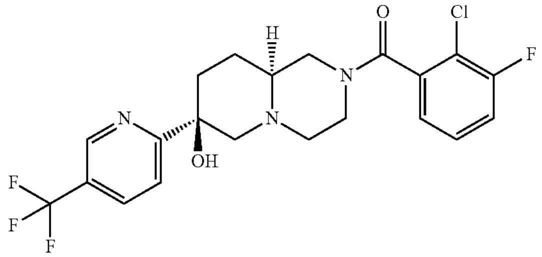 [SMILES: O=C(c1cccc(F)c1Cl)N1CCN2C[C@](O)(c3ccc(C(F)(F)F)cn3)CC[C@H]2C1] | 4818.92 |
| 43 | 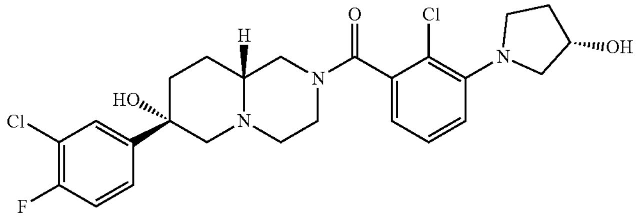 [SMILES: O=C(c1cccc(N2CC[C@H](O)C2)c1Cl)N1CCN2C[C@@](O)(c3ccc(F)c(Cl)c3)CC[C@@H]2C1] | 20.75 |
| 44 | 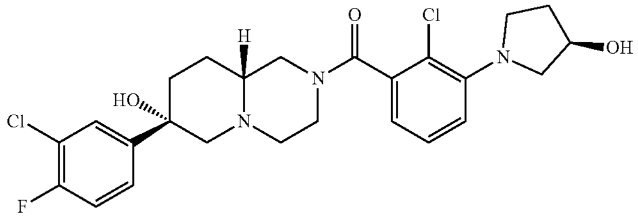 [SMILES: O=C(c1cccc(N2CC[C@@H](O)C2)c1Cl)N1CCN2C[C@@](O)(c3ccc(F)c(Cl)c3)CC[C@@H]2C1] | 15.37 |
| 45 | 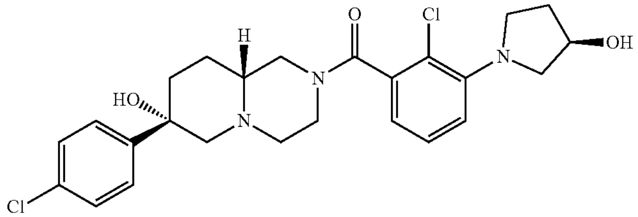 [SMILES: O=C(c1cccc(N2CC[C@@H](O)C2)c1Cl)N1CCN2C[C@@](O)(c3ccc(Cl)cc3)CC[C@@H]2C1] | 66.85 |
| 46 | 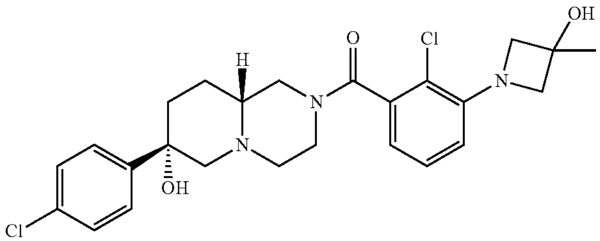 [SMILES: CC1(O)CN(c2cccc(C(=O)N3CCN4C[C@@](O)(c5ccc(Cl)cc5)CC[C@@H]4C3)c2Cl)C1] | 234.03 |

TABLE 1-continued
| Example | Systematic Name | IC50 MAGL [nM] |
|---|---|---|
| 47 | 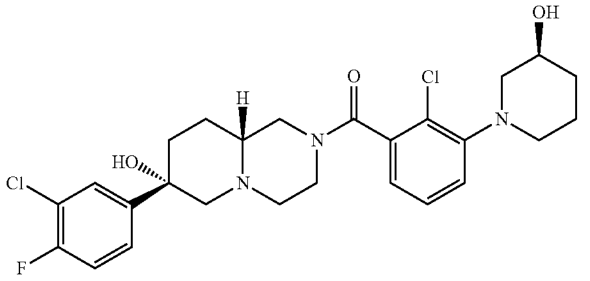 [SMILES: O=C(c1cccc(N2CCC[C@H](O)C2)c1Cl)N1CCN2C[C@@](O)(c3ccc(F)c(Cl)c3)CC[C@@H]2C1] | 41.47 |
| 48 | 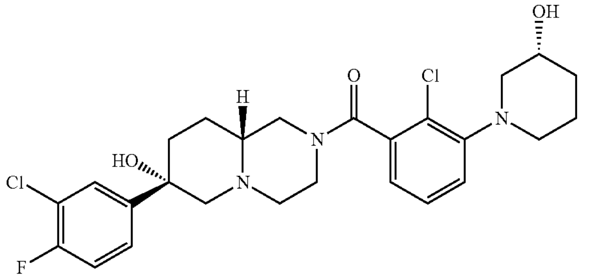 [SMILES: O=C(c1cccc(N2CCC[C@@H](O)C2)c1Cl)N1CCN2C[C@@](O)(c3ccc(F)c(Cl)c3)CC[C@@H]2C1] | 292.05 |
| 49 | 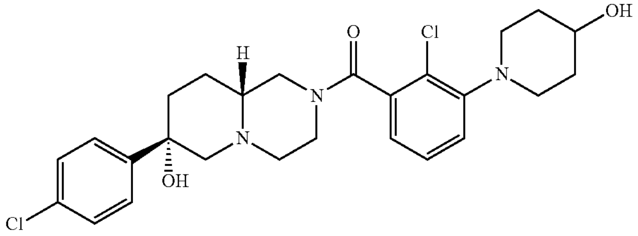 [SMILES: O=C(c1cccc(N2CCC(O)CC2)c1Cl)N1CCN2C[C@@](O)(c3ccc(Cl)cc3)CC[C@@H]2C1] | 80.79 |
| 50 | 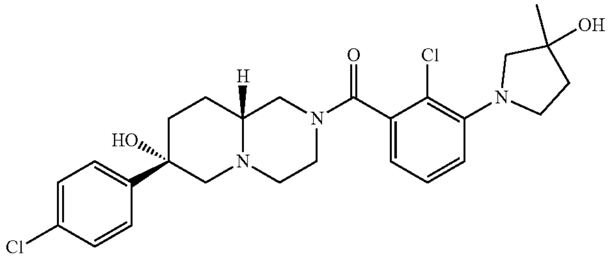 [SMILES: CC1(O)CCN(c2cccc(C(=O)N3CCN4C[C@@](O)(c5ccc(Cl)cc5)CC[C@@H]4C3)c2Cl)C1] | 72.44 |
| 51 | 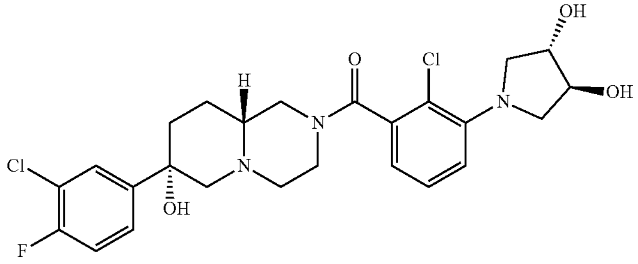 [SMILES: O=C(c1cccc(N2C[C@H](O)[C@@H](O)C2)c1Cl)N1CCN2C[C@@](O)(c3ccc(F)c(Cl)c3)CC[C@@H]2C1] | 10.92 |

TABLE 1-continued
| Example | Systematic Name | IC50 MAGL [nM] |
|---|---|---|
| 52 | 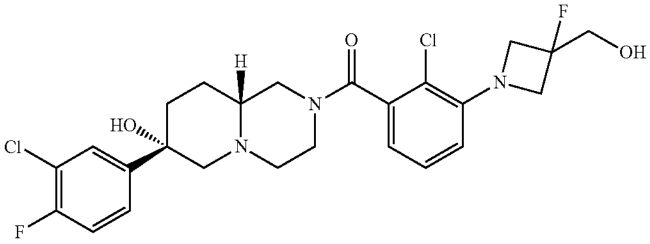 [SMILES: O=C(c1cccc(N2CC(F)(CO)C2)c1Cl)N1CCN2C[C@@](O)(c3ccc(F)c(Cl)c3)CC[C@@H]2C1] | 84.25 |
| 53 | 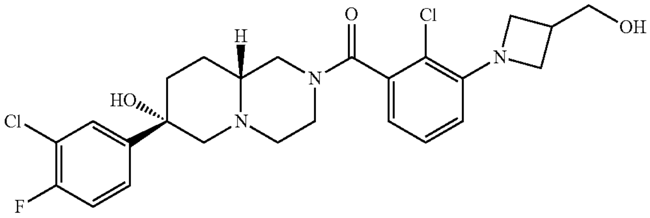 [SMILES: O=C(c1cccc(N2CC(CO)C2)c1Cl)N1CCN2C[C@@](O)(c3ccc(F)c(Cl)c3)CC[C@@H]2C1] | 79.67 |
| 54 | 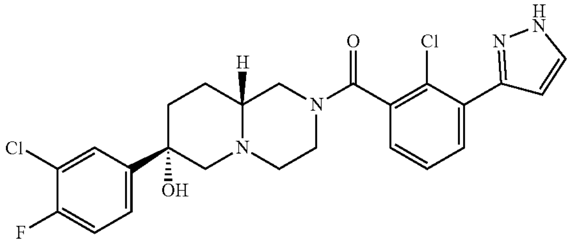 [SMILES: O=C(c1cccc(-c2cc[nH]n2)c1Cl)N1CCN2C[C@@](O)(c3ccc(F)c(Cl)c3)CC[C@@H]2C1] | 3.08 |
| 55 | 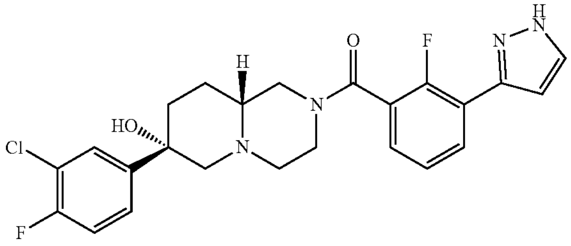 [SMILES: O=C(c1cccc(-c2cc[nH]n2)c1F)N1CCN2C[C@@](O)(c3ccc(F)c(Cl)c3)CC[C@@H]2C1] | 9.04 |
| 56 | 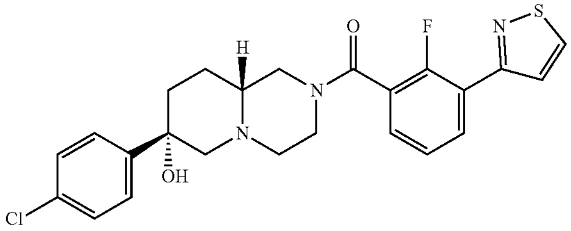 [SMILES: O=C(c1cccc(-c2ccsn2)c1F)N1CCN2C[C@@](O)(c3ccc(Cl)cc3)CC[C@@H]2C1] | 37.47 |
| 57 | 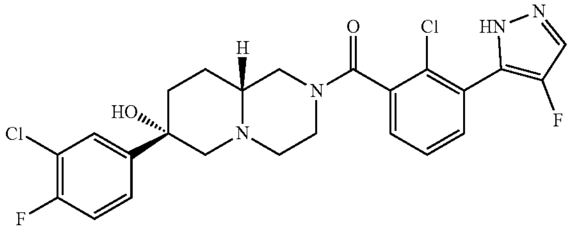 [SMILES: O=C(c1cccc(-c2[nH]ncc2F)c1Cl)N1CCN2C[C@@](O)(c3ccc(F)c(Cl)c3)CC[C@@H]2C1] | 0.74 |

TABLE 1-continued
| Example | Systematic Name | IC50 MAGL [nM] |
|---|---|---|
| 58 | 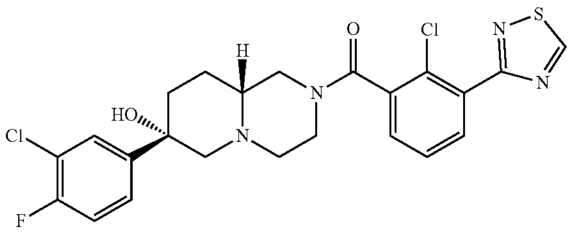 [SMILES: O=C(c1cccc(-c2ncsn2)c1Cl)N1CCN2C[C@@](O)(c3ccc(F)c(Cl)c3)CC[C@@H]2C1] | 14.18 |
| 59 | 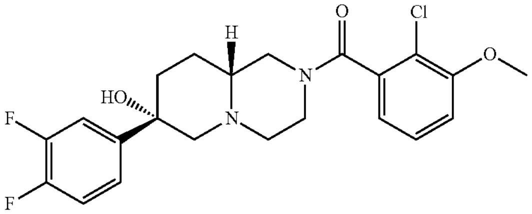 [SMILES: COc1cccc(C(=O)N2CCN3C[C@@](O)(c4ccc(F)c(F)c4)CC[C@@H]3C2)c1Cl] | 11.22 |
| 60 | 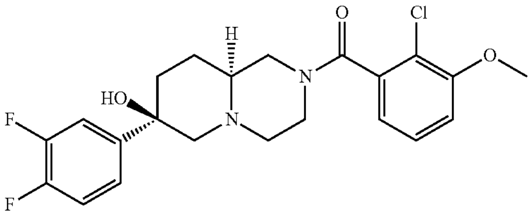 [SMILES: COc1cccc(C(=O)N2CCN3C[C@](O)(c4ccc(F)c(F)c4)CC[C@H]3C2)c1Cl] | 118.17 |
| 61 | 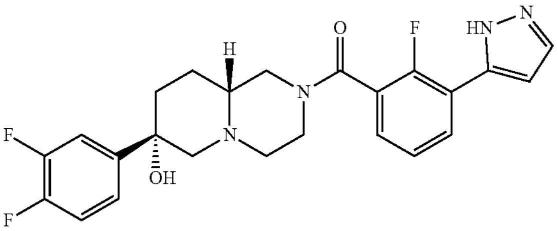 [SMILES: O=C(c1cccc(-c2ccn[nH]2)c1F)N1CCN2C[C@@](O)(c3ccc(F)c(F)c3)CC[C@@H]2C1] | 14.02 |
| 62 | 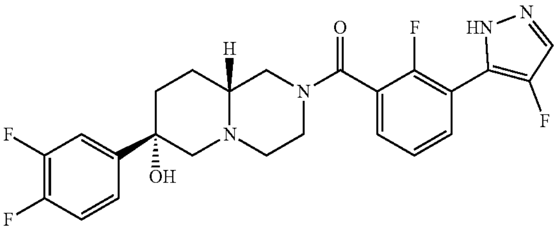 [SMILES: O=C(c1cccc(-c2[nH]ncc2F)c1F)N1CCN2C[C@@](O)(c3ccc(F)c(F)c3)CC[C@@H]2C1] | 20.53 |
| 63 | 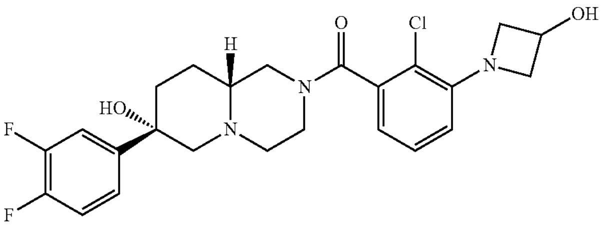 [SMILES: O=C(c1cccc(N2CC(O)C2)c1Cl)N1CCN2C[C@@](O)(c3ccc(F)c(F)c3)CC[C@@H]2C1] | 39.37 |

TABLE 1-continued
| Example | Systematic Name | IC50 MAGL [nM] |
|---|---|---|
| 64 | 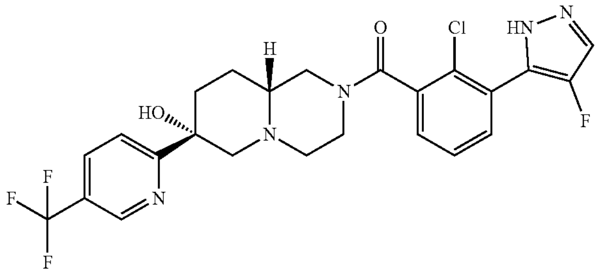 [SMILES: O=C(c1cccc(-c2[nH]ncc2F)c1Cl)N1CCN2C[C@@](O)(c3ccc(C(F)(F)F)cn3)CC[C@@H]2C1] | 13.37 |
| 65 | 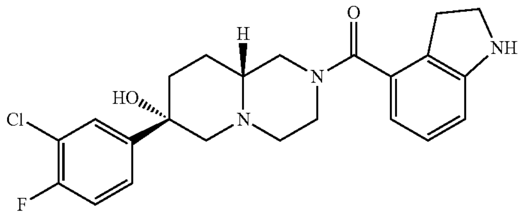 [SMILES: O=C(c1cccc2c1CCN2)N1CCN2C[C@@](O)(c3ccc(F)c(Cl)c3)CC[C@@H]2C1] | 68.44 |
| 66 | 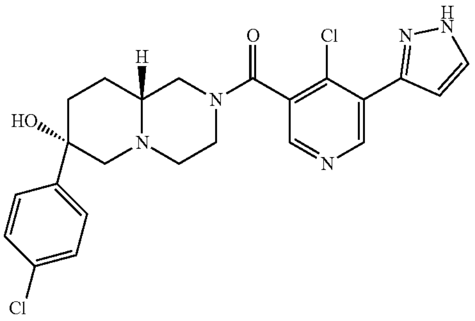 [SMILES: O=C(c1cncc(-c2cc[nH]n2)c1Cl)N1CCN2C[C@@](O)(c3ccc(Cl)cc3)CC[C@@H]2C1] | 172.27 |
| 67 | 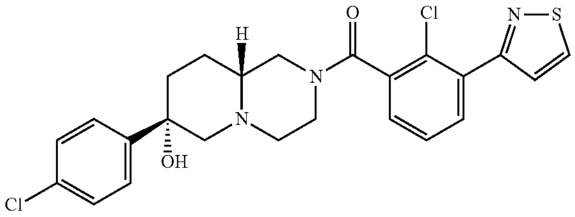 [SMILES: O=C(c1cccc(-c2ccsn2)c1Cl)N1CCN2C[C@@](O)(c3ccc(Cl)cc3)CC[C@@H]2C1] | 14.64 |
| 68 | 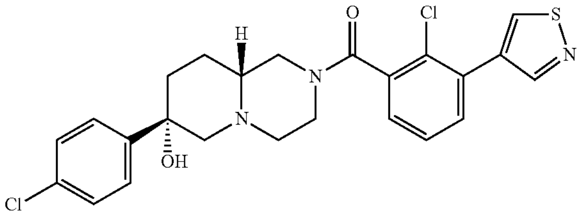 [SMILES: O=C(c1cccc(-c2cnsc2)c1Cl)N1CCN2C[C@@](O)(c3ccc(Cl)cc3)CC[C@@H]2C1] | 82.50 |
| 69 | 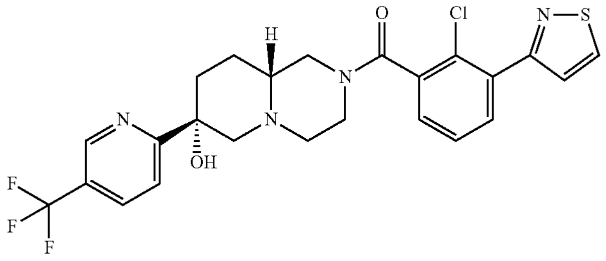 [SMILES: O=C(c1cccc(-c2ccsn2)c1Cl)N1CCN2C[C@@](O)(c3ccc(C(F)(F)F)cn3)CC[C@@H]2C1] | 126.32 |

TABLE 1-continued

| Example | Systematic Name | IC50 MAGL [nM] |
|---|---|---|
| 70 | 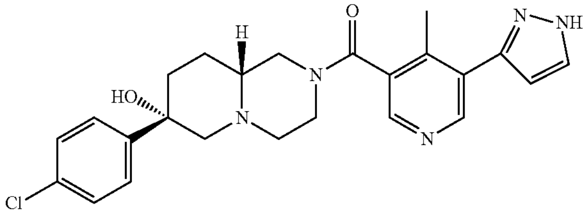 [SMILES: Cc1c(C(=O)N2CCN3C[C@@](O)(c4ccc(Cl)cc4)CC[C@@H]3C2)cncc1-c1cc[nH]n1] | 993.62 |
| 71 | 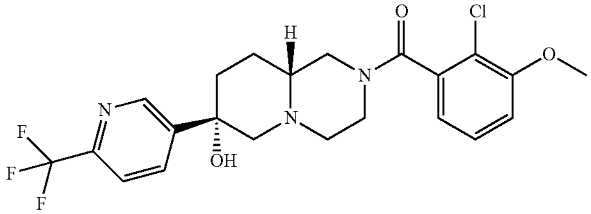 [SMILES: COc1cccc(C(=O)N2CCN3C[C@@](O)(c4ccc(C(F)(F)F)nc4)CC[C@@H]3C2)c1Cl] | 278.30 |
| 72 | 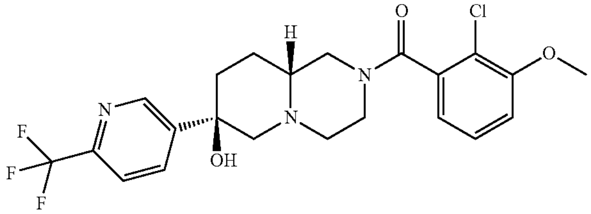 [SMILES: COc1cccc(C(=O)N2CCN3C[C@](O)(c4ccc(C(F)(F)F)nc4)CC[C@@H]3C2)c1Cl] | 3490.44 |

In one aspect, the present invention provides compounds of formula (I) and their pharmaceutically acceptable salts or esters as described herein, wherein said compounds of formula (I) and their pharmaceutically acceptable salts or esters have $IC_{50}$'s for MAGL inhibition below 25 μM, preferably below 10 μM, more preferably below 5 μM as measured in the MAGL assay described herein.

In one embodiment, compounds of formula (I) and their pharmaceutically acceptable salts or esters as described herein have $IC_{50}$ (MAGL inhibition) values between 0.000001 μM and 25 μM, particular compounds have $IC_{50}$ values between 0.000005 μM and 10 μM, further particular compounds have $IC_{50}$ values between 0.00005 μM and 5 μM, as measured in the MAGL assay described herein.

Using the Compounds of the Invention

In one aspect, the present invention provides compounds of formula (I) as described herein, or pharmaceutically acceptable salts thereof, for use as therapeutically active substance.

In a further aspect, the present invention provides the use of compounds of formula (I) as described herein, or of pharmaceutically acceptable salts thereof, for the treatment or prophylaxis of neuroinflammation, neurodegenerative diseases, pain, cancer and/or mental disorders in a mammal.

In one embodiment, the present invention provides the use of compounds of formula (I) as described herein, or of pharmaceutically acceptable salts thereof, for the treatment or prophylaxis of neuroinflammation and/or neurodegenerative diseases in a mammal.

In one embodiment, the present invention provides the use of compounds of formula (I) as described herein, or of pharmaceutically acceptable salts thereof, for the treatment or prophylaxis of neurodegenerative diseases in a mammal.

In one embodiment, the present invention provides the use of compounds of formula (I) as described herein, or of pharmaceutically acceptable salts thereof, for the treatment or prophylaxis of cancer in a mammal.

In one aspect, the present invention provides the use of compounds of formula (I) as described herein, or of pharmaceutically acceptable salts thereof, for the treatment or prophylaxis of multiple sclerosis, Alzheimer's disease, Parkinson's disease, amyotrophic lateral sclerosis, traumatic brain injury, neurotoxicity, stroke, epilepsy, anxiety, migraine, depression, hepatocellular carcinoma, colon carcinogenesis, ovarian cancer, neuropathic pain, chemotherapy induced neuropathy, acute pain, chronic pain and/or spasticity associated with pain in a mammal.

In a preferred embodiment, the present invention provides the use of compounds of formula (I) as described herein, or of pharmaceutically acceptable salts thereof, for the treatment or prophylaxis of multiple sclerosis, Alzheimer's disease and/or Parkinson's disease in a mammal.

In a particularly preferred embodiment, the present invention provides the use of compounds of formula (I) as described herein, or of pharmaceutically acceptable salts thereof, for the treatment or prophylaxis of multiple sclerosis in a mammal.

In one aspect, the present invention provides compounds of formula (I) as described herein, or pharmaceutically acceptable salts thereof, for use in the treatment or prophylaxis of neuroinflammation, neurodegenerative diseases, pain, cancer and/or mental disorders in a mammal.

In one embodiment, the present invention provides compounds of formula (I) as described herein, or pharmaceutically acceptable salts thereof, for use in the treatment or prophylaxis of neuroinflammation and/or neurodegenerative diseases in a mammal.

In one embodiment, the present invention provides compounds of formula (I) as described herein, or pharmaceutically acceptable salts thereof, for use in the treatment or prophylaxis of cancer in a mammal.

In one embodiment, the present invention provides compounds of formula (I) as described herein, or pharmaceutically acceptable salts thereof, for use in the treatment or prophylaxis of neurodegenerative diseases in a mammal.

In one aspect, the present invention provides compounds of formula (I) as described herein, or pharmaceutically acceptable salts thereof, for use in the treatment or prophylaxis of multiple sclerosis, Alzheimer's disease, Parkinson's disease, amyotrophic lateral sclerosis, traumatic brain injury, neurotoxicity, stroke, epilepsy, anxiety, migraine, depression, hepatocellular carcinoma, colon carcinogenesis, ovarian cancer, neuropathic pain, chemotherapy induced neuropathy, acute pain, chronic pain and/or spasticity associated with pain in a mammal.

In a preferred embodiment, the present invention provides compounds of formula (I) as described herein, or pharmaceutically acceptable salts thereof, for use in the treatment or prophylaxis of multiple sclerosis, Alzheimer's disease and/or Parkinson's disease in a mammal.

In a particularly preferred embodiment, the present invention provides compounds of formula (I) as described herein, or pharmaceutically acceptable salts thereof, for use in the treatment or prophylaxis of multiple sclerosis in a mammal.

In one aspect, the present invention provides the use of compounds of formula (I) as described herein, or of pharmaceutically acceptable salts thereof, for the preparation of a medicament for the treatment or prophylaxis of neuroinflammation, neurodegenerative diseases, pain, cancer and/or mental disorders in a mammal.

In one embodiment, the present invention provides the use of compounds of formula (I) as described herein, or of pharmaceutically acceptable salts thereof, for the preparation of a medicament for the treatment or prophylaxis of neuroinflammation and/or neurodegenerative diseases in a mammal.

In one embodiment, the present invention provides the use of compounds of formula (I) as described herein, or of pharmaceutically acceptable salts thereof, for the preparation of a medicament for the treatment or prophylaxis of neurodegenerative diseases in a mammal.

In one embodiment, the present invention provides the use of compounds of formula (I) as described herein, or of pharmaceutically acceptable salts thereof, for the preparation of a medicament for the treatment or prophylaxis of cancer in a mammal.

In a further aspect, the present invention provides the use of compounds of formula (I) as described herein, or of pharmaceutically acceptable salts thereof, for the preparation of a medicament for the treatment or prophylaxis of multiple sclerosis, Alzheimer's disease, Parkinson's disease, amyotrophic lateral sclerosis, traumatic brain injury, neurotoxicity, stroke, epilepsy, anxiety, migraine, depression, hepatocellular carcinoma, colon carcinogenesis, ovarian cancer, neuropathic pain, chemotherapy induced neuropathy, acute pain, chronic pain and/or spasticity associated with pain in a mammal.

In a preferred embodiment, the present invention provides the use of compounds of formula (I) as described herein, or of pharmaceutically acceptable salts thereof, for the preparation of a medicament for the treatment or prophylaxis of multiple sclerosis, Alzheimer's disease and/or Parkinson's disease in a mammal.

In a particularly preferred embodiment, the present invention provides the use of compounds of formula (I) as described herein, or of pharmaceutically acceptable salts thereof, for the preparation of a medicament for the treatment or prophylaxis of multiple sclerosis in a mammal.

In one aspect, the present invention provides a method for the treatment or prophylaxis of neuroinflammation, neurodegenerative diseases, pain, cancer and/or mental disorders in a mammal, which method comprises administering an effective amount of a compound of formula (I) as described herein, or of a pharmaceutically acceptable salt thereof, to the mammal.

In one embodiment, the present invention provides a method for the treatment or prophylaxis of neuroinflammation and/or neurodegenerative diseases in a mammal, which method comprises administering an effective amount of a compound of formula (I) as described herein, or of a pharmaceutically acceptable salt thereof, to the mammal.

In one embodiment, the present invention provides a method for the treatment or prophylaxis of neurodegenerative diseases in a mammal, which method comprises administering an effective amount of a compound of formula (I) as described herein, or of a pharmaceutically acceptable salt thereof, to the mammal.

In one aspect, the present invention provides a method for the treatment or prophylaxis of multiple sclerosis, Alzheimer's disease, Parkinson's disease, amyotrophic lateral sclerosis, traumatic brain injury, neurotoxicity, stroke, epilepsy, anxiety, migraine, depression and/or pain in a mammal, which method comprises administering an effective amount of a compound of formula (I) as described herein, or of a pharmaceutically acceptable salt thereof, to the mammal.

In a preferred embodiment, the present invention provides a method for the treatment or prophylaxis of multiple sclerosis, Alzheimer's disease and/or Parkinson's disease in a mammal, which method comprises administering an effective amount of a compound of formula (I) as described herein, or of a pharmaceutically acceptable salt thereof, to the mammal.

In a particularly preferred embodiment, the present invention provides a method for the treatment or prophylaxis of multiple sclerosis in a mammal, which method comprises administering an effective amount of a compound of formula (I) as described herein, or of a pharmaceutically acceptable salt thereof, to the mammal.

Pharmaceutical Compositions and Administration

In one aspect, the present invention provides a pharmaceutical composition comprising a compound of formula (I) as described herein and a therapeutically inert carrier.

The compounds of formula (I) and their pharmaceutically acceptable salts and esters can be used as medicaments (e.g. in the form of pharmaceutical preparations). The pharmaceutical preparations can be administered internally, such as orally (e.g. in the form of tablets, coated tablets, dragées, hard and soft gelatin capsules, solutions, emulsions or suspensions), nasally (e.g. in the form of nasal sprays) or rectally (e.g. in the form of suppositories). However, the administration can also be effected parentally, such as intramuscularly or intravenously (e.g. in the form of injection solutions).

The compounds of formula (I) and their pharmaceutically acceptable salts and esters can be processed with pharmaceutically inert, inorganic or organic adjuvants for the production of tablets, coated tablets, dragées and hard gelatin capsules. Lactose, corn starch or derivatives thereof, talc, stearic acid or its salts etc. can be used, for example, as such adjuvants for tablets, dragées and hard gelatin capsules.

Suitable adjuvants for soft gelatin capsules are, for example, vegetable oils, waxes, fats, semi-solid substances and liquid polyols, etc.

Suitable adjuvants for the production of solutions and syrups are, for example, water, polyols, saccharose, invert sugar, glucose, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary in wide limits and will, of course, be fitted to the individual requirements in each particular case. In general, in the case of oral administration a daily dosage of about 0.1 mg to 20 mg per kg body weight, preferably about 0.5 mg to 4 mg per kg body weight (e.g. about 300 mg per person), divided into preferably 1-3 individual doses, which can consist, for example, of the same amounts, should be appropriate. It will, however, be clear that the upper limit given herein can be exceeded when this is shown to be indicated.

EXAMPLES

The invention will be more fully understood by reference to the following examples. The claims should not, however, be construed as limited to the scope of the examples.

In case the preparative examples are obtained as a mixture of enantiomers, the pure enantiomers can be separated by methods described herein or by methods known to the man skilled in the art, such as e.g., chiral chromatography (e.g., chiral SFC) or crystallization.

All reaction examples and intermediates were prepared under an argon atmosphere if not specified otherwise.

Abbreviations

AcOH=acetic acid, aq.=aqueous, Boc=tert-butyloxycarbonyl, BINAP=2,2'-bis(diphenylphosphino)-1,1'-binaphthyl, BnBr=Benzylbromide, n-BuLi=n-butyllithium, n-BuOH=Butanol, CAS RN=chemical abstracts registration number, $CHCl_3$=Chloroform, CyPrI=Cyclopropyl iodide, Davephos=2-Dicyclohexylphosphino-2'-(N,N-dimethylamino)biphenyl, DAST=diethylaminosulfur trifluoride, DCM=dichloromethane, DCE=1,2-dichloroethane, DCC=N,N'-dicyclohexylcarbodiimide, DIC=N,N'-diisopropylcarbodiimide, DMA=N,N-dimethylacetamide, DMAP=4-dimethylaminopyridine, DME=dimethoxyethane, DMF=N,N-dimethylformamide, EDCI=N-(3-dimethylaminopropyl)-N'-ethylcarbodiimide hydrochloride, EtOAc=ethylacetate, EtOH=ethanol, EtI=Ethyl iodide, HATU=O-(7-azabenzotriazol-1-yl)-1,1,3,3-tetramethyluronium hexafluorophosphate, HCl=hydrogen chloride, HPLC=high performance liquid chromatography, HOBt=1-hydroxybenzo-triazole, Huenig's base=$iPr_2NEt$=N-ethyl diisopropylamine, iPrI=isopropyl iodide, $K_2CO_3$=potassium carbonate, KH=potassium hydride, LDA=lithium diisopropylamide, LiHMDS=lithium bis(trimethylsilyl)amide, L-selectride=lithium tri-sec-butyl (hydrido)borate, MeOH=methanol, RT=room temperature, MeI=methyl iodide, MS=mass spectrum, MsOH=methyl sulfonic acid, NaH=sodium hydride, $NaHCO_3$=sodium hydrogen carbonate, $Na_2CO_3$=sodium carbonate, NaHMDS=sodium bis(trimethylsilyl)amide, NaOH=sodium hydroxide, $Na_2SO_4$=sodium sulfate, $NH_4Cl$=ammonium chloride, sat.=saturated, Pd/C=palladium on activated carbon, $Pd(OH)_2$=palladium hydroxyde=Pearlman's catalyst, $PtO_2$=platinum dioxide, PE=petroleum ether, PMB=4-methoxy benzyl ether, SFC=Supercritical Fluid Chromatography, TBAF=Tetra-n-butylammonium fluoride, TBTU=O-benzotriazol-1-yl-N,N,N',N'-tetramethyl-uronium tetrafluoroborate, TEA=triethylamine, TFA=trifluoroacetic acid, $Tf_2NPh$=N-phenyltrifluoromethanesulfonimide, $Tf_2O$=trifluoromethanesulfonic anhydride, TfOH=triflic acid, THF=tetrahydrofuran, TsOH=paratoluene sulfonic acid, $T_3P$=propylphosphonic anhydride, Xantphos=4,5-Bis (diphenylphosphino)-9,9-dimethylxanthene.

Intermediate I-1

Tert-butyl 7-oxo-3,4,6,8,9,9a-hexahydro-1H-pyrido [1,2-a]pyrazine-2-carboxylate

Step [A] 5-[(4-methoxyphenyl)methoxy]pyridine-2-carbonitrile

To a solution of (4-methoxyphenyl)methanol (75.5 g, 546.4 mmol) in DMF (1000 mL) cooled at 0° C. was added 65% NaH dispersion in mineral oil (32.8 g, 819.6 mmol) portionwise and the mixture was stirred at this temperature for 30 min. Then, 3-bromo-6-pyridinecarbonitrile (CAS RN 97483-77-7, 100.0 g, 546.4 mmol) was added in portions and the reaction mixture was stirred at room temperature for 2 hours. The mixture was poured into a sat. $NH_4Cl$ aq. solution (3000 mL), filtered and washed with EtOAc (3×200 mL). The combined organic layers were dried over $Na_2SO_4$, filtered and concentrated in vacuo to give the crude title compound (112 g, 85.3%) as a pink solid; MS (ESI): m/z=241.1 $[M+H]^+$.

Step [B] [5-[(4-methoxyphenyl)methoxy]-2-pyridyl] methanamine

To a solution of 5-[(4-methoxyphenyl)methoxy]pyridine-2-carbonitrile (50.0 g, 208.1 mmol) in methanol (2000 mL) was added Raney Nickel (10.0 g, 170.4 mmol) followed by ammonium hydroxide (20.0 mL, 266.7 mmol). The reaction mixture was then heated to 50° C. under 3.5 bar of $H_2$ atmosphere for 12 hours. The mixture was filtered and the resulting filtrate was concentrated in vacuo to give the crude title compound (50 g, 98.3% yield) as a dark red solid; MS (ESI): m/z=245.3 $[M+H]^+$.

Step [C] 2-bromo-N-[[5-[(4-methoxyphenyl) methoxy]-2-pyridyl]methyl]acetamide To a solution of [5-[(4-methoxyphenyl)methoxy]-2-pyridyl]methanamine (43.6 g, 178.5 mmol) in DCM (200 mL) cooled at 0° C. was added EDCI (34.1 g, 178.5 mmol) followed by bromoacetic acid (24.8 g, 178.5 mmol) in portions and the reaction mixture was stirred at room temperature for 1 hour. The mixture was poured into a sat. $NaHCO_3$ aq. solution (200 mL). The organic layer was separated, washed with more sat. $NaHCO_3$ aq. solution (3×50 mL), brine (50 mL), dried over $Na_2SO_4$ and concentrated in vacuo to give the crude title compound (60.6 g, 93% yield) as a dark red oil; MS (ESI): m/z=367.2 [M+2]$^+$ Step [D] 7-[(4-methoxyphenyl)methoxy]-1,2,4,6,9,9a-hexahydropyrido[1,2-a]pyrazin-3-one 2-bromo-N-[[5-[(4-methoxyphenyl)methoxy]-2-pyridyl]methyl]acetamide (11.60 g, 31.76 mmol, 1 eq) was dissolved in $CH_3CN$ (150 mL) and stirred at 50° C. for 12 hours. The reaction mixture was concentrated in vacuo to remove the solvent, the residue was re-dissolved in MeOH (150 mL) and cooled to 0° C. Then, sodium borohydride (12.01 g, 317.5 mmol) was carefully added to the reaction mixture which was stirred at room temperature for 12 hours. The mixture was evaporated to dryness and the residue was purified by silica gel flash chromatography eluting with a 1 to 10% MeOH in DCM gradient to give the crude product. This material was then triturated with EtOAc (50 mL), filtered and further dried under high vacuum to give the title compound (3.1 g, 33.9%) as a yellow solid; MS (ESI): m/z=289.1 [M+H]$^+$.

Step [E] 7-[(4-methoxyphenyl)methoxy]-2,3,4,6,9,9a-hexahydro-H-pyrido[1,2-a]pyrazine To a solution of 7-[(4-methoxyphenyl)methoxy]-1,2,4,8,9,9a-hexahydropyrido [1,2-a]pyrazin-3-one (3.10 g, 10.7 mmol) in THF (100 mL) cooled at 0° C., was carefully added $LiAlH_4$ (1.02 g, 26.9 mmol) and the reaction mixture was heated to 80° C. for 2 hours. The mixture was cooled to 0° C., quenched with water (4 mL) and a 20% aq. $NaHCO_3$ solution (4 mL). The mixture was filtered, washed with THF (3×20 mL) and the resulting filtrate was concentrated in vacuo to give the crude title compound (2.9 g, 98%) as a yellow solid; MS (ESI): m/z=275.3 [M+H]$^+$.

Step [F] Tert-butyl 7-oxo-3,4,6,8,9,9a-hexahydro-1H-pyrido[1,2-a]pyrazine-2-carboxylate To a solution of 7-[(4-methoxyphenyl)methoxy]-2,3,4,6,9,9a-hexahydro-1H-pyrido[1,2-a]pyrazine (1 g, 3.93 mmol) in DCM (50 mL) was added TFA (10.0 mL, 10.57 mmol), and the reaction mixture was stirred at room temperature for 1 hour. The mixture was concentrated in vacuo to remove the solvent, the residue was re-dissolved in $CH_3CN$ (50 mL) and cooled to 0° C. Then, $Na_2CO_3$ (3.3 g, 31.13 mmol) followed by di-tert-butyldicarbonate (6.8 g, 31.1 mmol) were added and the reaction mixture was stirred at room temperature for 12 hours. The mixture was diluted with water (100 mL) and extracted with EtOAc (3×100 mL). The combined organic layers were washed with water (3×30 mL), brine (50 mL), dried over $Na_2SO_4$ and concentrated in vacuo. The residue was purified by silica gel flash chromatography eluting with a 10 to 30% of EtOAc in PE to give the title compound (2.62 g, 99.3%) as a light yellow solid.

Intermediate I-2A and I-2B (7S,9aR)-7-(4-chlorophenyl)-1,2,3,4,6,8,9,9a-octahydropyrido[1,2-a]pyrazin-7-ol and (7R,9aS)-7-(4-chlorophenyl)-1,2,3,4,6,8,9,9a-octahydropyrido[1,2-a]pyrazin-7-ol Step [A] Tert-butyl Rac-(7R,9aS)-7-(4-chlorophenyl)-7-hydroxy-3,4,6,8,9,9a-hexahydro-1H-pyrido[1,2-a]pyrazine-2-carboxylate To a solution of tert-butyl 7-oxo-3,4,6,8,9,9a-hexahydro-1H-pyrido[1,2-a]pyrazine-2-carboxylate (Intermediate I-1, 1 g, 3.93 mmol) in THF (65 ml) cooled at 0° C., was added a 1M solution of 4-chlorophenylmagnesium bromide in THF (7.08 ml, 7.08 mmol) dropwise while keeping the temperature between 0 and 1° C., then the reaction mixture was stirred at room temperature for 3 hours. The mixture was diluted with EtOAc, poured into a sat. $NH_4Cl$ aq. solution and extracted with EtOAc. The combined organic layer was washed with brine, dried over $Na_2SO_4$, filtered and concentrated in vacuo. The residue was purified by flash chromatography, eluting with a 30 to 100% EtOAc-heptane gradient to give the title compound (0.295 g, 20%) as red oil; MS (ESI): m/z=367.2 [M+H]$^+$.

Step [B] (7S,9aR)-7-(4-chlorophenyl)-1,2,3,4,6,8,9,9a-octahydropyrido[1,2-a]pyrazin-7-ol and (7R,9aS)-7-(4-chlorophenyl)-1,2,3,4,6,8,9,9a-octahydropyrido[1,2-a]pyrazin-7-ol To a solution of tert-butyl rac-(7R,9aS)-7-(4-chlorophenyl)-7-hydroxy-3,4,6,8,9,9a-hexahydro-1H-pyrido[1,2-a]pyrazine-2-carboxylate (0.8 g, 2.18 mmol) in dioxane (5 mL) cooled at 0° C., was added 4M HCl in dioxane (5.45 mL, 21.8 mmol) and the reaction mixture was stirred at room temperature for 15 hours. The resulting suspension was diluted with EtOAc, slowly poured into a cold sat. aqueous $Na_2CO_3$ solution and extracted with EtOAc. The combined organic layer was washed with brine, dried over $Na_2SO_4$, filtered and concentrated in vacuo. The residue was submitted to chiral SFC separation to give respectively (7S,9aR)-7-(4-chlorophenyl)-1,2,3,4,6,8,9,9a-octahydropyrido[1,2-a]pyrazin-7-ol (Intermediate I-2A, 0.195 g, 32%) and (7R,9aS)-7-(4-chlorophenyl)-1,2,3,4,6,8,9,9a-octahydropyrido[1,2-a]pyrazin-7-ol (Intermediate I-2B, 0.190 g, 31%) as orange semi-solids; MS (ESI): m/z=267.2 [M+H]$^+$.

Intermediate I-3A and I-3B (7S,9aR)-7-(3-chloro-4-fluoro-phenyl)-1,2,3,4,6,8,9,9a-octahydropyrido[1,2-a]pyrazin-7-ol and (7R,9aS)-7-(3-chloro-4-fluoro-phenyl)-1,2,3,4,6,8,9,9a-octahydropyrido[1,2-a]pyrazin-7-ol Intermediate I-3A and I-3B were prepared in analogy to intermediate I-2A and I-2B, but using in step [A] a 0.5M solution of 3-chloro-4-fluorophenylmagnesium bromide in THF (CAS RN 413589-34-1) to give respectively the title compounds as yellow oils; MS (ESI): m/z=285.1 [M+H]$^+$.

Intermediate I-4A (7R,9aR)-7-[5-(trifluoromethyl)-2-pyridyl]-1,2,3,4,6,8,9,9a-octahydropyrido[1,2-a]pyrazin-7-ol Step [A] Tert-butyl Rac-(7R,9aR)-7-hydroxy-7-[5-(trifluoromethyl)-2-pyridyl]-3,4,6,8,9,9a-hexahydro-1H-pyrido[1,2-a]pyrazine-2-carboxylate To a solution of 2-bromo-5-(trifluoromethyl)pyridine (CAS RN 50488-42-1, 1 g, 4.42 mmol) in toluene (14.3 mL) cooled to −78° C., was added a 1.6M solution of nBuLi in hexanes (3.04 mL, 4.87 mmol) and the mixture was stirred at this temperature for 5 minutes. Then, a cooled solution of tert-butyl 7-oxo-3,4,6,8,9,9a-hexahydro-1H-pyrido[1,2-a]pyrazine-2-carboxylate (Intermediate I-1, 1.24 g, 4.87 mmol) in toluene (14 ml) was added dropwise while keeping the temperature at −78° C. and the reaction mixture was stirred for 1.5 hours. The reaction was quenched with a sat. $NH_4Cl$ aq. solution and the mixture was extracted with EtOAc. Combined organics were washed with water, brine, dried over $Na_2SO_4$, filtered and concentrated in vacuo. The residue was purified by silica gel flash chromatography, eluting with a 20 to 80% EtOAc-heptane gradient to give the title compound (0.817 g, 46%) as a light yellow viscous oil; MS (ESI): m/z=402.3 $[M+H]^+$.

Step [B] Tert-butyl (7S,9aS)-7-hydroxy-7-[5-(trifluoromethyl)-2-pyridyl]-3,4,6,8,9,9a-hexahydro-1H-pyrido[1,2-a]pyrazine-2-carboxylate and Tert-butyl (7R,9aR)-7-hydroxy-7-[5-(trifluoromethyl)-2-pyridyl]-3,4,6,8,9,9a-hexahydro-1H-pyrido[1,2-a]pyrazine-2-carboxylate tert-Butyl rac-(7R,9aR)-7-hydroxy-7-[5-(trifluoromethyl)-2-pyridyl]-3,4,6,8,9,9a-hexahydro-1H-pyrido[1,2-a]pyrazine-2-carboxylate was submitted to chiral SFC separation to give respectively (7S,9aS)-7-(4-chlorophenyl)-1,2,3,4,6,8,9,9a-octahydropyrido[1,2-a]pyrazin-7-ol (0.326 g, 37%) and (7R,9aR)-7-(4-chlorophenyl)-1,2,3,4,6,8,9,9a-octahydropyrido[1,2-a]pyrazin-7-ol (0.252 g, 31%) as light brown solids; MS (ESI): m/z=402.3 $[M+H]^+$.

Step [C] (7R,9aR)-7-[5-(trifluoromethyl)-2-pyridyl]-1,2,3,4,6,8,9,9a-octahydropyrido[1,2-a]pyrazin-7-ol To a solution of tert-butyl (7R,9aR)-7-hydroxy-7-[5-(trifluoromethyl)-2-pyridyl]-3,4,6,8,9,9a-hexahydro-1H-pyrido[1,2-a]pyrazine-2-carboxylate (0.25 g, 0.623 mmol) in dioxane (1.5 mL) cooled at 0° C., was added 4M HCl in dioxane (1.56 mL, 6.23 mmol) and the reaction mixture was stirred at room temperature for 15 hours. The mixture was evaporated to dryness to give the crude title compound (Intermediate I-4A, 0.23 g) as a light brown solid as hydrochloride salt; MS (ESI): m/z=470.2 $[M+H]^+$.

Intermediate I-4B (7S,9aS)-7-[5-(trifluoromethyl)-2-pyridyl]-1,2,3,4,6,8,9,9a-octahydropyrido[1,2-a]pyrazin-7-ol was prepared in analogy to intermediate I-4A, but using in step [C] tert-butyl (7S,9aS)-7-hydroxy-7-[5-(trifluoromethyl)-2-pyridyl]-3,4,6,8,9,9a-hexahydro-1H-pyrido[1,2-a]pyrazine-2-carboxylate to give the crude title compound as a light brown solid as hydrochloride salt; MS (ESI): m/z=470.2 $[M+H]^+$.

Intermediate I-5

2-(2-Chloro-3-methoxybenzoyl)-3,4,6,8,9,9a-hexahydro-1H-pyrido[1,2-a]pyrazin-7-one Step [A] (2-Chloro-3-methoxyphenyl)-[7-[(4-methoxyphenyl)methoxy]-1,3,4,6,9,9a-hexahydropyrido[1,2-a]pyrazin-2-yl]methanone To a solution of 2-chloro-3-methoxybenzoic acid (2.94 g, 15.75 mmol) and 7-[(4-methoxyphenyl)methoxy]-2,3,4,6,9,9a-hexahydro-1H-pyrido[1,2-a]pyrazine (Intermediate I-1 [E], 3.6 g, 13.12 mmol) in DMF (50 mL) cooled at 0° C. was added TEA (5.6 mL, 39.36 mmol) followed by $T_3P$ (9.06 g, 19.68 mmol), then the reaction mixture was heated to 50° C. for 12 hours. The reaction was diluted with water (100 mL) and extracted with EtOAc (2×80 mL). The combined organic layer was washed with water (2×50 mL) and brine (50 mL), dried over $Na_2SO_4$, filtered and concentrated in vacuo. The residue was purified by silica gel flash chromatography, eluting with a 50 to 100% EtOAc-heptane gradient to give the title compound (3.9 g, 67.1%) as a yellow solid; MS (ESI): m/z=443.2 $[M+H]^+$.

Step [B] 2-(2-Chloro-3-methoxybenzoyl)-3,4,6,8,9,9a-hexahydro-1H-pyrido[1,2-a]pyrazin-7-one To a solution of (2-chloro-3-methoxy-phenyl)-[7-[(4-methoxyphenyl)methoxy]-1,3,4,6,9,9a-hexahydropyrido[1,2-a]pyrazin-2-yl]methanone (3.9 g, 8.8 mmol) in DCM (50 mL) cooled to 0° C. was added TFA (3.39 mL, 44 mmol), then the reaction mixture was stirred at room temperature for 1 hour. The mixture was concentrated in vacuo, the residue taken up in EtOAc, poured into a saturated aq. $NaHCO_3$ solution (100 mL) and the aqueous layer was extracted with EtOAc (2×50 mL). Combined organics were washed with brine, dried over $Na_2SO_4$, filtered and evaporated. The residue was purified by silica gel flash chromatography, eluting with a 50 to 100% EtOAc-heptane gradient to give the title compound (2.1 g, 73.9%) as a light yellow foam. MS (ESI): m/z=341.2 $[M+H_2O+H]^+$.

Intermediate I-6

(7R,9aR)-7-(4-Chlorophenyl)octahydro-1H-pyrido[1,2-a]pyrazine

Step [A] Tert-butyl 7-(4-chlorophenyl)-7-hydroxy-3,4,6,8,9,9a-hexahydro-1H-pyrido[1,2-a]pyrazine-2-carboxylate To a solution of tert-butyl 7-oxo-3,4,6,8,9,9a-hexahydro-1H-pyrido[1,2-a] pyrazine-2-carboxylate (Intermediate I-1, 1.0 g, 3.93 mmol) in THF (30 mL) cooled at 0° C. was added 4-chlorophenylmagnesium bromide (1M solution in THF, 7.08 mL, 7.08 mmol) and the reaction mixture was stirred at room temperature for 2 hours. The mixture was poured into a saturated $NH_4Cl$ aq. solution (100 mL) and extracted with EtOAc (3×50 mL). The combined organic phase was washed with brine, dried over $Na_2SO_4$, filtered and concentrated in vacuo. The residue was purified by silica flash chromatography, eluting with a 5% to 25% EtOAc-PE gradient to give the title compound (0.820 g, 56.8%) as a light yellow oil; MS (ESI): m/z=367.1 $[M+H]^+$.

Step [B] 7-(4-chlorophenyl)-2,3,4,8,9,9a-hexahydro-1H-pyrido[1,2-a]pyrazine

To a solution of tert-butyl 7-(4-chlorophenyl)-7-hydroxy-3,4,6,8,9,9a-hexahydro-1H-pyrido [1,2-a]pyrazine-2-carboxylate (0.820 g, 2.24 mmol) in DCM (25 mL) was added methane sulfonic acid (5.0 mL, 164 mmol) and the reaction mixture was stirred at 20° C. for 18 hours. The mixture was poured into a sat. $NaHCO_3$ aq. solution (100 mL) and extracted with DCM (3×50 mL). The combined organic phase was washed with brine, dried over $Na_2SO_4$, filtered and concentrated in vacuo to give the crude title compound (0.560 g,) as a light yellow oil; MS (ESI): m/z=249.1 $[M+H]^+$.

Step [C] Rac-(7R,9aS)-7-(4-chlorophenyl)-2,3,4,6,7,8,9,9a-octahydro-1H-pyrido[1,2-a]pyrazine, (7R,9aR)-7-(4-chlorophenyl)-2,3,4,6,7,8,9,9a-octahydro-1H-pyrido[1,2-a]pyrazine and (7S,9aS)-7-(4-chlorophenyl)-2.3.4.6.7.8.9.9a-octahydro-1H-pyrido[1,2-a]pyrazine To a solution of 7-(4-chlorophenyl)-2,3,4,8,9,9a-hexahydro-1H-pyrido[1,2-a]pyrazine (0.130 g, 0.523 mmol) in THF (2.5 mL) and AcOH (0.250 mL) was added $PtO_2$ (0.025 g, 0.523 mmol) and the mixture was stirred at room temperature under 4 bars of $H_2$ pressure for 2 hours. The mixture was filtered and the filtrate was concentrated in vacuo. The residue was purified by SFC to give respectively rac-(7R,9aS)-7-(4-chlorophenyl)-2,3,4,6,7,8,9,9a-octahydro-1H-pyrido[1,2-a]pyrazine (peak A, 0.020 g, 14%), (7R,9aR)-7-(4-chlorophenyl)-2,3,4,6,7,8,9,9a-octahydro-1H-pyrido[1,2-a]pyrazine (peak B, 0.018 g, 11%) and (7S,9aS)-7-(4-chlorophenyl)-2,3,4,6,7,8,9,9a-octahydro-1H-pyrido[1,2-a]pyrazine (peak C, 0.015 g, 9%) as off-white foams; MS (ESI): m/z=251.2 $[M+H]^+$.

Intermediate I-7

[3-[(7S,9aR)-7-(4-chlorophenyl)-7-hydroxy-3,4,6,8,9,9a-hexahydro-1H-pyrido[1,2-a]pyrazine-2-carbonyl]-2-chloro-phenyl]boronic Acid To a solution of (7S,9aR)-7-(4-chlorophenyl)octahydro-2H-pyrido[1,2-a]pyrazin-7-ol (Intermediate I-2A, 0.05 g, 0.187 mmol) and 2-chloro-3-(4,4,5,5-tetramethyl-1,3,2-dioxaborolan-2-yl)benzoic acid (CAS RN 1046153-00-7, 0.053 g, 0.187 mmol) in DMF (1.5 mL) cooled to 0° C. with an ice bath, was added Hunig's base (0.082 mL, 0.469 mmol) followed by HATU (0.086 g, 0.225 mmol) and the reaction mixture was stirred at room temperature for 3 hours. The mixture was concentrated in vacuo and the residue was purified by reversed-phase HPLC to give the title compound (0.065 g, 73%) as a colorless lyophilised powder; MS (ESI): m/z=449.3 [M+H]+.

Intermediate I-8

(2-chloro-3-((7R,9aR)-7-hydroxy-7-(5-(trifluoromethyl)pyridin-2-yl)octahydro-2H-pyrido[1,2-a]pyrazine-2-carbonyl)phenyl)boronic Acid was prepared in analogy to intermediate I-7, but using (7R,9aR)-7-[5-(trifluoromethyl)-2-pyridyl]-1,2,3,4,6,8,9,9a-octahydropyrido[1,2-a]pyrazin-7-ol (Intermediate I-4A) to give the crude title compound as a light yellow solid; MS (ESI): m/z=484.3 $[M+H]^+$.

Intermediate I-9

[(7S,9aR)-7-(4-chlorophenyl)-7-hydroxy-3,4,6,8,9,9a-hexahydro-1H-pyrido[1,2-a]pyrazin-2-yl]-(5-bromo-4-chloropyridin-3-yl)methanone was prepared in analogy to intermediate I-7, but using 5-bromo-4-chloronicotinic acid (CAS RN 1256790-85-8) to give the crude title compound as a light yellow solid; MS (ESI): m/z=486.2 $[M+H]^+$.

Intermediate I-10A and I-10B (7S,9aR)-7-(3,4-difluorophenyl)-1,2,3,4,6,8,9,9a-octahydropyrido[1,2-a]pyrazin-7-ol and (7R,9aS)-7-(3,4-difluorophenyl)-1,2,3,4,6,8,9,9a-octahydropyrido[1,2-a]pyrazin-7-ol Step [A] Tert-butyl rac-(7R,9aS)-7-(4-chlorophenyl)-7-hydroxy-3,4,6,8,9,9a-hexahydro-1H-pyrido[1,2-a]pyrazine-2-carboxylate To a solution of tert-butyl 7-oxooctahydro-2H-pyrido[1,2-a]pyrazine-2-carboxylate (Intermediate I-1, 1.5 g, 5.9 mmol) in Me-THF (5 mL) cooled at −20° C., was added a 0.5M solution of (3,4-difluorophenyl)magnesium bromide (CAS RN 90897-92-0, 13 mL, 6.49 mmol) in Me-THF dropwise while keeping the temperature at −20° C. The reaction mixture was then stirred at room temperature for 4 hours. The mixture was diluted with EtOAc, poured into a sat. $NH_4Cl$ (25 mL) and extracted with EtOAc (2×50 mL). The organic layers were combined, washed with brine, dried over sodium sulfate and concentrated in vacuo. The residue was purified by silica gel flash chromatography, eluting with a 10 to 40% EtOAc in heptane gradient to give the title compound (0.833 g, 38%, 1:3 Cis:Trans) as a colorless foam; MS (ESI): m/z=385.2 $[M+H]^+$.

Step [B] (7S,9aR)-7-(3,4-difluorophenyl)-1,2,3,4,6,8,9,9a-octahydropyrido[1,2-a]pyrazin-7-ol and (7R,9aS)-7-(3,4-difluorophenyl)-1,2,3,4,6,8,9,9a-octahydropyrido[1,2-a]pyrazin-7-ol To a solution of tert-butyl 7-(3,4-difluorophenyl)-7-hydroxyoctahydro-2H-pyrido[1,2-a]pyrazine-2-carboxylate (0.83 g, 2.25 mmol) in DCM (2.5 mL) cooled to 0° C. with an ice bath was added TFA (1.04 mL, 13.5 mmol) and the reaction mixture was stirred at room temperature overnight. The cooled mixture was carefully basified with the dropwise addition of a 2M aqueous NaOH solution (7.88 mL, 15.8 mmol) and the resulting aqueous phase was extracted with DCM. Combined organic phases were dried over $Na_2SO_4$, filtered and evaporated to dryness. The crude material was purified by SFC to give respectively one of the Cis product (peak A), a mixture of Cis and Trans products (0.236 g, peak B) and (7R,9aS)-7-(3,4-difluorophenyl)-1,2,3,4,6,8,9,9a-octahydropyrido[1,2-a]pyrazin-7-ol (Intermediate I-10B, 0.160 g, peak C). Peak B was purified a second time by SFC to give (7S,9aR)-7-(3,4-difluorophenyl)-1,2,3,4,6,8,9,9a-octahydropyrido[1,2-a]pyrazin-7-ol (Intermediate I-10A, 0.160 g, 26%) as an orange oil; MS (ESI): m/z=285.1 $[M+H]^+$.

Intermediate I-11

[(7S,9aR)-7-(4-chlorophenyl)-7-hydroxy-3,4,6,8,9,9a-hexahydro-1H-pyrido[1,2-a]pyrazin-2-yl]-(5-bromo-4-methylpyridin-3-yl)methanone was prepared in analogy to intermediate I-7, but using 5-bromo-4-methylnicotinic acid (CAS RN 677702-58-8) to give the crude title compound as a colorless solid; MS (ESI): m/z=464.2 $[M+H]^+$.

Intermediate A-1

Lithium;2-chloro-3-(3-hydroxyazetidin-1-yl)benzoate

Step [A] Methyl 2-chloro-3-(3-hydroxyazetidin-1-yl)benzoate

In a sealed tube, methyl 3-bromo-2-chlorobenzoate (CAS RN 871224-19-0, 0.1 g, 0.401 mmol), cesium carbonate (0.261 g, 0.802 mmol), $Pd_2(dba)_3$ (0.037 g, 0.040 mmol) and Xantphos (23.2 mg, 40.1 μmol, Eq: 0.1) were mixed in dioxane (1 mL). The mixture was degassed with argon, then azetidin-3-ol (CAS RN 45347-82-8, 0.059 g, 0.802 mmol) was added and the reaction mixture was heated to 100° C. for 16 hours. The mixture was diluted with EtOAc and washed with water and brine. The organic phase was dried over $Na_2SO_4$, filtered and concentrated in vacuo. The residue was purified by silica gel flash chromatography, eluting with a 0 to 50% EtOAc-heptane gradient to give the title compound (0.034 g, 35%) as an orange viscous oil; MS (ESI): m/z=242.1 [M+H]+.

Step [B] Lithium:2-chloro-3-(3-hydroxyazetidin-1-yl)benzoate

To a solution of methyl 2-chloro-3-(3-hydroxyazetidin-1-yl)benzoate (0.035 g, 0.145 mmol) in THF (0.350 mL) was added a 1M LiOH aq. solution (0.29 mL, 290 mmol) and the reaction mixture was stirred at room temperature for 5 hours. The mixture concentrated in vacuo and the residue triturated in diisopropylether, filtered off and further dried on the high vacuum to give the crude title compound (0.032 g, 82%) as a light brown solid as lithium salt; MS (ESI): m/z=228.1 $[M+H]^+$.

Intermediate A-2

Lithium;2-fluoro-3-(3-hydroxyazetidin-1-yl)benzoate was prepared in analogy to intermediate A-1, but using in step [A] methyl 3-bromo-2-fluorobenzoate (CAS RN 206551-41-9) to give the crude title compound as a yellow solid as lithium salt; MS (ESI): m/z=212.0 $[M+H]^+$.

Intermediate A-3

2-Chloro-3-(1H-pyrazol-5-yl)benzoic acid

Step [A] Methyl 2-chloro-3-(1H-pyrazol-5-yl)benzoate

In a sealed tube, methyl 3-bromo-2-chlorobenzoate (CAS RN 871224-19-0, 0.6 g, 2.4 mmol), tert-butyl 3-(4,4,5,5-tetramethyl-1,3,2-dioxaborolan-2-yl)-1H-pyrazole-1-carboxylate (CAS RN 1256359-17-7, 0.778 g, 2.65 mmol) and bis(triphenylphosphine)palladium (II) chloride (0.169 g, 0.240 mmol) were mixed in DMF (6 mL). The reaction mixture was purged with Argon. Then, a 1M aqueous solution of $Na_2CO_3$ (7.21 mL, 7.21 mmol) was added and the reaction mixture heated to 100° C. for 4 hours. The mixture was diluted with EtOAc, poured into water and the aqueous layer was extracted with EtOAc. Combined organics were washed with brine, dried over $Na_2SO_4$, filtered and concentrated in vacuo. The residue was purified by silica gel flash chromatography, eluting with a 50 to 100% EtOAc-heptane gradient to give the title compound (0.195 g, 34%) as a yellow solid; MS (ESI): m/z=237.1 [M+H]+.

Step [B] 2-Chloro-3-(1H-pyrazol-5-yl)benzoic Acid

To a solution of methyl 2-chloro-3-(1H-pyrazol-3-yl) benzoate (0.195 g, 0.824 mmol) in THF (2 mL) was added a 1M aqueous solution of LiOH (1.65 ml, 1.65 mmol) and the reaction mixture was stirred at room temperature for 3 hours. The reaction mixture was acidified to pH=4 with the addition of a 2M HCl aqueous solution (0.8 mL) and the aqueous layer was extracted with Me-THF (2×10 mL). Combined organics were dried over $Na_2SO_4$, filtered and evaporated to dryness to give the crude title compound (0.144 g, 82%) as a yellow solid; MS (ESI): m/z=223.0 [M+H]+.

Intermediate A-4

2-Chloro-3-(4-methyl-1H-pyrazol-3-yl)benzoic Acid was prepared in analogy to intermediate A-3, but using in step [A] tert-butyl 4-methyl-3-(4,4,5,5-tetramethyl-1,3,2-dioxaborolan-2-yl)-1H-pyrazole-1-carboxylate (CAS RN 1402174-62-2) to give the crude title compound as a white solid as; MS (ESI): m/z=237.1 $[M+H]^+$.

Intermediate A-5

2-Fluoro-3-(4-methyl-1H-pyrazol-3-yl)benzoic Acid was prepared in analogy to intermediate A-4, but using in step [A] methyl 3-bromo-2-fluorobenzoate (CAS RN 206551-41-9) to give the crude title compound as a white solid as; MS (ESI): m/z=221.1 $[M+H]^+$.

Intermediate A-6

3-(4-Methyl-1H-pyrazol-3-yl)benzoic Acid was prepared in analogy to intermediate A-4, but using in step [A] ethyl 3-bromobenzoate (CAS RN 24398-88-7) to give the crude title compound as a colorless oil as; MS (ESI): m/z=203.0 $[M+H]^+$.

Intermediate A-7

2-Fluoro-3-morpholino-benzoic Acid

Step [A] Methyl 2-fluoro-3-morpholino-benzoate

In a sealed tube, methyl 3-bromo-2-fluorobenzoate (CAS RN 206551-41-9, 0.050 g, 0.215 mmol), morpholine (0.022 mL, 0.257 mmol), $K_3PO_4$ (0.091 g, 0.429 mmol) and DavePhos (0.013 g, 0.032 mmol) were combined in Toluene (1 mL). The mixture was degassed with Argon. Then, $Pd_2(dba)_3$ (0.020 g, 0.021 mmol) was added and the reaction mixture heated to 80° C. for 15 hours. The mixture was evaporated to dryness and the residue purified by reversed-phase HPLC to give the title compound (0.051 g, 19.5%) as a colorless solid; MS (ESI): m/z=240.1 $[M+H]^+$.

Step [B] 2-fluoro-3-morpholino-benzoic Acid was prepared in analogy to intermediate A-3[B] to give the title compound as a colorless solid; MS (ESI): m/z=226.1 $[M+H]^+$.

Intermediate A-8

3-(4-tert-Butoxycarbonylpiperazin-1-yl)-2-fluorobenzoic Acid

Step [A] Tert-butyl 4-(2-fluoro-3-(methoxycarbonyl)phenyl)piperazine-1-carboxylate In a sealed tube, methyl 3-bromo-2-fluorobenzoate (CAS RN 206551-41-9, 0.050 g, 0.215 mmol), tert-butyl piperazine-1-carboxylate (0.042 g, 0.225 mmol), $Cs_2CO_3$ (0.140 g, 0.429 mmol) were combined in Toluene (1 mL). The mixture was degassed with Argon. Then, BINAP (0.013 g, 0.021 mmol) followed by $Pd_2(OAc)_2$ (0.005 g, 0.021 mmol) were added and the reaction mixture heated to 80° C. for 15 hours. The mixture was filtered over Dicalite, washed with EtOAc and the solution was concentrated in vacuo. The residue was purified by silica gel flash chromatography, eluting with a 0 to 100% EtOAc-heptane gradient to give the title compound (0.029 g, 35%) as a colorless viscous oil; MS (ESI): m/z=339.2 [M+H]+.

Step [B] 3-(4-tert-butoxycarbonylpiperazin-1-yl)-2-fluoro-benzoic Acid was prepared in analogy to intermediate A-3[B] to give the title compound as a yellow solid; MS (ESI): m/z=325.2 $[M+H]^+$.

Intermediate A-9

2-Fluoro-3-(3-oxopiperazin-1-yl)benzoic Acid

Step [A] Methyl 2-fluoro-3-(3-oxopiperazin-1-yl)benzoate was prepared in analogy to intermediate A-1[A], but using 2-piperazinone (CAS RN 5625-67-2) to give the title compound as off-white solid; MS (ESI): m/z=253.2 $[M+H]^+$.

Step [B] 2-Fluoro-3-(3-oxopiperazin-1-yl)benzoic Acid was prepared in analogy to intermediate A-3[B] to give the crude title compound as off-white solid; MS (ESI): m/z=239.2 $[M+H]^+$.

Intermediate A-10

2-Chloro-3-(3-oxopiperazin-1-yl)benzoic Acid was prepared in analogy to intermediate A-9, but using in step [A] methyl 3-bromo-2-chlorobenzoate (CAS RN 206551-41-9) to give the crude title compound as a colorless viscous oil; MS (ESI): m/z=255.2 $[M+H]^+$.

Intermediate A-11

Lithium;2-chloro-3-(6-oxa-1-azaspiro[3.3]heptan-1-yl)benzoic Acid was prepared in analogy to intermediate A-1, but using in step [A] 6-oxa-1-azaspiro[3.3]heptane (CAS RN 1046153-00-7) to give the crude title compound as a light yellow solid as lithium salt; MS (ESI): m/z=254.2 $[M+H]^+$.

Intermediate A-12

2-chloro-3-[(3S)-3-hydroxypyrrolidin-1-yl]benzoic Acid was prepared in analogy to intermediate A-9, but using in step [A] (S)-pyrrolidin-3-ol (CAS RN 100243-39-8) to give the crude title compound as a light brown foam; MS (ESI): m/z=256.1 $[M+H]^+$.

Intermediate A-13

2-chloro-3-[(3R)-3-hydroxypyrrolidin-1-yl]benzoic Acid was prepared in analogy to intermediate A-9, but using in step [A] (R)-pyrrolidin-3-ol (CAS RN 2799-21-5) to give the crude title compound as a brown foam; MS (ESI): m/z=242.1 $[M+H]^+$.

Intermediate A-14

Lithium;2-chloro-3-(3-hydroxy-3-methylazetidin-1-yl)benzoate was prepared in analogy to intermediate A-1, but using in step [A] 3-methylazetidin-3-ol trifluoroacetic acid (CAS RN 1104083-24-0) to give the crude title compound as a light brown oil as lithium salt; MS (ESI): m/z=240.2 $[M+H]^+$.

Intermediate A-15

Lithium;2-chloro-3-[(3S)-3-hydroxypiperidin-1-yl]benzoate

Step [A] Methyl 2-chloro-3-[(3S)-3-hydroxy-1-piperidyl]benzoate was prepared in analogy to intermediate A-8, but using (S)-piperidin-3-ol (CAS RN 24211-55-0) to give the title compound as a yellow oil; MS (ESI): m/z=270.1 $[M+H]^+$.

Step [B] 2-Fluoro-3-(3-oxopiperazin-1-yl)benzoic Acid was prepared in analogy to intermediate A-1[B] to give the crude title compound as white solid as lithium salt; MS (ESI): m/z=256.1 $[M+H]^+$.

Intermediate A-16

Lithium;2-chloro-3-[(3R)-3-hydroxypiperidin-1-yl]benzoate was prepared in analogy to intermediate A-15, but using in step [A] (R)-piperidin-3-ol (CAS RN 62414-68-0) to give the crude title compound as a white solid; MS (ESI): m/z=256.1 $[M+H]^+$.

Intermediate A-17

Lithium;2-chloro-3-(4-hydroxypiperidin-1-yl)benzoate was prepared in analogy to intermediate A-15, but using in step [A] piperidin-4-ol (CAS RN 5382-16-1) to give the crude title compound as an off-white powder as lithium salt; MS (ESI): m/z=256.2 $[M+H]^+$.

Intermediate A-18

Lithium;2-chloro-3-(3-hydroxy-3-methyl-pyrrolidin-1-yl)benzoate was prepared in analogy to intermediate A-1, but using in step [A] 3-methylpyrrolidin-3-ol (CAS RN 125032-87-3) to give the crude title compound as a light brown foam; MS (ESI): m/z=256.1 $[M+H]^+$.

Intermediate A-19

Lithium;2-chloro-3-((3S,4S)-3,4-dihydroxypyrrolidin-1-yl)benzoate was prepared in analogy to intermediate A-1, but using in step [A] (3S,4S)-pyrrolidine-3,4-diol (CAS RN 90481-32-6)

to give the crude title compound as an orange amorphous solid; MS (ESI): m/z=258.1 $[M+H]^+$.

Intermediate A-20

Lithium;2-chloro-3-(3-fluoro-3-(hydroxymethyl) azetidin-1-yl)benzoate was prepared in analogy to intermediate A-1, but using in step [A] 3-fluoroazetidin-3-yl)methanol (CAS RN 1268520-93-9) to give the crude title compound as a light yellow solid; MS (ESI): m/z=260.1 $[M+H]^+$.

Intermediate A-21

Lithium;2-chloro-3-(3-(hydroxymethyl)azetidin-1-yl)benzoate was prepared in analogy to intermediate A-1, but using in step [A] azetidin-3-ylmethanol (CAS RN 95849-02-8) to give the crude title compound as a light yellow solid; MS (ESI): m/z=242.1 $[M+H]^+$.

Intermediate A-22

2-Fluoro-3-(1H-pyrazol-3-yl)benzoic Acid

In a sealed tube, methyl 3-bromo-2-fluorobenzoate (CAS RN 206551-41-9, 0.155 g, 0.665 mmol) and tert-butyl 3-(4,4,5,5-tetramethyl-1,3,2-dioxaborolan-2-yl)-1H-pyrazole-1-carboxylate (CAS RN 1256359-17-7, 0.215 g, 0.732 mmol) were dissolved in DMF (2 mL). The mixture was degassed with Argon for 5 minutes. Then, bis(triphenylphosphine)palladium (II) chloride (0.047 mg, 0.066 mmol) followed by a 1M aqueous solution of $Na_2CO_3$ (2 mL, 2 mmol) were added and the reaction mixture was stirred at 100° C. overnight. The mixture was diluted with EtOAc and washed with $H_2O$. The layers were separated, the aqueous phase was acidified to pH=1 with HCl (25%) and extracted again with EtOAc. Combined organics were dried over $Na_2SO_4$, filtered and concentrated in vacuo. The residue was purified by reversed-phase HPLC to give some product (0.005 g). The aqueous layer was evaporated to dryness to give more product (0.025 g). Both material were combined to give the title compound (0.030 g, 21.9%) as a colorless solid; MS (ESI): m/z=207.1 [M+H]+.

Intermediate B-1

2-Chloro-3-(3-fluoro-1H-pyrazol-4-yl)benzoic acid

Step [A] Methyl 2-chloro-3-(3-fluoro-1H-pyrazol-4-yl)benzoate

In a microwave vial, methyl 2-chloro-3-(4,4,5,5-tetramethyl-1,3,2-dioxaborolan-2-yl)benzoate (CAS RN 2201133-24-4, 0.162 g, 0.546 mmol), 4-bromo-3-fluoro-1H-pyrazole (CAS RN 1346555-56-3, 0.060 g, 0.364 mmol) and $K_2CO_3$ (0.151 g, 1.09 mmol) were mixed in dioxane (7.8 mL)/water (2.6 mL). The reaction mixture was degassed with Argon. Then, bis(di-tert-butyl(4-dimethylaminophenyl)phosphine) dichloropalladium(II) (CAS RN 887919-35-9, 0.025 g, 0.036 mmol) was added to the mixture which was heated in the microwave to 115° C. for 30 minutes. The mixture was diluted with EtOAc, poured into a saturated aq. $NaHCO_3$ solution and the aqueous layer was extracted with EtOAc. Combined organics were washed with brine, dried over $Na_2SO_4$, filtered and concentrated in vacuo. The residue was purified by silica gel flash chromatography, eluting with a 0 to 50% EtOAc-heptane gradient to give the title compound (0.045 g, 49%) as a light yellow solid; MS (ESI): m/z=255.2 [M+H]+.

Step [B] 3-(3-Fluoro-1H-pyrazol-4-yl)benzoic Acid was prepared in analogy to intermediate A-3[B] to give the title compound as a yellow solid. MS (ESI): m/z=241.1 $[M+H]^+$.

Intermediate B-2

2-Fluoro-3-isothiazol-3-yl-benzoic Acid was prepared in analogy to intermediate B-1, but using in step [A] methyl 2-fluoro-3-(4,4,5,5-tetramethyl-1,3,2-dioxaborolan-2-yl)benzoate (CAS RN 1638847-77-4) and 3-bromoisothiazole (CAS RN 55512-82-8) to give the crude title compound as a brown oil; MS (ESI): m/z=224.1 $[M+H]^+$.

Intermediate B-3

2-Chloro-3-(4-fluoro-1H-pyrazol-5-yl)benzoic Acid was prepared in analogy to intermediate B-1, but using in step [A] 3-bromo-4-fluoro-1H-pyrazole (CAS RN 1621526-49-5) to give the crude title compound as a yellow oil; MS (ESI): m/z=255.1 $[M+H]^+$.

Intermediate B-4

Lithium;2-fluoro-3-(1H-pyrazol-5-yl)benzoate

Step [A] Methyl 2-fluoro-3-(1H-pyrazol-5-yl)benzoate

In a sealed tube, $K_2CO_3$ (0.412 g, 2.98 mmol), methyl 2-fluoro-3-(4,4,5,5-tetramethyl-1,3,2-dioxaborolan-2-yl) benzoate (CAS RN 1638847-77-4, 0.334 g, 1.19 mmol), 3-bromo-1H-pyrazole (CAS RN 14521-80-3, 0.146 g, 0.993 mmol) and bis(di-tert-butyl(4-dimethylaminophenyl)phosphine)dichloropalladium(II) (CAS RN 887919-35-9, 0.070 g, 0.099 mmol) were mixed in dioxane (5.5 mL) and water (1.8 mL). The mixture was degassed with Argon for 5 minutes. The reaction mixture was heated to 60° C. for 30 minutes and then to 110° C. for an additional 3 hours. The mixture was diluted with EtOAc, poured into a sat. $NaHCO_3$ aq. solution and the aqueous layer was extracted with EtOAc. Combined organics were washed with brine, dried over $Na_2SO_4$, filtered and evaporated. The residue was purified by silica gel flash chromatography, eluting with a 0 to 60% EtOAc-heptane gradient to give the title compound (0.59 g, 27%) as a light yellow solid; MS (ESI): m/z=221.1 [M+H]+.

Step [B] Lithium:2-fluoro-3-(1H-pyrazol-5-yl)benzoate was prepared in analogy to intermediate A-1[B] to give the title compound as a colorless solid. MS (ESI): m/z=207.0 $[M+H]^+$.

Intermediate B-5

2-fluoro-3-(4-fluoro-1H-pyrazol-5-yl)benzoic Acid was prepared in analogy to intermediate B-4, but using in step [A] 3-bromo-4-fluoro-1H-pyrazole (CAS RN 1621526-49-5) to give the crude title compound as a colorless solid; MS (ESI): m/z=225.1 $[M+H]^+$.

Intermediate B-6

Lithium;2-chloro-3-(1,2,4-thiadiazol-3-yl)benzoate was prepared in analogy to intermediate B-1, but using in step [A] 3-bromo-1,2,4-thiadiazole (CAS RN 1621526-49-5) to give the crude title compound as a colorless solid; MS (ESI): m/z=241.1 $[M+H]^+$.

Intermediate C-1

2-Chloro-3-(2-oxooxazolidin-3-yl)benzoic Acid

Step [A] Methyl 2-chloro-3-(2-oxooxazolidin-3-yl)benzoate

In a sealed tube, methyl 2-chloro-3-iodobenzoate (CAS RN 620621-51-4, 0.2 g, 0.675 mmol), oxazolidin-2-one (0.117 g, 1.35 mmol) and $K_2CO_3$ (0.233 g, 1.69 mmol) were mixed in acetonitrile (2 mL). The reaction mixture was purged with Argon. Then, N,N'-dimethylethane-1,2-diamine (0.012 g, 0.135 mmol) and copper(I) iodide (0.026 g, 0.135 mmol) were added and the reaction mixture heated to 80° C. for 15 hours. The mixture was diluted with EtOAc, poured into water and the aqueous layer was extracted with EtOAc. Combined organics were washed with brine, dried over $Na_2SO_4$, filtered and concentrated in vacuo. The residue was purified by reverse phase HPLC to give the title compound (0.036 g, 20%) as a light brown oil; MS (ESI): m/z=256.1 [M+H]+.

Step [B] 2-Chloro-3-(2-oxooxazolidin-3-yl)benzoic Acid was prepared in analogy to intermediate A-1[B] to give the title compound as an off-white solid. MS (ESI): m/z=242.0 $[M+H]^+$.

Intermediate C-2

Lithium, 2-Chloro-3-(2-oxoimidazolidin-1-yl)benzoate was prepared in analogy to intermediate C-1, but using in step [A] 1,3-dimethylurea to give the crude title compound as a white solid as lithium salt; MS (ESI): m/z=241.1 $[M+H]^+$.

Intermediate D-1a and D1-b

2-Bromo-3-[(Z)-styryl]benzoic Acid and 2-bromo-3-[(E)-styryl]benzoic Acid

Step [A] (2-Bromo-3-methoxycarbonyl-phenyl) methyl-triphenyl-phosphonium;bromide To a solution of triphenylphosphine (0.439 g, 1.67 mmol) in toluene (5 mL) was added methyl 2-bromo-3-(bromomethyl)benzoate (CAS RN 750585-90-1, 0.515 g, 1.67 mmol) and the reaction mixture was heated to 110° C. for 15 hours. The solid precipitate was filtered off, washed 3 times with diethyl ether and then further dried to give the crude title compound (0.918 g) as a white solid as hydrobromide salt; MS (ESI): m/z=491.1 $[M+H]^+$.

Step [B] Methyl 2-bromo-3-[(Z)-styryl]benzoate and methyl 2-bromo-3-[(E)-styryl]benzoate To a suspension of (2-bromo-3-methoxycarbonyl-phenyl) methyl-triphenyl-phosphonium bromide (0.102 g, 0.207 mmol) in THF (10 mL) cooled to 0° C. was added potassium tert-butoxide (0.025 g, 0.226 mmol) and the mixture stirred for 30 minutes. Then, benzaldehyde (0.019 mL, 0.188 mmol) in THF (5 mL) was added dropwise and the reaction mixture allowed to stir at room temperature for 4 hours. The mixture was quenched with a sat. $NH_4Cl$ aqueous solution and extracted with EtOAc. Combined organic layers were washed with brine, dried over $Na_2SO_4$, filtered and concentrated in vacuo. The residue was purified by silica column chromatography, eluting with a 0 to 40% EtOAc-heptane gradient to give respectively methyl 2-bromo-3-[(Z)-styryl] benzoate (0.013 g, 17%) and methyl 2-bromo-3-[(E)-styryl] benzoate (0.023 g, 38%) as yellow oils; MS (ESI): m/z=317.0 [M+H]+.

Step [C] 2-Bromo-3-[(Z)-styryl]benzoic Acid

To methyl (Z)-2-bromo-3-styrylbenzoate (0.113 g, 0.357 mmol) in THF (1 mL) was added a 1M LiOH aqueous solution (0.219 mL, 0.219 mmol) and reaction mixture was heated to 40° C. for 6 hours. The reaction was neutralised with 2M HCl aqueous solution and extracted with EtOAc. The organic layer was dried with $Na_2SO_4$, filtered and concentrated in vacuo to give the crude title compound (D1a, 0.095 g, 87%) as a white solid; MS (ESI): m/z=303.1 $[M+H]^+$.

Step [D] 2-Bromo-3-[(E)-styryl]benzoic Acid was prepared in analogy to step [C], but using methyl (E)-2-bromo-3-styrylbenzoate to give the crude title compound (D1b, 85%) as a white solid; MS (ESI): m/z=303.1 $[M+H]^+$.

Intermediate D-2

2-Bromo-3-[(E)-2-[4-(tert-butoxycarbonylamino) phenyl]vinyl]benzoic Acid was prepared in analogy to intermediate D-1b, but using in step [B] tert-butyl (4-formylphenyl)carbamate (CAS RN 144072-30-0) to give the crude title compound as a colorless oil; MS (ESI): m/z=418.2 $[M+H]^+$.

Intermediate D-3

2-Bromo-3-[(E)-2-(4-carboxyphenyl)vinyl]benzoic Acid was prepared in analogy to intermediate D-1b, but using in step [B] methyl 4-formylbenzoate (CAS RN 1571-08-0) to give the crude title compound as a colorless amorphous solid; MS (ESI): m/z=346.9 $[M+H]^+$.

Example 1

[(7S,9aR)-7-(3-Chloro-4-fluorophenyl)-7-hydroxy-3,4,6,8,9,9a-hexahydro-1H-pyrido[1,2-a]pyrazin-2-yl]-(2-chloro-3-methoxyphenyl)methanone In a flask, (7S,9aR)-7-(4-chlorophenyl)-1,2,3,4,6,8,9,9a-octahydropyrido[1,2-a]pyrazin-7-ol (Intermediate I-3A, 0.015 g, 0.053 mmol) and 2-chloro-3-methoxybenzoic acid (CAS RN 33234-36-5, 0.010 g, 0.055 mmol) were mixed in DMF (0.5 mL). Then, Hunig's base (0.023 mL, 0.132 mmol) was added followed by HATU (0.021 g, 0.055 mmol) and the reaction mixture was stirred at room temperature for 2 hours. The crude mixture was purified by reversed-phase HPLC to give the title compound (0.012 g, 50%) as a colorless amorphous solid; MS (ESI): m/z=453.2 $[M+H]^+$.

The following examples listed in Table 2 were prepared in analogy to the procedure described for the preparation of example 1 by using the indicated intermediates and/or commercial compounds and using the mentioned purification method such as reversed-phase HPLC (Gemini NX column) or silica gel flash chromatography

TABLE 2

| Ex | Name<br>Aspect<br>Purification method | Intermediates | MS, m/z $[M+H]^+$ or $[M-H]^-$ |
|---|---|---|---|
| 2 | [(7R,9aS)-7-(3-chloro-4-fluorophenyl)-7-hydroxy-3,4,6,8,9,9a-hexahydro-1H-pyrido[1,2-a]pyrazin-2-yl]-(2-chloro-3-methoxyphenyl)methanone<br>Colorless amorphous<br>Reversed-phase HPLC | Intermediate I-3B and 2-chloro-3-methoxybenzoic acid | 453.2 |
| 3 | [(7S,9aR)-7-(4-chlorophenyl)-7-hydroxy-3,4,6,8,9,9a-hexahydro-1H-pyrido[1,2-a]pyrazin-2-yl]-[2-chloro-3-(1H-pyrazol-5-yl)phenyl]methanone<br>Colorless amorphous<br>Reversed-phase HPLC | Intermediate I-2A and Intermediate A-3 | 471.2 |
| 4 | [(7R,9aS)-7-(4-chlorophenyl)-7-hydroxy-3,4,6,8,9,9a-hexahydro-1H-pyrido[1,2-a]pyrazin-2-yl]-[2-chloro-3-(1H-pyrazol-5-yl)phenyl]methanone<br>Colorless amorphous<br>Reversed-phase HPLC | Intermediate I-2B and Intermediate A-3 | 471.2 |
| 5 | [(7S,9aR)-7-(4-chlorophenyl)-7-hydroxy-3,4,6,8,9,9a-hexahydro-1H-pyrido[1,2-a]pyrazin-2-yl]-[2-chloro-3-(3-fluoro-1H-pyrazol-4-yl)phenyl]methanone<br>Colorless amorphous<br>Reversed-phase HPLC | Intermediate I-2A and Intermediate B-1 | 489.2 |
| 6 | [(7R,9aS)-7-(4-chlorophenyl)-7-hydroxy-3,4,6,8,9,9a-hexahydro-1H-pyrido[1,2-a]pyrazin-2-yl]-[2-chloro-3-(3-fluoro-1H-pyrazol-4-yl)phenyl]methanone<br>Colorless amorphous<br>Reversed-phase HPLC | Intermediate I-2B and Intermediate B-1 | 489.2 |
| 7 | [(7S,9aR)-7-(4-chlorophenyl)-7-hydroxy-3,4,6,8,9,9a-hexahydro-1H-pyrido[1,2-a]pyrazin-2-yl]-(2-chloro-6-methoxypyridin-3-yl)methanone<br>Colorless amorphous<br>Reversed-phase HPLC | Intermediate I-2A and 2-chloro-6-methoxy-3-pyridinecarboxylic acid (CAS RN 503000-87-1) | 436.2 |
| 8 | [(7S,9aR)-7-(4-chlorophenyl)-7-hydroxy-3,4,6,8,9,9a-hexahydro-1H-pyrido[1,2-a]pyrazin-2-yl]-(6-amino-2-methylpyridin-3-yl)methanone<br>Colorless amorphous<br>Reversed-phase HPLC | Intermediate I-2A and 6-amino-2-methyl-3-pyridinecarboxylic acid (CAS RN 680208-82-6) | 401.2 |
| 9 | [(7S,9aR)-7-(4-chlorophenyl)-7-hydroxy-3,4,6,8,9,9a-hexahydro-1H-pyrido[1,2-a]pyrazin-2-yl]-[2-chloro-3-(3-hydroxyazetidin-1-yl)phenyl]methanone<br>Colorless solid<br>Reversed-phase HPLC | Intermediate I-2A and Intermediate A-1 | 476.2 |
| 10 | [(7S,9aR)-7-(4-chlorophenyl)-7-hydroxy-3,4,6,8,9,9a-hexahydro-1H-pyrido[1,2-alpyrazin-2-yl]-[2-fluoro-3-(3-hydroxyazetidin-1-yl)phenyl]methanone<br>Colorless amorphous<br>Reversed-phase HPLC | Intermediate I-2A and Intermediate A-2 | 460.3 |
| 11 | 5-[(7R,9aS)-7-(4-chlorophenyl)-7-hydroxy-3,4,6,8,9,9a-hexahydro-1H-pyrido[1,2-a]pyrazine-2-carbonyl]-6- | Intermediate I-2B and 2-chloro-1-methyl-6- | 436.2 |

TABLE 2-continued

| Ex | Name<br>Aspect<br>Purification method | Intermediates | MS,<br>m/z $[M+H]^+$<br>or $[M-H]^-$ |
|---|---|---|---|
| | chloro-l-methylpyridin-2-one<br>yellow amorphous<br>Flash chromatography | oxo-1,6-<br>dihydropyridine-3-<br>carboxylic acid<br>(CAS RN 1007571-57-4) | |
| 12 | 5-[(7S,9aR)-7-(4-chlorophenyl)-7-hydroxy-3,4,6,8,9,9a-hexahydro-1H-pyrido[1,2-a]pyrazine-2-carbonyl]-6-chloro-l-methylpyridin-2-one<br>Off-white amorphous<br>Flash chromatography | Intermediate I-2A<br>and<br>2-chloro-1-methyl-6-oxo-1,6-dihydropyridine-3-carboxylic acid<br>(CAS RN 1007571-57-4) | 436.2 |
| 13 | 3-[3-[(7S,9aR)-7-(4-chlorophenyl)-7-hydroxy-3,4,6,8,9,9a-hexahydro-1H-pyrido[1,2-a]pyrazine-2-carbonyl]-2-chlorophenyl]-1,3-oxazolidin-2-one<br>Colorless amorphous<br>Reversed-phase HPLC | Intermediate I-2A<br>and<br>Intermediate C-1 | 492.1 |
| 14 | 1-[3-[(7S,9aR)-7-(4-chlorophenyl)-7-hydroxy-3,4,6,8,9,9a-hexahydro-1H-pyrido[1,2-a]pyrazine-2-carbonyl]-2-chlorophenyl]imidazolidin-2-one<br>Colorless solid<br>Reversed-phase HPLC | Intermediate I-2A<br>and<br>Intermediate C-2 | 489.2 |
| 15 | [(7S,9aR)-7-(4-chlorophenyl)-7-hydroxy-3,4,6,8,9,9a-hexahydro-1H-pyrido[1,2-a]pyrazin-2-yl]-[2-fluoro-3-(4-methl1-1H-pyrazol-3-yl)phenyl]methanone<br>Colorless solid<br>Reversed-phase HPLC | Intermediate I-2A<br>and<br>Intermediate A-5 | 469.2 |
| 16 | [(7S,9aR)-7-(4-chlorophenyl)-7-hydroxy-3,4,6,8,9,9a-hexahydro-1H-pyrido[1,2-a]pyrazin-2-yl]-[2-chloro-3-(4-methyl-1H-pyrazol-5-yl)phenyl]methanone<br>Colorless amorphous<br>Reversed-phase HPLC | Intermediate I-2A<br>and<br>Intermediate A-4 | 485.2 |
| 17 | [(7S,9aR)-7-(4-chloropheny1)-7-hydroxy-3,4,6,8,9,9a-hexahydro-1H-pyrido[1,2-alpyrazin-2-yl]-[3-(4-methy1-1H-pyrazol-3-yl)phenyllmethanone<br>Colorless solid<br>Reversed-phase HPLC | Intermediate I-2A<br>and<br>Intermediate A-6 | 451.3 |
| 18 | [(7R,9aR)-7-hydroxy-7-[5-(trifluoromethyl)pyridin-2-yl]-3,4,6,8,9,9a-hexahydro-1H-pyrido[1,2-alpyrazin-2-yl]-(2-chloro-3-methoxyphenyl)methanone<br>Colorless amorphous<br>Reversed-phase HPLC | Intermediate I-4A<br>and<br>2-chloro-3-<br>methoxybenzoic acid | 470.2 |
| 19 | [(7S,9aS)-7-hydroxy-7-[5-(trifluoromethyl)pyridin-2-yl]-3,4,6,8,9,9a-hexahydro-1H-pyrido[1,2-a]pyrazin-2-yl]-(2-chloro-3-methoxyphenyl)methanone<br>Off-white solid<br>Reversed-phase HPLC | Intermediate I-4B<br>and<br>2-chloro-3-<br>methoxybenzoic acid | 470.2 |
| 20 | [(7R,9aR)-7-hydroxy-7-[5-(trifluoromethyl)pyridin-2-yl]-3,4,6,8,9,9a-hexahydro-1H-pyrido[1,2-a]pyrazin-2-yl]-[2-chloro-3-(1H-pyrazol-5-yl)phenyl]methanone<br>Colorless amorphous<br>Reversed-phase HPLC | Intermediate I-4A<br>and<br>Intermediate A-3 | 506.3 |
| 21 | [(7S,9aR)-7-(4-chlorophenyl)-7-hydroxy-3,4,6,8,9,9a-hexahydro-1H-pyrido[1,2-a]pyrazin-2-yl]-(2-fluoro-3-morpholino-phenyl)methanone<br>Colorless amorphous<br>Reversed-phase HPLC | Intermediate I-2A<br>and<br>Intermediate A-7 | 474.3 |

TABLE 2-continued

| Ex | Name<br>Aspect<br>Purification method | Intermediates | MS,<br>m/z $[M+H]^+$<br>or $[M-H]^-$ |
|---|---|---|---|
| 22 | tert-butyl 4-[3-[(7S,9aR)-7-(4-chlorophenyl)-7-hydroxy-3,4,6,8,9,9a-hexahydro-1H-pyrido[1,2-a]pyrazine-2-carbonyl]-2-fluorophenyl]piperazine-1-carboxylate<br>Colorless amorphous<br>Flash chromatography | Intermediate I-2A<br>and<br>Intermediate A-8 | 573.4 |
| 27 | [(7R,9aR)-7-(4-chlorophenyl)-1,3,4,6,7,8,9,9a-octahydropyrido[1,2-a]pyrazin-2-yl]-[2-bromo-3-[(Z)-2-phenylethenyl]phenyl]methanone<br>Light brown oil<br>Flash chromatography | Intermediate I-6<br>and<br>Intermediate D1a | 535.1 |
| 28 | [(7R,9aR)-7-(4-chlorophenyl)-1,3,4,6,7,8,9,9a-octahydropyrido[1,2-a]pyrazin-2-yl]-[2-bromo-3-[(E)-2-phenylethenyl]phenyl]methanone<br>Off-white solid<br>Flash chromatography | Intermediate I-6<br>and<br>Intermediate D1b | 535.1 |
| 29 | tert-butyl N-[4-[(E)-2-[3-R7R,9aR)-7-(4-chlorophenyl)-1,3,4,6,7,8,9,9a-octahydropyrido[1,2-a]pyrazine-2-carbonyl]-2-bromophenyl]ethenyl]phenyl]carbamate<br>Off-white solid<br>Flash chromatography | Intermediate I-6<br>and<br>Intermediate D2 | 650.3 |
| 32 | [(7R,9aR)-7-hydroxy-7-[5-(trifluoromethyl)pyridin-2-yl]-3,4,6,8,9,9a-hexahydro-1H-pyrido[1,2-a]pyrazin-2-yl]-[2-chloro-3-(3-hydroxyazetidin-1-yl)phenyl]methanone<br>Colorless amorphous<br>Reversed-phase HPLC | Intermediate I-4A<br>and<br>Intermediate A-1 | 511.3 |
| 33 | [(7S,9aR)-7-(4-chlorophenyl)-7-hydroxy-3,4,6,8,9,9a-hexahydro-1H-pyrido[1,2-a]pyrazin-2-yl]-(2-chloro-3-hydroxyphenyl)methanone<br>Colorless solid<br>Reversed-phase HPLC | Intermediate I-2A<br>and<br>2-Chloro-3-hydroxybenzoic acid<br>(CAS RN 51786-10-8) | 421.2 |
| 34 | 4-(3-((7S,9aR)-7-(4-chlorophenyl)-7-hydroxyoctahydro-2H-pyrido[1,2-a]pyrazine-2-carbonyl)-2-fluorophenyl)piperazin-2-one<br>Off-white foam<br>Reversed-phase HPLC | Intermediate I-2A<br>and<br>Intermediate A-9 | 487.3 |
| 35 | 4-[3-[(7S,9aR)-7-(4-chlorophenyl)-7-hydroxy-3,4,6,8,9,9a-hexahydro-1H-pyrido[1,2-a]pyrazine-2-carbonyl]-2-chlorophenyl]piperazin-2-one<br>Colorless amorphous<br>Reversed-phase HPLC | Intermediate I-2A<br>and<br>Intermediate A-10 | 504.3 |
| 36 | [(7S,9aR)-7-(4-chlorophenyl)-7-hydroxy-3,4,6,8,9,9a-hexahydro-1H-pyrido[1,2-a]pyrazin-2-yl]-[2-chloro-3-(6-oxa-1-azaspiro[3.3]heptan-1-yl)phenyl]methanone<br>Colorless solid<br>Reversed-phase HPLC | Intermediate I-2A<br>and<br>Intermediate A-11 | 503.5 |
| 37 | [(7R,9aR)-7-hydroxy-7-[5-(trifluoromethyl)pyridin-2-yl]-3,4,6,8,9,9a-hexahydro-1H-pyrido[1,2-a]pyrazin-2-yl]-[2-chloro-3-(difluoromethoxy)phenyl]methanone<br>Colorless amorphous<br>Reversed-phase HPLC | Intermediate I-4A<br>and<br>2-Chloro-3-(difluoromethoxy)benzoic acid<br>(CAS RN 1427432-41-4) | 506.4 |
| 38 | [(7S,9aS)-7-hydroxy-7-[5-(trifluoromethyl)pyridin-2-yl]-3,4,6,8,9,9a-hexahydro-1H-pyrido[1,2-a]pyrazin-2-yl]-[2-chloro-3-(difluoromethoxy)phenyl]methanone<br>Colorless amorphous<br>Reversed-phase HPLC | Intermediate I-4B<br>and<br>2-Chloro-3-(difluoromethoxy)benzoic acid<br>(CAS RN 1427432-41-4) | 506.4 |
| 39 | [(7S,9aR)-7-(3-chloro-4-fluorophenyl)-7-hydroxy-3,4,6,8,9,9a-hexahydro-1H-pyrido[1,2-a]pyrazin-2-yl]-[2-fluoro-3- | Intermediate I-3A<br>and<br>Intermediate A-2 | 478.4 |

TABLE 2-continued

| Ex | Name<br>Aspect<br>Purification method | Intermediates | MS,<br>m/z $[M+H]^+$<br>or $[M-H]^-$ |
|---|---|---|---|
| | (3-hydroxyazetidin-1-yl)phenyl]methanone<br>Colorless amorphous<br>Reversed-phase HPLC | | |
| 40 | [(7S,9aR)-7-(3-chloro-4-fluorophenyl)-7-hydroxy-3,4,6,8,9,9a-hexahydro-1H-pyrido[1,2-alpyrazin-2-y1]-[2-chloro-3-(3-hydroxyazetidin-1-yl)phenyl]methanone<br>Colorless solid<br>Flash chromatography | Intermediate I-3A<br>and<br>Intermediate A-1 | 494.2 |
| 41 | [(7R,9aR)-7-hydroxy-7-[5-(trifluoromethyl)pyridin-2-yl]-3,4,6,8,9,9a-hexahydro-1H-pyrido[1,2-a]pyrazin-2-yl]-(2-chloro-3-fluorophenyl)methanone<br>Colorless amorphous<br>Reversed-phase HPLC | Intermediate I-4A<br>and<br>2-Chloro-3-fluorobenzoic acid<br>(CAS RN 102940-86-3) | 458.3 |
| 42 | [(7S,9aS)-7-hydroxy-7-[5-(trifluoromethyl)pyridin-2-yl]-3,4,6,8,9,9a-hexahydro-1H-pyrido[1,2-a]pyrazin-2-yl]-(2-chloro-3-fluorophenyl)methanone<br>Colorless amorphous<br>Reversed-phase HPLC | Intermediate I-4B<br>and<br>2-Chloro-3-fluorobenzoic acid<br>(CAS RN 102940-86-3) | 458.3 |
| 43 | [(7S,9aR)-7-(3-chloro-4-fluorophenyl)-7-hydroxy-3,4,6,8,9,9a-hexahydro-1H-pyrido[1,2-a]pyrazin-2-yl]-[2-chloro-3-[(3S)-3-hydroxypyrrolidin-1-yl]phenyl]methanone<br>Yellow solid<br>Flash chromatography | Intermediate I-3A<br>and<br>Intermediate A-12 | 508.3 |
| 44 | [(7S,9aR)-7-(3-chloro-4-fluorophenyl)-7-hydroxy-3,4,6,8,9,9a-hexahydro-1H-pyrido[1,2-a]pyrazin-2-yl]-[2-chloro-3-[(3R)-3-hydroxypyrrolidin-1-yl]phenyl]methanone<br>Yellow solid<br>Flash chromatography | Intermediate I-3A<br>and<br>Intermediate A-13 | 508.3 |
| 45 | [(7S,9aR)-7-(4-chlorophenyl)-7-hydroxy-3,4,6,8,9,9a-hexahydro-1H-pyrido[1,2-a]pyrazin-2-yl]-[2-chloro-3-[(3R)-3 -hydroxypyrrolidin-1 -yl]phenyl]methanone<br>Colorless solid<br>Reversed-phase HPLC | Intermediate I-2A<br>and<br>Intermediate A-13 | 490.3 |
| 46 | [(7S,9aR)-7-(4-chlorophenyl)-7-hydroxy-3,4,6,8,9,9a-hexahydro-1H-pyrido[1,2-a]pyrazin-2-yl]-[2-chloro-3-(3-hydroxy-3-methylazetidin-1-yl)phenyl]methanone<br>Colorless amorphous<br>Reversed-phase HPLC | Intermediate I-2A<br>and<br>Intermediate A-14 | 490.3 |
| 47 | [(7S,9aR)-7-(3-chloro-4-fluorophenyl)-7-hydroxy-3,4,6,8,9,9a-hexahydro-1H-pyrido[1,2-a]pyrazin-2-yl]-[2-chloro-3-[(3S)-3-hydroxypiperidin-1-yl]phenyl]methanone<br>Yellow solid<br>Reversed-phase HPLC | Intermediate I-3A<br>and<br>Intermediate A-15 | 522.3 |
| 48 | [(7S,9aR)-7-(3-chloro-4-fluorophenyl)-7-hydroxy-3,4,6,8,9,9a-hexahydro-1H-pyrido[1,2-a]pyrazin-2-yl]-[2-chloro-3-[(3R)-3-hydroxypiperidin-1 -yl]phenyl]methanone<br>Yellow solid<br>Reversed-phase HPLC | Intermediate I-3A<br>and<br>Intermediate A-16 | 522.3 |
| 49 | [(7S,9aR)-7-(4-chlorophenyl)-7-hydroxy-3,4,6,8,9,9a-hexahydro-1H-pyrido[1,2-a]pyrazin-2-yl]-[2-chloro-3-(4-hydroxypiperidin-1-yl)phenyl]methanone<br>Colorless amorphous<br>Flash chromatography | Intermediate I-2A<br>and<br>Intermediate A-17 | 504.3 |
| 50 | [2-chloro-3-(3-hydroxy-3-methylpyrrolidin-1-yl)phenyl]-[rac- | Intermediate I-2A<br>and | 504.3 |

TABLE 2-continued

| Ex | Name<br>Aspect<br>Purification method | Intermediates | MS,<br>m/z $[M+H]^+$<br>or $[M-H]^-$ |
|---|---|---|---|
| | (7R,9aS)-7-(4-chlorophenyl)-7-hydroxy-3,4,6,8,9,9a-hexahydro-1H-pyrido[1,2-a]pyrazin-2-yl]methanone<br>Colorless amorphous<br>Reversed-phase HPLC | Intermediate A-18 | |
| 51 | [(7S,9aR)-7-(3-chloro-4-fluorophenyl)-7-hydroxy-3,4,6,8,9,9a-hexahydro-1H-pyrido[1,2-a]pyrazin-2-yl]-[2-chloro-3-[(3S,4S)-3,4-dihydroxypyrrolidin-1-yl]phenyl]methanone<br>Colorless foam<br>Reversed-phase HPLC | Intermediate I-3A and Intermediate A-19 | 524.1 |
| 52 | [(7S,9aR)-7-(3-chloro-4-fluorophenyl)-7-hydroxy-3,4,6,8,9,9a-hexahydro-1H-pyrido[1,2-a]pyrazin-2-yl]-[2-chloro-3-[3-fluoro-3-(hydroxymethyl)azetidin-1-yl]phenyl]methanone<br>Colorless amorphous<br>Reversed-phase HPLC | Intermediate I-3A and Intermediate A-20 | 526.2 |
| 53 | [(7S,9aR)-7-(3-chloro-4-fluorophenyl)-7-hydroxy-3,4,6,8,9,9a-hexahydro-1H-pyrido[1,2-a]pyrazin-2-yl]-[2-chloro-3-[3-(hydroxymethyl)azetidin-1-yl]phenyl]methanone<br>Colorless amorphous<br>Reversed-phase HPLC | Intermediate I-3A and Intermediate A-21 | 508.3 |
| 54 | [(7S,9aR)-7-(3-chloro-4-fluorophenyl)-7-hydroxy-3,4,6,8,9,9a-hexahydro-1H-pyrido[1,2-a]pyrazin-2-yl]-[2-chloro-3-(1H-pyrazol-3-yl)phenyl]methanone<br>Colorless amorphous<br>Reversed-phase HPLC | Intermediate I-3A and Intermediate A-3 | 489.3 |
| 55 | [(7S,9aR)-7-(3-chloro-4-fluorophenyl)-7-hydroxy-3,4,6,8,9,9a-hexahydro-1H-pyrido[1,2-a]pyrazin-2-yl]-[2-fluoro-3-(1H-pyrazol-3-yl)phenyl]methanone<br>Colorless amorphous<br>Reversed-phase HPLC | Intermediate I-3A and Intermediate A-22 | 473.3 |
| 56 | [(7S,9aR)-7-(4-chlorophenyl)-7-hydroxy-3,4,6,8,9,9a-hexahydro-1H-pyrido[1,2-a]pyrazin-2-yl]-[2-fluoro-3-(1,2-thiazol-3-yl)phenyl]methanone<br>Colorless solid<br>Reversed-phase HPLC | Intermediate I-2A and Intermediate B-2 | 472.3 |
| 57 | [(7S,9aR)-7-(3-chloro-4-fluorophenyl)-7-hydroxy-3,4,6,8,9,9a-hexahydro-1H-pyrido[1,2-a]pyrazin-2-yl]-[2-chloro-3-(4-fluoro-1H-pyrazol-5-yl)phenyl]methanone<br>Colorless solid<br>Reversed-phase HPLC | Intermediate I-3A and Intermediate B-3 | 507.3 |
| 58 | [(7S,9aR)-7-(3-chloro-4-fluorophenyl)-7-hydroxy-3,4,6,8,9,9a-hexahydro-1H-pyrido[1,2-a]pyrazin-2-yl]-[2-chloro-3-(1,2,4-thiadiazol-3-yl)phenyl]methanone<br>Yellow solid<br>Reversed-phase HPLC | Intermediate I-3A and Intermediate B-6 | 507.3 |
| 59 | [(7S,9aR)-7-(3,4-difluorophenyl)-7-hydroxy-3,4,6,8,9,9a-hexahydro-1H-pyrido[1,2-a]pyrazin-2-yl]-(2-chloro-3-methoxyphenyl)methanone<br>Colorless foam<br>Reversed-phase HPLC | Intermediate I-10A and 2-chloro-3-methoxybenzoic acid | 437.2 |
| 60 | [(7R,9aS)-7-(3,4-difluorophenyl)-7-hydroxy-3,4,6,8,9,9a-hexahydro-1H-pyrido[1,2-a]pyrazin-2-yl]-(2-chloro-3-methoxyphenyl)methanone<br>Colorless foam<br>Reversed-phase HPLC | Intermediate I-10B and 2-chloro-3-methoxybenzoic acid | 437.2 |
| 61 | [(7S,9aR)-7-(3,4-difluorophenyl)-7-hydroxy-3,4,6,8,9,9a-hexahydro-1H-pyrido[1,2-a]pyrazin-2-yl]-[2-fluoro-3-(1H-pyrazol-5-yl)phenyl]methanone<br>Colorless solid<br>Reversed-phase HPLC | Intermediate I-10A and Intermediate B-4 | 457.2 |

TABLE 2-continued

| Ex | Name<br>Aspect<br>Purification method | Intermediates | MS,<br>m/z $[M+H]^+$<br>or $[M-H]^-$ |
|---|---|---|---|
| 62 | [(7S,9aR)-7-(3,4-difluorophenyl)-7-hydroxy-3,4,6,8,9,9a-hexahydro-1H-pyrido[1,2-a]pyrazin-2-yl]-[2-fluoro-3-(4-fluoro-1H-pyrazol-5-yl)phenyl]methanone<br>Colorless oil<br>Flash chromatography | Intermediate I-10A and Intermediate B-5 | 475.2 |
| 63 | [(7S,9aR)-7-(3,4-difluorophenyl)-7-hydroxy-3,4,6,8,9,9a-hexahydro-1H-pyrido[1,2-a]pyrazin-2-yl]-[2-chloro-3-(3-hydroxyazetidin-1-yl)phenyl]methanone<br>Colorless amorphous<br>Reversed-phase HPLC | Intermediate I-10A and Intermediate A-2 | 478.2 |
| 64 | [7R,9aR)-7-hydroxy-7-[5-(trifluoromethyppyridin-2-ylrvrac-3,4,6,8,9,9a-hexahydro-1H-pyrido[1,2-a]pyrazin-2-yl]-[2-chloro-3-(4-fluoro-1H-pyrazol-5-yl)phenyl]methanone<br>Colorless foam<br>Reversed-phase HPLC | Intermediate I-4A and Intermediate B-3 | 524.2 |

Example 23

[(7S,9aR)-7-(4-chlorophenyl)-7-hydroxy-3,4,6,8,9,9a-hexahydro-1H-pyrido[1,2-a]pyrazin-2-yl]-(2-fluoro-3-piperazin-1-ylphenyl)methanone To a solution of tert-butyl 4-[3-[(7S,9aR)-7-(4-chlorophenyl)-7-hydroxy-3,4,6,8,9,9a-hexahydro-1H-pyrido[1,2-a]pyrazine-2-carbonyl]-2-fluorophenyl]piperazine-1-carboxylate (Example 22, 0.023 g, 0.040 mmol) in DCM (0.5 mL) was added TFA (0.047 mL, 0.607 mmol) and the reaction mixture was stirred at room temperature for 6 hours. The mixture was concentrated in vacuo, the residue taken up in EtOAc, poured into a saturated aq. $NaHCO_3$ solution and the aqueous layer was extracted with EtOAc. Combined organics were washed with brine, dried over $Na_2SO_4$, filtered and evaporated to dryness to give the crude title compound (0.017 g, 82%) as yellow solid; MS (ESI): m/z=473.3 $[M+H]^+$.

Example 24

(2-Chloro-3-methoxyphenyl)-[rac-(7R,9aS)-7-hydroxy-7-(2-methylpropyl)-3,4,6,8,9,9a-hexahydro-1H-pyrido[1,2-a]pyrazin-2-yl]methanone A suspension of cerium (III) chloride (0.092 g, 0.372 mmol) in THF (1 mL) was stirred at room temperature for 1.5 hours. The mixture was cooled to 0° C. with an ice bath, a 2M solution of isobutylmagnesium bromide in THF (0.155 mL, 0.310 mmol) was added dropwise and stirring was continued at this temperature for 1 hour. Then, a solution of 2-(2-chloro-3-methoxybenzoyl)-3,4,6,8,9,9a-hexahydro-1H-pyrido[1,2-a]pyrazin-7-one (Intermediate I-5, 0.100 g, 0.310 mmol) in THF (0.3 mL) was added and the reaction mixture was stirred at 0° C. for 30 minutes. The mixture was quenched with water, filtered over Dicalite and washed with EtOAc. The resulting solution was dried over $Na_2SO_4$, filtered and concentrated in vacuo. The residue was purified by reversed-phase HPLC to give the title compound (0.014, 12%) as amorphous colorless solid; MS (ESI): m/z=381.3 $[M+H]^+$.

Example 25

(2-chloro-3-methoxyphenyl)-[rac-(7R,9aS)-7-cyclopentyl-7-hydroxy-3,4,6,8,9,9a-hexahydro-1H-pyrido[1,2-a]pyrazin-2-yl]methanone was prepared in analogy to example 24, but using a 1M solution of cyclopentylmagnesium bromide in THF to give the title compound as a light yellow amorphous solid; MS (ESI): m/z=393.3 $[M+H]^+$.

Example 26

(2-Chloro-3-methoxyphenyl)-[rac-(7R,9aR)-7-hydroxy-7-(trifluoromethyl)-3,4,6,8,9,9a-hexahydro-1H-pyrido[1,2-a]pyrazin-2-yl]methanone In a 3 necked round bottom flask, a solution of 2-(2-chloro-3-methoxybenzoyl)-3,4,6,8,9,9a-hexahydro-1H-pyrido[1,2-a]pyrazin-7-one (Intermediate I-5, 0.1 g, 0.310 mmol) in THF (1.7 mL) was cooled to −5° C. with an ice-salt bath. Trimethyl(trifluoromethyl)silane (0.055 mL, 0.372 mmol) was added, then after 10 minutes a 1M solution of TBAF (0.310 mL, 0.310 mmol) in THF was added to the mixture while keeping the temperature below 2° C. The reaction mixture was stirred at 0° C. for another 10 minutes and then allowed to warm up to room temperature and stirring was continued for 2 hours. The mixture was quenched with a sat. $NH_4Cl$. aq. solution and the mixture diluted with EtOAc. The organic layer was washed with water, brine, dried over $Na_2SO_4$ and concentrated in vacuo. The residue was purified by silica gel flash chromatography, eluting with a 50 to 100% EtOAc-heptane gradient to give the title compound (0.022 g, 18%) as a colorless solid; MS (ESI): m/z=393.2 $[M+H]^+$.

Example 30

N-[4-[(E)-2-[3-[(7R,9aR)-7-(4-chlorophenyl)-1,3,4,6,7,8,9,9a-octahydropyrido[1,2-a]pyrazine-2-carbonyl]-2-bromophenyl]ethenyl]phenyl]prop-2-enamide Step [A] [(7R,9aR)-7-(4-chlorophenyl)-1,3,4,6,7,8,9,9a-octahydropyrido[1,2-a]pyrazin-2-yl]-[3-[(E)-2-(4-aminophenyl)vinyl]-2-bromo-phenyl]methanone To a solution of tert-butyl N-[4-[(E)-2-[3-[(7R,9aR)-7-(4-chlorophenyl)-1,3,4,6,7,8,9,9a-octahydropyrido[1,2-a]pyrazine-2-carbonyl]-2-bromophenyl]ethenyl]phenyl]carbamate (Example 29, 0.007 g, 0.011 mmol) in DCM (0.5 mL) was added TFA (0.017 mL, 0.222 mmol) and the reaction mixture was stirred at room temperature for 18 hours. The mixture was concentrated in vacuo, the residue taken up in EtOAc and washed with a sat. $NaHCO_3$ aqueous solution. The organic layer was washed with brine, dried over $Na_2SO_4$, filtered and evaporated to dryness to give the crude title compound (0.008 g) as yellow solid; MS (ESI): m/z=550.1 $[M+H]^+$.

Step [B] N-[4-[(E)-2-[3-[(7R,9aR)-7-(4-chlorophenyl)-1,3,4,6,7,8,9,9a-octahydropyrido[1,2-a]pyrazine-2-carbonyl]-2-bromophenyl]ethenyl]phenyl] prop-2-enamide To a solution of [(7R,9aR)-7-(4-chlorophenyl)-1,3,4,6,7,8,9,9a-octahydropyrido[1,2-a]pyrazin-2-yl]-[3-[(E)-2-(4-aminophenyl)vinyl]-2-bromo-phenyl]methanone (0.008 g, 0.015 mmol) and acrylic acid (0.001 g, 0.015 mmol) in DMF (0.2 mL) was added Hunig's base (0.008 mL, 0.046 mmol) followed by HATU (0.006 g, 0.017 mmol) and the reaction mixture was stirred at room temperature for 15 hours. The mixture was diluted with EtOAc, washed with water, brine, dried over $Na_2SO_4$, filtered, and concentrated in vacuo. The residue was purified by reversed phase HPLC to give the title compound (0.005 g, 5%) as colorless amorphous; MS (ESI): m/z=604.7 $[M+H]^+$.

Example 31

4-[(E)-2-[3-[(7R,9aR)-7-(4-Chlorophenyl)-1,3,4,6,7,8,9,9a-octahydropyrido[1,2-a]pyrazine-2-carbonyl]-2-bromo-phenyl]vinyl]-N-methyl-benzamide and 3-[(E)-2-[4-[(7R,9aR)-7-(4-chlorophenyl)-1,3,4,6,7,8,9,9a-octahydropyrido[1,2-a]pyrazine-2-carbonyl] phenyl]vinyl]-2-bromo-N-methyl-benzamide To a solution of 2-bromo-3-[(E)-2-(4-carboxyphenyl)vinyl]benzoic acid (intermediate D-3, 0.04 g, 0.115 mmol) in DMF (0.5 mL) was added Hünig's base (0.05 mL, 0.288 mmol) and the mixture was stirred at room temperature for 1 hour. Then, a mixture of methanamine hydrochloride (0.008 g, 0.115 mmol) and (7R,9aR)-7-(4-Chlorophenyl) octahydro-1H-pyrido[1,2-a]pyrazine (Intermediate I-6, 0.029 g, 0.115 μmol) in DMF (0.5 mL)/Hunig's base (0.05 mL) was added dropwise and the reaction mixture was stirred at room temperature for 18 hours. Water was added to the mixture which was then stirred in an ultrasonic batch. The resulting precipitate was filtered off, collected, poured into a 1M aq. $Na_2CO_3$ solution and the aqueous layer was extracted with DCM. The organic layers were combined, dried over $Na_2SO_4$, filtered and concentrated in vacuo. The residue was purified by silica gel flash chromatography, eluting with a 0 to 5% MeOH-DCM gradient to give the title compounds (0.032 g, 44%) as a 1:1 mixture of isomers as off-white solid; MS (ESI): m/z=592.2 $[M+H]^+$.

Example 65

[(7S,9aR)-7-(3-chloro-4-fluorophenyl)-7-hydroxy-3,4,6,8,9,9a-hexahydro-1H-pyrido[1,2-a]pyrazin-2-yl]-(2,3-dihydro-1H-indol-4-yl)methanone Step [A] tert-butyl 4-[(7S,9aR)-7-(3-chloro-4-fluorophenyl)-7-hydroxy-3,4,6,8,9,9a-hexahydro-1H-pyrido[1,2-a]pyrazine-2-carbonyl]-2,3-dihydroindole-1-carboxylate was prepared in analogy to example 1, but using (7S,9aR)-7-(3-chloro-4-fluoro-phenyl)-1,2,3,4,6,8,9,9a-octahydropyrido[1,2-a]pyrazin-7-ol (Intermediate I-3A) and 1-tert-butoxycarbonylindoline-4-carboxylic acid (CAS RN 208774-11-2) to give the title compound as a colorless foam; MS (ESI): m/z=530.4 $[M+H]^+$.

Step [B] [(7S,9aR)-7-(3-chloro-4-fluorophenyl)-7-hydroxy-3,4,6,8,9,9a-hexahydro-1H-pyrido[1,2-a]pyrazin-2-yl]-(2,3-dihydro-1H-indol-4-yl)methanone To a solution of tert-butyl 4-[(7S,9aR)-7-(3-chloro-4-fluorophenyl)-7-hydroxy-3,4,6,8,9,9a-hexahydro-1H-pyrido[1,2-a]pyrazine-2-carbonyl]-2,3-dihydroindole-1-carboxylate (0.03 g, 0.057 mmol) in DCM (0.5 mL) was added TFA (0.087 mL, 1.13 mmol) and the reaction mixture was stirred at room temperature for 2 hours. The mixture was added dropwise to a sat. aq. $NaHCO_3$ (5 mL) solution and the aqueous phase was extracted with DCM. Combined organics were dried over $Na_2SO_4$, filtered and evaporated to dryness to give the title compound (0.007 g, 29%) as colorless foam; MS (ESI): m/z=430.3 $[M+H]^+$.

Example 66

[(7S,9aR)-7-(4-chlorophenyl)-7-hydroxy-3,4,6,8,9,9a-hexahydro-1H-pyrido[1,2-a]pyrazin-2-yl]-[4-chloro-5-(1H-pyrazol-3-yl)pyridin-3-yl]methanone In a sealed tube [(7S,9aR)-7-(4-chlorophenyl)-7-hydroxy-3,4,6,8,9,9a-hexahydro-1H-pyrido[1,2-a]pyrazin-2-yl]-(5-bromo-4-chloropyridin-3-yl)methanone (Intermediate I-9, 0.023 g, 0.048 mmol), tert-butyl 3-(4,4,5,5-tetramethyl-1,3,2-dioxaborolan-2-yl)-1H-pyrazole-1-carboxylate (CAS RN 1256359-17-7, 0.017 g, 0.058 mmol) and bis(triphenylphosphine)palladium (II) chloride (0.004 g, 0.005 mmol) were dissolved in DMF (0.25 mL). The reaction mixture was purged with Argon. Then, a 1M aqueous solution of $Na_2CO_3$ (0.145 mL, 0.145 mmol) was added and the reaction mixture heated to 90° C. overnight. The mixture was diluted with EtOAc, poured into water and the aqueous layer was extracted with EtOAc. Combined organics were washed with brine, dried over $Na_2SO_4$, filtered and concentrated in vacuo. The residue was purified by reversed phase HPLC to give the title compound (0.003 g, 12%) as a colorless solid; MS (ESI): m/z=472.4 $[M+H]^+$.

Example 67

[(7S,9aR)-7-(4-chlorophenyl)-7-hydroxy-3,4,6,8,9,9a-hexahydro-1H-pyrido[1,2-a]pyrazin-2-yl]-[2-chloro-3-(1,2-thiazol-3-yl)phenyl]methanone In a microwave vial, [3-[(7S,9aR)-7-(4-chlorophenyl)-7-hydroxy-3,4,6,8,9,9a-hexahydro-1H-pyrido[1,2-a]pyrazine- 2-carbonyl]-2-chloro-phenyl]boronic acid (Intermediate I-7, 0.03 g, 0.067 mmol), 3-bromoisothiazole (CAS RN 55512-82-8, 0.01 g, 0.061 mmol), bis(di-tert-butyl(4-dimethylaminophenyl)phosphine)dichloropalladium(II) (CAS RN 887919-35-9, 0.004 g, 0.006 mmol) and $K_2CO_3$ (0.025 g, 0.183 mmol) were mixed in dioxane (1.72 mL) and water (0.440 mL). The mixture was degassed with Argon and heated in the microwave to 90° C. for 15 minutes. The mixture was diluted with EtOAc, washed with water and brine. The organics layer was dried over $Na_2SO_4$, filtered and concentrated in vacuo. The residue was purified by reversed phase HPLC to give the title compound (0.005 g, 16%) as a colorless amorphous solid; MS (ESI): m/z=488.3 $[M+H]^+$.

Example 68

[(7S,9aR)-7-(4-chlorophenyl)-7-hydroxy-3,4,6,8,9,9a-hexahydro-1H-pyrido[1,2-a]pyrazin-2-yl]-[2-chloro-3-(1,2-thiazol-4-yl)phenyl]methanone was prepared in analogy to example 67, but using 4-bromoisothiazole (CAS RN 24340-77-0) to give the title compound as a colorless amorphous solid; MS (ESI): m/z=488.3 $[M+H]^+$.

Example 69

[(7R,9aR)-7-hydroxy-7-[5-(trifluoromethyl)pyridin-2-yl]-3,4,6,8,9,9a-hexahydro-1H-pyrido[1,2-a]pyrazin-2-yl]-[2-chloro-3-(1,2-thiazol-3-yl)phenyl]methanone was prepared in analogy to example 67, but using 2-chloro-3-((7R,9aR)-7-hydroxy-7-(5-(trifluoromethyl)pyridin-2-yl)octahydro-2H-pyrido[1,2-a]pyrazine-2-carbonyl)phenyl)boronic acid (Intermediate I-8) and bromoisothiazole (CAS RN 55512-82-8) to give the title compound as a colorless amorphous solid; MS (ESI): m/z=523.3 $[M+H]^+$.

Example 70

[(7S,9aR)-7-(4-chlorophenyl)-7-hydroxy-3,4,6,8,9,9a-hexahydro-1H-pyrido[1,2-a]pyrazin-2-yl]-[4-methyl-5-(1H-pyrazol-3-yl)pyridin-3-yl]methanone was prepared in analogy to example 66, but using [(7S,9aR)-7-(4-chlorophenyl)-7-hydroxy-3,4,6,8,9,9a-hexahydro-1H-pyrido[1,2-a]pyrazin-2-yl]-(5-bromo-4-methylpyridin-3-yl)methanone (Intermediate I-11) to give the title compound as a colorless foam; MS (ESI): m/z=452.3 $[M+H]^+$.

Example 71 and 72

(2-chloro-3-methoxyphenyl)-[rac-(7R,9aR)-7-hydroxy-7-[6-(trifluoromethyl)pyridin-3-yl]-3,4,6,8,9,9a-hexahydro-1H-pyrido[1,2-a]pyrazin-2-yl]methanone and (2-chloro-3-methoxyphenyl)-[rac-(7R,9aS)-7-hydroxy-7-[6-(trifluoromethyl)pyridin-3-yl]-3,4,6,8,9,9a-hexahydro-1H-pyrido[1,2-a]pyrazin-2-yl]methanone To a suspension of 5-bromo-2-(trifluoromethyl)pyridine (CAS RN 436799-32-5, 0.12 g, 0.531 mmol) in toluene (4.2 mL) cooled to −78° C. was added a 1.6M solution of n-BuLi in hexanes (0.398 mL, 0.637 mmol) and the mixture stirred at this temperature for 5 minutes. Then, a solution of 2-(2-chloro-3-methoxybenzoyl)-3,4,6,8,9,9a-hexahydro-1H-pyrido[1,2-a]pyrazin-7-one (Intermediate I-5, 0.189 g, 0.584 mmol) was added dropwise at −78° C. and the reaction mixture stirred at this temperature for 3 hours. The mixture was quenched at −78° C. by addition of a sat. aq. $NH_4Cl$ solution and extracted with EtOAc. Combined organics were washed $H_2O$, brine, dried over $Na_2SO_4$, filtered and evaporated. The crude material was purified by silica gel flash chromatography, eluting with a 20 to 60% EtOAc in heptane gradient to give respectively (2-chloro-3-methoxyphenyl)-[rac-(7R,9aR)-7-hydroxy-7-[6-(trifluoromethyl)pyridin-3-yl]-3,4,6,8,9,9a-hexahydro-1H-pyrido[1,2-a]pyrazin-2-yl]methanone (example 71, 0.006 g, 2.4%) and 65 mg of less pure material containing the Trans compounds. This residue was purified by reversed-phase HPLC to give (2-chloro-3-methoxyphenyl)-[rac-(7R,9aS)-7-hydroxy-7-[6-(trifluoromethyl)pyridin-3-yl]-3,4,6,8,9,9a-hexahydro-1H-pyrido[1,2-a]pyrazin-2-yl]methanone (Example 72, 0.004 g, 1.8%) as colorless amorphous solids; MS (ESI): m/z=470.3 $[M+H]^+$.

Example 73

A compound of formula (I) can be used in a manner known per se as the active ingredient for the production of tablets of the following composition:

| | Per tablet |
|---|---|
| Active ingredient | 200 mg |
| Microcrystalline cellulose | 155 mg |
| Corn starch | 25 mg |
| Talc | 25 mg |
| Hydroxypropylmethylcellulose | 20 mg |
| | 425 mg |

Example 74

A compound of formula (I) can be used in a manner known per se as the active ingredient for the production of capsules of the following composition:

| | Per capsule |
|---|---|
| Active ingredient | 100.0 mg |
| Corn starch | 20.0 mg |
| Lactose | 95.0 mg |
| Talc | 4.5 mg |
| Magnesium stearate | 0.5 mg |
| | 220.0 mg |

The invention claimed is:

1. A compound of formula (I):

(I)

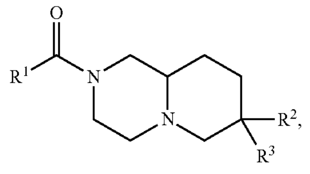

or a pharmaceutically acceptable salt thereof, wherein:

$R^1$ is selected from the group consisting of:

(i) $C_6$-$C_{14}$-aryl optionally substituted with 1-2 substituents independently selected from the group consisting of $C_{1-6}$-alkoxy, halogen, and a group

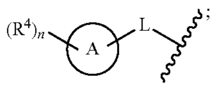

(ii) 5- to 6-membered heteroaryl optionally substituted with 1-2 substituents independently selected from the group consisting of halogen, $C_{1-6}$-alkoxy, $C_{1-6}$-alkyl, and amino; and (iii) 5- to 14-membered heterocyclyl optionally substituted with 1-3 substituents independently selected from the group consisting of halogen, $C_{1-6}$-alkyl, and OXO;

$R^2$ is selected from the group consisting of:

(i) $C_{1-6}$-alkyl substituted with 1-3 substituents independently selected from halogen;

(ii) $C_{3-14}$-cycloalkyl; and (iii) 5- to 14-membered heteroaryl optionally substituted with 1-3 substituents independently selected from halogen, $C_{1-6}$-alkyl, halo-$C_{1-6}$-alkyl, and oxo;

$R^3$ is selected from the group consisting of hydrogen, halogen, $C_{1-6}$-alkoxy, $C_{3-14}$-cycloalkyloxy, and hydroxy;

$R^4$ is selected from the group consisting of hydrogen, halogen, $C_{1-6}$-alkyl, $C_{1-6}$-alkoxycarbonyl, $C_{1-6}$-alkoxycarbonyl-NH—, hydroxy, amino, carboxy, $C_{1-6}$-alkyl-C(O)—NH—, $C_{2-6}$-alkenyl-C(O)—NH—, carboxy-NH—, oxo, $C_{3-14}$-cycloalkyl, and hydroxy-$C_{3-14}$-cycloalkyl;

L is selected from the group consisting of a covalent bond and —CH═CH—;

A is selected from the group consisting of $C_6$-$C_{14}$-aryl, 5- to 14-membered heteroaryl, and 4- to 14-membered heterocyclyl; and n is 1, 2, 3, or 4.

2. The compound of claim 1, or a pharmaceutically acceptable salt thereof, wherein:

$R^4$ is selected from the group consisting of hydrogen, halogen, $C_{1-6}$-alkyl, $C_{1-6}$-alkoxycarbonyl, $C_{1-6}$-alkoxycarbonyl-NH—, hydroxy and oxo; and n is 1 or 2.

3. The compound of claim 1, or a pharmaceutically acceptable salt thereof, wherein:

$R^1$ is $C_6$-$C_{14}$-aryl substituted with 1-2 substituents independently selected from the group consisting of $C_{1-6}$-alkoxy, halogen, and a group

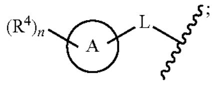

$R^4$ is selected from the group consisting of hydrogen, halogen, and hydroxy;

L is a covalent bond;

A is selected from the group consisting of 5- to 14-membered heteroaryl and 4- to 14-membered heterocyclyl; and n is 1 or 2.

4. The compound of claim 1, or a pharmaceutically acceptable salt thereof, wherein:

$R^1$ is phenyl substituted with 1-2 substituents independently selected from the group, consisting of chloro, fluoro, methoxy and a group

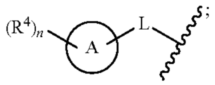

$R^4$ is selected from the group consisting of hydrogen, fluoro, and hydroxy;

L is a covalent bond;

A is selected from the group consisting of pyrazolyl and azetidinyl; and n is 1 or 2.

5. The compound of claim 1, or a pharmaceutically acceptable salt thereof, wherein $R^2$ is selected from the group consisting of:

(i) $C_{1-6}$-alkyl substituted with 1-3 substituents independently selected from halogen;

(ii) $C_{3-14}$-cycloalkyl; and (iii) 5- to 14-membered heteroaryl substituted with halo-$C_{1-6}$-alkyl.

6. The compound of claim 1, or a pharmaceutically acceptable salt thereof, wherein $R^2$ is 5- to 14-membered heteroaryl substituted with halo-$C_{1-6}$-alkyl.

7. The compound of claim 1, or a pharmaceutically acceptable salt thereof, wherein $R^2$ is pyridyl substituted with $CF_3$.

8. The compound of claim 1, or a pharmaceutically acceptable salt thereof, wherein $R^3$ is hydrogen or hydroxy.

9. The compound of claim 1, or a pharmaceutically acceptable salt thereof, wherein $R^3$ is hydroxy.

10. The compound of claim 1, or a pharmaceutically acceptable salt thereof, wherein:

$R^1$ is $C_6$-$C_{14}$-aryl substituted with 1-2 substituents independently selected from the group consisting of $C_{1-6}$-alkoxy, halogen, and a group

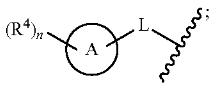

$R^2$ is 5- to 14-membered heteroaryl substituted with halo-$C_{1-6}$-alkyl;

$R^4$ is selected from the group consisting of hydrogen, halogen, and hydroxy;

L is a covalent bond;

A is selected from the group consisting of 5- to 14-membered heteroaryl and 4- to 14-membered heterocyclyl; and n is 1 or 2.

11. The compound of claim 1, or a pharmaceutically acceptable salt thereof, wherein:

$R^1$ is phenyl substituted with 1-2 substituents independently selected from the group consisting of chloro, fluoro, methoxy and a group

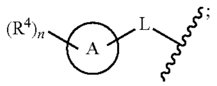

$R^2$ pyridyl substituted with $CF_3$;
$R^4$ is selected from the group consisting of hydrogen, fluoro, and hydroxy;
L is a covalent bond;
A is selected from the group consisting of pyrazolyl and azetidinyl; and
n is 1 or 2.

12. A compound selected from the group consisting of:
[(7S,9aR)-7-(3-chloro-4-fluorophenyl)-7-hydroxy-3,4,6,8,9,9a-hexahydro-1H-pyrido[1,2-a]pyrazin-2-yl]-(2-chloro-3-methoxyphenyl)methanone;
[(7R,9aS)-7-(3-chloro-4-fluorophenyl)-7-hydroxy-3,4,6,8,9,9a-hexahydro-1H-pyrido[1,2-a]pyrazin-2-yl]-(2-chloro-3-methoxyphenyl)methanone;
[(7S,9aR)-7-(4-chlorophenyl)-7-hydroxy-3,4,6,8,9,9a-hexahydro-1H-pyrido[1,2-a]pyrazin-2-yl]-[2-chloro-3-(1H-pyrazol-5-yl)phenyl]methanone;
[(7R,9aS)-7-(4-chlorophenyl)-7-hydroxy-3,4,6,8,9,9a-hexahydro-1H-pyrido[1,2-a]pyrazin-2-yl]-[2-chloro-3-(1H-pyrazol-5-yl)phenyl]methanone;
[(7S,9aR)-7-(4-chlorophenyl)-7-hydroxy-3,4,6,8,9,9a-hexahydro-1H-pyrido[1,2-a]pyrazin-2-yl]-[2-chloro-3-(3-fluoro-1H-pyrazol-4-yl)phenyl]methanone;
[(7R,9aS)-7-(4-chlorophenyl)-7-hydroxy-3,4,6,8,9,9a-hexahydro-1H-pyrido[1,2-a]pyrazin-2-yl]-[2-chloro-3-(3-fluoro-1H-pyrazol-4-yl)phenyl]methanone;
[(7S,9aR)-7-(4-chlorophenyl)-7-hydroxy-3,4,6,8,9,9a-hexahydro-1H-pyrido[1,2-a]pyrazin-2-yl]-(2-chloro-6-methoxypyridin-3-yl)methanone;
[(7S,9aR)-7-(4-chlorophenyl)-7-hydroxy-3,4,6,8,9,9a-hexahydro-1H-pyrido[1,2-a]pyrazin-2-yl]-(6-amino-2-methylpyridin-3-yl)methanone;
[(7S,9aR)-7-(4-chlorophenyl)-7-hydroxy-3,4,6,8,9,9a-hexahydro-1H-pyrido[1,2-a]pyrazin-2-yl]-[2-chloro-3-(3-hydroxyazetidin-1-yl)phenyl]methanone;
[(7S,9aR)-7-(4-chlorophenyl)-7-hydroxy-3,4,6,8,9,9a-hexahydro-1H-pyrido[1,2-a]pyrazin-2-yl]-[2-fluoro-3-(3-hydroxyazetidin-1-yl)phenyl]methanone;
5-[(7R,9aS)-7-(4-chlorophenyl)-7-hydroxy-3,4,6,8,9,9a-hexahydro-1H-pyrido[1,2-a]pyrazine-2-carbonyl]-6-chloro-1-methylpyridin-2-one;
5-[(7S,9aR)-7-(4-chlorophenyl)-7-hydroxy-3,4,6,8,9,9a-hexahydro-1H-pyrido[1,2-a]pyrazine-2-carbonyl]-6-chloro-1-methylpyridin-2-one;
3-[3-[(7S,9aR)-7-(4-chlorophenyl)-7-hydroxy-3,4,6,8,9,9a-hexahydro-1H-pyrido[1,2-a]pyrazine-2-carbonyl]-2-chlorophenyl]-1,3-oxazolidin-2-one;
1-[3-[(7S,9aR)-7-(4-chlorophenyl)-7-hydroxy-3,4,6,8,9,9a-hexahydro-1H-pyrido[1,2-a]pyrazine-2-carbonyl]-2-chlorophenyl]imidazolidin-2-one;
[(7S,9aR)-7-(4-chlorophenyl)-7-hydroxy-3,4,6,8,9,9a-hexahydro-1H-pyrido[1,2-a]pyrazin-2-yl]-[2-fluoro-3-(4-methyl-1H-pyrazol-3-yl)phenyl]methanone;
[(7S,9aR)-7-(4-chlorophenyl)-7-hydroxy-3,4,6,8,9,9a-hexahydro-1H-pyrido[1,2-a]pyrazin-2-yl]-[2-chloro-3-(4-methyl-1H-pyrazol-5-yl)phenyl]methanone;
[(7S,9aR)-7-(4-chlorophenyl)-7-hydroxy-3,4,6,8,9,9a-hexahydro-1H-pyrido[1,2-a]pyrazin-2-yl]-[3-(4-methyl-1H-pyrazol-3-yl)phenyl]methanone;
[(7R,9aR)-7-hydroxy-7-[5-(trifluoromethyl)pyridin-2-yl]-3,4,6,8,9,9a-hexahydro-1H-pyrido[1,2-a]pyrazin-2-yl]-(2-chloro-3-methoxyphenyl)methanone;
[(7S,9aS)-7-hydroxy-7-[5-(trifluoromethyl)pyridin-2-yl]-3,4,6,8,9,9a-hexahydro-1H-pyrido[1,2-a]pyrazin-2-yl]-(2-chloro-3-methoxyphenyl)methanone;
[(7R,9aR)-7-hydroxy-7-[5-(trifluoromethyl)pyridin-2-yl]-3,4,6,8,9,9a-hexahydro-1H-pyrido[1,2-a]pyrazin-2-yl]-[2-chloro-3-(1H-pyrazol-5-yl)phenyl]methanone;
[(7S,9aR)-7-(4-chlorophenyl)-7-hydroxy-3,4,6,8,9,9a-hexahydro-1H-pyrido[1,2-a]pyrazin-2-yl]-(2-fluoro-3-morpholin-4-ylphenyl)methanone;
tert-butyl4-[3-[(7S,9aR)-7-(4-chlorophenyl)-7-hydroxy-3,4,6,8,9,9a-hexahydro-1H-pyrido[1,2-a]pyrazine-2-carbonyl]-2-fluorophenyl]piperazine-1-carboxylate;
[(7S,9aR)-7-(4-chlorophenyl)-7-hydroxy-3,4,6,8,9,9a-hexahydro-1H-pyrido[1,2-a]pyrazin-2-yl]-(2-fluoro-3-piperazin-1-ylphenyl)methanone;
(2-chloro-3-methoxyphenyl)-[rac-(7R,9aS)-7-hydroxy-7-(2-methylpropyl)-3,4,6,8,9,9a-hexahydro-1H-pyrido[1,2-a]pyrazin-2-yl]methanone;
(2-chloro-3-methoxyphenyl)-[rac-(7R,9aS)-7-cyclopentyl-7-hydroxy-3,4,6,8,9,9a-hexahydro-1H-pyrido[1,2-a]pyrazin-2-yl]methanone;
(2-chloro-3-methoxyphenyl)-[rac-(7R,9aR)-7-hydroxy-7-(trifluoromethyl)-3,4,6,8,9,9a-hexahydro-1H-pyrido[1,2-a]pyrazin-2-yl]methanone;
[(7R,9aR)-7-(4-chlorophenyl)-1,3,4,6,7,8,9,9a-octahydropyrido[1,2-a]pyrazin-2-yl]-[2-bromo-3-[(Z)-2-phenylethenyl]phenyl]methanone;
[(7R,9aR)-7-(4-chlorophenyl)-1,3,4,6,7,8,9,9a-octahydropyrido[1,2-a]pyrazin-2-yl]-[2-bromo-3-[(E)-2-phenylethenyl]phenyl]methanone;
tert-butylN-[4-[(E)-2-[3-[(7R,9aR)-7-(4-chlorophenyl)-1,3,4,6,7,8,9,9a-octahydropyrido[1,2-a]pyrazine-2-carbonyl]-2-bromophenyl]ethenyl]phenyl]carbamate;
N-[4-[(E)-2-[3-[(7R,9aR)-7-(4-chlorophenyl)-1,3,4,6,7,8,9,9a-octahydropyrido[1,2-a]pyrazine-2-carbonyl]-2-bromophenyl]ethenyl]phenyl]prop-2-enamide;
4-[(E)-2-[3-[(7R,9aR)-7-(4-chlorophenyl)-1,3,4,6,7,8,9,9a-octahydropyrido[1,2-a]pyrazine-2-carbonyl]-2-bromo-phenyl]vinyl]-N-methyl-benzamide;
[(7R,9aR)-7-hydroxy-7-[5-(trifluoromethyl)pyridin-2-yl]-3,4,6,8,9,9a-hexahydro-1H-pyrido[1,2-a]pyrazin-2-yl]-[2-chloro-3-(3-hydroxyazetidin-1-yl)phenyl]methanone;
[(7S,9aR)-7-(4-chlorophenyl)-7-hydroxy-3,4,6,8,9,9a-hexahydro-1H-pyrido[1,2-a]pyrazin-2-yl]-(2-chloro-3-hydroxyphenyl)methanone;
4-(3-((7S,9aR)-7-(4-chlorophenyl)-7-hydroxyoctahydro-2H-pyrido[1,2-a]pyrazine-2-carbonyl)-2-fluorophenyl)piperazin-2-one;
4-[3-[(7S,9aR)-7-(4-chlorophenyl)-7-hydroxy-3,4,6,8,9,9a-hexahydro-1H-pyrido[1,2-a]pyrazine-2-carbonyl]-2-chlorophenyl]piperazin-2-one;
[(7S,9aR)-7-(4-chlorophenyl)-7-hydroxy-3,4,6,8,9,9a-hexahydro-1H-pyrido[1,2-a]pyrazin-2-yl]-[2-chloro-3-(6-oxa-1-azaspiro[3.3]heptan-1-yl)phenyl]methanone;
[(7S,9aS)-7-hydroxy-7-[5-(trifluoromethyl)pyridin-2-yl]-3,4,6,8,9,9a-hexahydro-1H-pyrido[1,2-a]pyrazin-2-yl]-[2-chloro-3-(difluoromethoxy)phenyl]methanone;
[(7R,9aR)-7-hydroxy-7-[5-(trifluoromethyl)pyridin-2-yl]-3,4,6,8,9,9a-hexahydro-1H-pyrido[1,2-a]pyrazin-2-yl]-[2-chloro-3-(difluoromethoxy)phenyl]methanone;

[(7S,9aR)-7-(3-chloro-4-fluorophenyl)-7-hydroxy-3,4,6,8,9,9a-hexahydro-1H-pyrido[1,2-a]pyrazin-2-yl]-[2-fluoro-3-(3-hydroxyazetidin-1-yl)phenyl]methanone;

[(7S,9aR)-7-(3-chloro-4-fluorophenyl)-7-hydroxy-3,4,6,8,9,9a-hexahydro-1H-pyrido[1,2-a]pyrazin-2-yl]-[2-chloro-3-(3-hydroxyazetidin-1-yl)phenyl]methanone;

[(7R,9aR)-7-hydroxy-7-[5-(trifluoromethyl)pyridin-2-yl]-3,4,6,8,9,9a-hexahydro-1H-pyrido[1,2-a]pyrazin-2-yl]-(2-chloro-3-fluorophenyl)methanone;

[(7S,9aS)-7-hydroxy-7-[5-(trifluoromethyl)pyridin-2-yl]-3,4,6,8,9,9a-hexahydro-1H-pyrido[1,2-a]pyrazin-2-yl]-(2-chloro-3-fluorophenyl)methanone;

[(7S,9aR)-7-(3-chloro-4-fluorophenyl)-7-hydroxy-3,4,6,8,9,9a-hexahydro-1H-pyrido[1,2-a]pyrazin-2-yl]-[2-chloro-3-[(3S)-3-hydroxypyrrolidin-1-yl]phenyl]methanone;

[(7S,9aR)-7-(3-chloro-4-fluorophenyl)-7-hydroxy-3,4,6,8,9,9a-hexahydro-1H-pyrido[1,2-a]pyrazin-2-yl]-[2-chloro-3-[(3R)-3-hydroxypyrrolidin-1-yl]phenyl]methanone;

[(7S,9aR)-7-(4-chlorophenyl)-7-hydroxy-3,4,6,8,9,9a-hexahydro-1H-pyrido[1,2-a]pyrazin-2-yl]-[2-chloro-3-[(3R)-3-hydroxypyrrolidin-1-yl]phenyl]methanone;

[(7S,9aR)-7-(4-chlorophenyl)-7-hydroxy-3,4,6,8,9,9a-hexahydro-1H-pyrido[1,2-a]pyrazin-2-yl]-[2-chloro-3-(3-hydroxy-3-methylazetidin-1-yl)phenyl]methanone;

[(7S,9aR)-7-(3-chloro-4-fluorophenyl)-7-hydroxy-3,4,6,8,9,9a-hexahydro-1H-pyrido[1,2-a]pyrazin-2-yl]-[2-chloro-3-[(3S)-3-hydroxypiperidin-1-yl]phenyl]methanone;

[(7S,9aR)-7-(3-chloro-4-fluorophenyl)-7-hydroxy-3,4,6,8,9,9a-hexahydro-1H-pyrido[1,2-a]pyrazin-2-yl]-[2-chloro-3-[(3R)-3-hydroxypiperidin-1-yl]phenyl]methanone;

[(7S,9aR)-7-(4-chlorophenyl)-7-hydroxy-3,4,6,8,9,9a-hexahydro-1H-pyrido[1,2-a]pyrazin-2-yl]-[2-chloro-3-(4-hydroxypiperidin-1-yl)phenyl]methanone;

[2-chloro-3-(3-hydroxy-3-methylpyrrolidin-1-yl)phenyl]-[rac-(7R,9aS)-7-(4-chlorophenyl)-7-hydroxy-3,4,6,8,9,9a-hexahydro-1H-pyrido[1,2-a]pyrazin-2-yl]methanone;

[(7S,9aR)-7-(3-chloro-4-fluorophenyl)-7-hydroxy-3,4,6,8,9,9a-hexahydro-1H-pyrido[1,2-a]pyrazin-2-yl]-[2-chloro-3-[(3S,4S)-3,4-dihydroxypyrrolidin-1-yl]phenyl]methanone;

[(7S,9aR)-7-(3-chloro-4-fluorophenyl)-7-hydroxy-3,4,6,8,9,9a-hexahydro-1H-pyrido[1,2-a]pyrazin-2-yl]-[2-chloro-3-[3-fluoro-3-(hydroxymethyl)azetidin-1-yl]phenyl]methanone;

[(7S,9aR)-7-(3-chloro-4-fluorophenyl)-7-hydroxy-3,4,6,8,9,9a-hexahydro-1H-pyrido[1,2-a]pyrazin-2-yl]-[2-chloro-3-[3-(hydroxymethyl)azetidin-1-yl]phenyl]methanone;

[(7S,9aR)-7-(3-chloro-4-fluorophenyl)-7-hydroxy-3,4,6,8,9,9a-hexahydro-1H-pyrido[1,2-a]pyrazin-2-yl]-[2-chloro-3-(1H-pyrazol-3-yl)phenyl]methanone;

[(7S,9aR)-7-(3-chloro-4-fluorophenyl)-7-hydroxy-3,4,6,8,9,9a-hexahydro-1H-pyrido[1,2-a]pyrazin-2-yl]-[2-fluoro-3-(1H-pyrazol-3-yl)phenyl]methanone;

[(7S,9aR)-7-(4-chlorophenyl)-7-hydroxy-3,4,6,8,9,9a-hexahydro-1H-pyrido[1,2-a]pyrazin-2-yl]-[2-fluoro-3-(1,2-thiazol-3-yl)phenyl]methanone;

[(7S,9aR)-7-(3-chloro-4-fluorophenyl)-7-hydroxy-3,4,6,8,9,9a-hexahydro-1H-pyrido[1,2-a]pyrazin-2-yl]-[2-chloro-3-(4-fluoro-1H-pyrazol-5-yl)phenyl]methanone;

[(7S,9aR)-7-(3-chloro-4-fluorophenyl)-7-hydroxy-3,4,6,8,9,9a-hexahydro-1H-pyrido[1,2-a]pyrazin-2-yl]-[2-chloro-3-(1,2,4-thiadiazol-3-yl)phenyl]methanone;

[(7S,9aR)-7-(3,4-difluorophenyl)-7-hydroxy-3,4,6,8,9,9a-hexahydro-1H-pyrido[1,2-a]pyrazin-2-yl]-(2-chloro-3-methoxyphenyl)methanone;

[(7R,9aS)-7-(3,4-difluorophenyl)-7-hydroxy-3,4,6,8,9,9a-hexahydro-1H-pyrido[1,2-a]pyrazin-2-yl]-(2-chloro-3-methoxyphenyl)methanone;

[(7S,9aR)-7-(3,4-difluorophenyl)-7-hydroxy-3,4,6,8,9,9a-hexahydro-1H-pyrido[1,2-a]pyrazin-2-yl]-[2-fluoro-3-(1H-pyrazol-5-yl)phenyl]methanone;

[(7S,9aR)-7-(3,4-difluorophenyl)-7-hydroxy-3,4,6,8,9,9a-hexahydro-1H-pyrido[1,2-a]pyrazin-2-yl]-[2-fluoro-3-(4-fluoro-1H-pyrazol-5-yl)phenyl]methanone;

[(7S,9aR)-7-(3,4-difluorophenyl)-7-hydroxy-3,4,6,8,9,9a-hexahydro-1H-pyrido[1,2-a]pyrazin-2-yl]-[2-chloro-3-(3-hydroxyazetidin-1-yl)phenyl]methanone;

[(7R,9aR)-7-hydroxy-7-[5-(trifluoromethyl)pyridin-2-yl]-3,4,6,8,9,9a-hexahydro-1H-pyrido[1,2-a]pyrazin-2-yl]-[2-chloro-3-(4-fluoro-1H-pyrazol-5-yl)phenyl]methanone;

[(7S,9aR)-7-(3-chloro-4-fluorophenyl)-7-hydroxy-3,4,6,8,9,9a-hexahydro-1H-pyrido[1,2-a]pyrazin-2-yl]-(2,3-dihydro-1H-indol-4-yl)methanone;

[(7S,9aR)-7-(4-chlorophenyl)-7-hydroxy-3,4,6,8,9,9a-hexahydro-1H-pyrido[1,2-a]pyrazin-2-yl]-[4-chloro-5-(1H-pyrazol-3-yl)pyridin-3-yl]methanone;

[(7S,9aR)-7-(4-chlorophenyl)-7-hydroxy-3,4,6,8,9,9a-hexahydro-1H-pyrido[1,2-a]pyrazin-2-yl]-[2-chloro-3-(1,2-thiazol-3-yl)phenyl]methanone;

[(7S,9aR)-7-(4-chlorophenyl)-7-hydroxy-3,4,6,8,9,9a-hexahydro-1H-pyrido[1,2-a]pyrazin-2-yl]-[2-chloro-3-(1,2-thiazol-4-yl)phenyl]methanone;

[(7R,9aR)-7-hydroxy-7-[5-(trifluoromethyl)pyridin-2-yl]-3,4,6,8,9,9a-hexahydro-1H-pyrido[1,2-a]pyrazin-2-yl]-[2-chloro-3-(1,2-thiazol-3-yl)phenyl]methanone;

[(7S,9aR)-7-(4-chlorophenyl)-7-hydroxy-3,4,6,8,9,9a-hexahydro-1H-pyrido[1,2-a]pyrazin-2-yl]-[4-methyl-5-(1H-pyrazol-3-yl)pyridin-3-yl]methanone;

(2-chloro-3-methoxyphenyl)-[rac-(7R,9aS)-7-hydroxy-7-[6-(trifluoromethyl)pyridin-3-yl]-3,4,6,8,9,9a-hexahydro-1H-pyrido[1,2-a]pyrazin-2-yl]methanone; and (2-chloro-3-methoxyphenyl)-[rac-(7R,9aR)-7-hydroxy-7-[6-(trifluoromethyl)pyridin-3-yl]-3,4,6,8,9,9a-hexahydro-1H-pyrido[1,2-a]pyrazin-2-yl]methanone;

or a pharmaceutically acceptable salt thereof.

13. The compound of claim 12, wherein the compound is selected from the group consisting of:

[(7S,9aR)-7-(3-chloro-4-fluorophenyl)-7-hydroxy-3,4,6,8,9,9a-hexahydro-1H-pyrido[1,2-a]pyrazin-2-yl]-(2-chloro-3-methoxyphenyl)methanone;

[(7R,9aS)-7-(3-chloro-4-fluorophenyl)-7-hydroxy-3,4,6,8,9,9a-hexahydro-1H-pyrido[1,2-a]pyrazin-2-yl]-(2-chloro-3-methoxyphenyl)methanone;

[(7S,9aR)-7-(4-chlorophenyl)-7-hydroxy-3,4,6,8,9,9a-hexahydro-1H-pyrido[1,2-a]pyrazin-2-yl]-[2-chloro-3-(1H-pyrazol-5-yl)phenyl]methanone;

[(7R,9aS)-7-(4-chlorophenyl)-7-hydroxy-3,4,6,8,9,9a-hexahydro-1H-pyrido[1,2-a]pyrazin-2-yl]-[2-chloro-3-(1H-pyrazol-5-yl)phenyl]methanone;

[(7S,9aR)-7-(4-chlorophenyl)-7-hydroxy-3,4,6,8,9,9a-hexahydro-1H-pyrido[1,2-a]pyrazin-2-yl]-[2-chloro-3-(3-fluoro-1H-pyrazol-4-yl)phenyl]methanone;

[(7R,9aS)-7-(4-chlorophenyl)-7-hydroxy-3,4,6,8,9,9a-hexahydro-1H-pyrido[1,2-a]pyrazin-2-yl]-[2-chloro-3-(3-fluoro-1H-pyrazol-4-yl)phenyl]methanone;

[(7S,9aR)-7-(4-chlorophenyl)-7-hydroxy-3,4,6,8,9,9a-hexahydro-1H-pyrido[1,2-a]pyrazin-2-yl]-(2-chloro-6-methoxypyridin-3-yl)methanone;

[(7S,9aR)-7-(4-chlorophenyl)-7-hydroxy-3,4,6,8,9,9a-hexahydro-1H-pyrido[1,2-a]pyrazin-2-yl]-(6-amino-2-methylpyridin-3-yl)methanone;

[(7S,9aR)-7-(4-chlorophenyl)-7-hydroxy-3,4,6,8,9,9a-hexahydro-1H-pyrido[1,2-a]pyrazin-2-yl]-[2-chloro-3-(3-hydroxyazetidin-1-yl)phenyl]methanone;

[(7S,9aR)-7-(4-chlorophenyl)-7-hydroxy-3,4,6,8,9,9a-hexahydro-1H-pyrido[1,2-a]pyrazin-2-yl]-[2-fluoro-3-(3-hydroxyazetidin-1-yl)phenyl]methanone;

5-[(7R,9aS)-7-(4-chlorophenyl)-7-hydroxy-3,4,6,8,9,9a-hexahydro-1H-pyrido[1,2-a]pyrazine-2-carbonyl]-6-chloro-1-methylpyridin-2-one;

5-[(7S,9aR)-7-(4-chlorophenyl)-7-hydroxy-3,4,6,8,9,9a-hexahydro-1H-pyrido[1,2-a]pyrazine-2-carbonyl]-6-chloro-1-methylpyridin-2-one;

3-[3-[(7S,9aR)-7-(4-chlorophenyl)-7-hydroxy-3,4,6,8,9,9a-hexahydro-1H-pyrido[1,2-a]pyrazine-2-carbonyl]-2-chlorophenyl]-1,3-oxazolidin-2-one;

1-[3-[(7S,9aR)-7-(4-chlorophenyl)-7-hydroxy-3,4,6,8,9,9a-hexahydro-1H-pyrido[1,2-a]pyrazine-2-carbonyl]-2-chlorophenyl]imidazolidin-2-one;

[(7S,9aR)-7-(4-chlorophenyl)-7-hydroxy-3,4,6,8,9,9a-hexahydro-1H-pyrido[1,2-a]pyrazin-2-yl]-[2-fluoro-3-(4-methyl-1H-pyrazol-3-yl)phenyl]methanone;

[(7S,9aR)-7-(4-chlorophenyl)-7-hydroxy-3,4,6,8,9,9a-hexahydro-1H-pyrido[1,2-a]pyrazin-2-yl]-[2-chloro-3-(4-methyl-1H-pyrazol-5-yl)phenyl]methanone;

[(7S,9aR)-7-(4-chlorophenyl)-7-hydroxy-3,4,6,8,9,9a-hexahydro-1H-pyrido[1,2-a]pyrazin-2-yl]-[3-(4-methyl-1H-pyrazol-3-yl)phenyl]methanone;

[(7R,9aR)-7-hydroxy-7-[5-(trifluoromethyl)pyridin-2-yl]-3,4,6,8,9,9a-hexahydro-1H-pyrido[1,2-a]pyrazin-2-yl]-(2-chloro-3-methoxyphenyl)methanone;

[(7S,9aS)-7-hydroxy-7-[5-(trifluoromethyl)pyridin-2-yl]-3,4,6,8,9,9a-hexahydro-1H-pyrido[1,2-a]pyrazin-2-yl]-(2-chloro-3-methoxyphenyl)methanone;

[(7R,9aR)-7-hydroxy-7-[5-(trifluoromethyl)pyridin-2-yl]-3,4,6,8,9,9a-hexahydro-1H-pyrido[1,2-a]pyrazin-2-yl]-[2-chloro-3-(1H-pyrazol-5-yl)phenyl]methanone;

[(7S,9aR)-7-(4-chlorophenyl)-7-hydroxy-3,4,6,8,9,9a-hexahydro-1H-pyrido[1,2-a]pyrazin-2-yl]-(2-fluoro-3-morpholin-4-ylphenyl)methanone;

tert-butyl4-[3-[(7S,9aR)-7-(4-chlorophenyl)-7-hydroxy-3,4,6,8,9,9a-hexahydro-1H-pyrido[1,2-a]pyrazine-2-carbonyl]-2-fluorophenyl]piperazine-1-carboxylate;

[(7S,9aR)-7-(4-chlorophenyl)-7-hydroxy-3,4,6,8,9,9a-hexahydro-1H-pyrido[1,2-a]pyrazin-2-yl]-(2-fluoro-3-piperazin-1-ylphenyl)methanone;

(2-chloro-3-methoxyphenyl)-[rac-(7R,9aS)-7-hydroxy-7-(2-methylpropyl)-3,4,6,8,9,9a-hexahydro-1H-pyrido[1,2-a]pyrazin-2-yl]methanone;

(2-chloro-3-methoxyphenyl)-[rac-(7R,9aS)-7-cyclopentyl-7-hydroxy-3,4,6,8,9,9a-hexahydro-1H-pyrido[1,2-a]pyrazin-2-yl]methanone;

(2-chloro-3-methoxyphenyl)-[rac-(7R,9aR)-7-hydroxy-7-(trifluoromethyl)-3,4,6,8,9,9a-hexahydro-1H-pyrido[1,2-a]pyrazin-2-yl]methanone;

[(7R,9aR)-7-(4-chlorophenyl)-1,3,4,6,7,8,9,9a-octahydropyrido[1,2-a]pyrazin-2-yl]-[2-bromo-3-[(Z)-2-phenylethenyl]phenyl]methanone;

[(7R,9aR)-7-(4-chlorophenyl)-1,3,4,6,7,8,9,9a-octahydropyrido[1,2-a]pyrazin-2-yl]-[2-bromo-3-[(E)-2-phenylethenyl]phenyl]methanone;

tert-butylN-[4-[(E)-2-[3-[(7R,9aR)-7-(4-chlorophenyl)-1,3,4,6,7,8,9,9a-octahydropyrido[1,2-a]pyrazine-2-carbonyl]-2-bromophenyl]ethenyl]phenyl]carbamate;

N-[4-[(E)-2-[3-[(7R,9aR)-7-(4-chlorophenyl)-1,3,4,6,7,8,9,9a-octahydropyrido[1,2-a]pyrazine-2-carbonyl]-2-bromophenyl]ethenyl]phenyl]prop-2-enamide; and 4-[(E)-2-[3-[(7R,9aR)-7-(4-chlorophenyl)-1,3,4,6,7,8,9,9a-octahydropyrido[1,2-a]pyrazine-2-carbonyl]-2-bromo-phenyl]vinyl]-N-methyl-benzamide;

or a pharmaceutically acceptable salt thereof.

14. The compound of claim 12, wherein the compound is selected from the group consisting of:

[(7R,9aR)-7-hydroxy-7-[5-(trifluoromethyl)pyridin-2-yl]-3,4,6,8,9,9a-hexahydro-1H-pyrido[1,2-a]pyrazin-2-yl]-[2-chloro-3-(3-hydroxyazetidin-1-yl)phenyl]methanone;

[(7S,9aR)-7-(4-chlorophenyl)-7-hydroxy-3,4,6,8,9,9a-hexahydro-1H-pyrido[1,2-a]pyrazin-2-yl]-(2-chloro-3-hydroxyphenyl)methanone;

4-(3-((7S,9aR)-7-(4-chlorophenyl)-7-hydroxyoctahydro-2H-pyrido[1,2-a]pyrazine-2-carbonyl)-2-fluorophenyl)piperazin-2-one;

4-[3-[(7S,9aR)-7-(4-chlorophenyl)-7-hydroxy-3,4,6,8,9,9a-hexahydro-1H-pyrido[1,2-a]pyrazine-2-carbonyl]-2-chlorophenyl]piperazin-2-one;

[(7S,9aR)-7-(4-chlorophenyl)-7-hydroxy-3,4,6,8,9,9a-hexahydro-1H-pyrido[1,2-a]pyrazin-2-yl]-[2-chloro-3-(6-oxa-1-azaspiro[3.3]heptan-1-yl)phenyl]methanone;

[(7S,9aS)-7-hydroxy-7-[5-(trifluoromethyl)pyridin-2-yl]-3,4,6,8,9,9a-hexahydro-1H-pyrido[1,2-a]pyrazin-2-yl]-[2-chloro-3-(difluoromethoxy)phenyl]methanone;

[(7R,9aR)-7-hydroxy-7-[5-(trifluoromethyl)pyridin-2-yl]-3,4,6,8,9,9a-hexahydro-1H-pyrido[1,2-a]pyrazin-2-yl]-[2-chloro-3-(difluoromethoxy)phenyl]methanone;

[(7S,9aR)-7-(3-chloro-4-fluorophenyl)-7-hydroxy-3,4,6,8,9,9a-hexahydro-1H-pyrido[1,2-a]pyrazin-2-yl]-[2-fluoro-3-(3-hydroxyazetidin-1-yl)phenyl]methanone;

[(7S,9aR)-7-(3-chloro-4-fluorophenyl)-7-hydroxy-3,4,6,8,9,9a-hexahydro-1H-pyrido[1,2-a]pyrazin-2-yl]-[2-chloro-3-(3-hydroxyazetidin-1-yl)phenyl]methanone;

[(7R,9aR)-7-hydroxy-7-[5-(trifluoromethyl)pyridin-2-yl]-3,4,6,8,9,9a-hexahydro-1H-pyrido[1,2-a]pyrazin-2-yl]-(2-chloro-3-fluorophenyl)methanone;

[(7S,9aS)-7-hydroxy-7-[5-(trifluoromethyl)pyridin-2-yl]-3,4,6,8,9,9a-hexahydro-1H-pyrido[1,2-a]pyrazin-2-yl]-(2-chloro-3-fluorophenyl)methanone;

[(7S,9aR)-7-(3-chloro-4-fluorophenyl)-7-hydroxy-3,4,6,8,9,9a-hexahydro-1H-pyrido[1,2-a]pyrazin-2-yl]-[2-chloro-3-[(3S)-3-hydroxypyrrolidin-1-yl]phenyl]methanone;

[(7S,9aR)-7-(3-chloro-4-fluorophenyl)-7-hydroxy-3,4,6,8,9,9a-hexahydro-1H-pyrido[1,2-a]pyrazin-2-yl]-[2-chloro-3-[(3R)-3-hydroxypyrrolidin-1-yl]phenyl]methanone;

[(7S,9aR)-7-(4-chlorophenyl)-7-hydroxy-3,4,6,8,9,9a-hexahydro-1H-pyrido[1,2-a]pyrazin-2-yl]-[2-chloro-3-[(3R)-3-hydroxypyrrolidin-1-yl]phenyl]methanone;

[(7S,9aR)-7-(4-chlorophenyl)-7-hydroxy-3,4,6,8,9,9a-hexahydro-1H-pyrido[1,2-a]pyrazin-2-yl]-[2-chloro-3-(3-hydroxy-3-methylazetidin-1-yl)phenyl]methanone;

[(7S,9aR)-7-(3-chloro-4-fluorophenyl)-7-hydroxy-3,4,6,8,9,9a-hexahydro-1H-pyrido[1,2-a]pyrazin-2-yl]-[2-chloro-3-[(3S)-3-hydroxypiperidin-1-yl]phenyl]methanone;

[(7S,9aR)-7-(3-chloro-4-fluorophenyl)-7-hydroxy-3,4,6,8,9,9a-hexahydro-1H-pyrido[1,2-a]pyrazin-2-yl]-[2-chloro-3-[(3R)-3-hydroxypiperidin-1-yl]phenyl]methanone;

[(7S,9aR)-7-(4-chlorophenyl)-7-hydroxy-3,4,6,8,9,9a-hexahydro-1H-pyrido[1,2-a]pyrazin-2-yl]-[2-chloro-3-(4-hydroxypiperidin-1-yl)phenyl]methanone;

[2-chloro-3-(3-hydroxy-3-methylpyrrolidin-1-yl)phenyl]-[rac-(7R,9aS)-7-(4-chlorophenyl)-7-hydroxy-3,4,6,8,9,9a-hexahydro-1H-pyrido[1,2-a]pyrazin-2-yl]methanone;

[(7S,9aR)-7-(3-chloro-4-fluorophenyl)-7-hydroxy-3,4,6,8,9,9a-hexahydro-1H-pyrido[1,2-a]pyrazin-2-yl]-[2-chloro-3-[(3S,4S)-3,4-dihydroxypyrrolidin-1-yl]phenyl]methanone;

[(7S,9aR)-7-(3-chloro-4-fluorophenyl)-7-hydroxy-3,4,6,8,9,9a-hexahydro-1H-pyrido[1,2-a]pyrazin-2-yl]-[2-chloro-3-[3-fluoro-3-(hydroxymethyl)azetidin-1-yl]phenyl]methanone;

[(7S,9aR)-7-(3-chloro-4-fluorophenyl)-7-hydroxy-3,4,6,8,9,9a-hexahydro-1H-pyrido[1,2-a]pyrazin-2-yl]-[2-chloro-3-[3-(hydroxymethyl)azetidin-1-yl]phenyl]methanone;

[(7S,9aR)-7-(3-chloro-4-fluorophenyl)-7-hydroxy-3,4,6,8,9,9a-hexahydro-1H-pyrido[1,2-a]pyrazin-2-yl]-[2-chloro-3-(1H-pyrazol-3-yl)phenyl]methanone;

[(7S,9aR)-7-(3-chloro-4-fluorophenyl)-7-hydroxy-3,4,6,8,9,9a-hexahydro-1H-pyrido[1,2-a]pyrazin-2-yl]-[2-fluoro-3-(1H-pyrazol-3-yl)phenyl]methanone;

[(7S,9aR)-7-(4-chlorophenyl)-7-hydroxy-3,4,6,8,9,9a-hexahydro-1H-pyrido[1,2-a]pyrazin-2-yl]-[2-fluoro-3-(1,2-thiazol-3-yl)phenyl]methanone;

[(7S,9aR)-7-(3-chloro-4-fluorophenyl)-7-hydroxy-3,4,6,8,9,9a-hexahydro-1H-pyrido[1,2-a]pyrazin-2-yl]-[2-chloro-3-(4-fluoro-1H-pyrazol-5-yl)phenyl]methanone;

[(7S,9aR)-7-(3-chloro-4-fluorophenyl)-7-hydroxy-3,4,6,8,9,9a-hexahydro-1H-pyrido[1,2-a]pyrazin-2-yl]-[2-chloro-3-(1,2,4-thiadiazol-3-yl)phenyl]methanone;

[(7S,9aR)-7-(3,4-difluorophenyl)-7-hydroxy-3,4,6,8,9,9a-hexahydro-1H-pyrido[1,2-a]pyrazin-2-yl]-(2-chloro-3-methoxyphenyl)methanone;

[(7R,9aS)-7-(3,4-difluorophenyl)-7-hydroxy-3,4,6,8,9,9a-hexahydro-1H-pyrido[1,2-a]pyrazin-2-yl]-(2-chloro-3-methoxyphenyl)methanone;

[(7S,9aR)-7-(3,4-difluorophenyl)-7-hydroxy-3,4,6,8,9,9a-hexahydro-1H-pyrido[1,2-a]pyrazin-2-yl]-[2-fluoro-3-(1H-pyrazol-5-yl)phenyl]methanone;

[(7S,9aR)-7-(3,4-difluorophenyl)-7-hydroxy-3,4,6,8,9,9a-hexahydro-1H-pyrido[1,2-a]pyrazin-2-yl]-[2-fluoro-3-(4-fluoro-1H-pyrazol-5-yl)phenyl]methanone;

[(7S,9aR)-7-(3,4-difluorophenyl)-7-hydroxy-3,4,6,8,9,9a-hexahydro-1H-pyrido[1,2-a]pyrazin-2-yl]-[2-chloro-3-(3-hydroxyazetidin-1-yl)phenyl]methanone;

[(7R,9aR)-7-hydroxy-7-[5-(trifluoromethyl)pyridin-2-yl]-3,4,6,8,9,9a-hexahydro-1H-pyrido[1,2-a]pyrazin-2-yl]-[2-chloro-3-(4-fluoro-1H-pyrazol-5-yl)phenyl]methanone;

[(7S,9aR)-7-(3-chloro-4-fluorophenyl)-7-hydroxy-3,4,6,8,9,9a-hexahydro-1H-pyrido[1,2-a]pyrazin-2-yl]-(2,3-dihydro-1H-indol-4-yl)methanone;

[(7S,9aR)-7-(4-chlorophenyl)-7-hydroxy-3,4,6,8,9,9a-hexahydro-1H-pyrido[1,2-a]pyrazin-2-yl]-[4-chloro-5-(1H-pyrazol-3-yl)pyridin-3-yl]methanone;

[(7S,9aR)-7-(4-chlorophenyl)-7-hydroxy-3,4,6,8,9,9a-hexahydro-1H-pyrido[1,2-a]pyrazin-2-yl]-[2-chloro-3-(1,2-thiazol-3-yl)phenyl]methanone;

[(7S,9aR)-7-(4-chlorophenyl)-7-hydroxy-3,4,6,8,9,9a-hexahydro-1H-pyrido[1,2-a]pyrazin-2-yl]-[2-chloro-3-(1,2-thiazol-4-yl)phenyl]methanone;

[(7R,9aR)-7-hydroxy-7-[5-(trifluoromethyl)pyridin-2-yl]-3,4,6,8,9,9a-hexahydro-1H-pyrido[1,2-a]pyrazin-2-yl]-[2-chloro-3-(1,2-thiazol-3-yl)phenyl]methanone;

[(7S,9aR)-7-(4-chlorophenyl)-7-hydroxy-3,4,6,8,9,9a-hexahydro-1H-pyrido[1,2-a]pyrazin-2-yl]-[4-methyl-5-(1H-pyrazol-3-yl)pyridin-3-yl]methanone;

(2-chloro-3-methoxyphenyl)-[rac-(7R,9aS)-7-hydroxy-7-[6-(trifluoromethyl)pyridin-3-yl]-3,4,6,8,9,9a-hexahydro-1H-pyrido[1,2-a]pyrazin-2-yl]methanone; and (2-chloro-3-methoxyphenyl)-[rac-(7R,9aR)-7-hydroxy-7-[6-(trifluoromethyl)pyridin-3-yl]-3,4,6,8,9,9a-hexahydro-1H-pyrido[1,2-a]pyrazin-2-yl]methanone;

or a pharmaceutically acceptable salt thereof.

15. The compound of claim 14, wherein the compound is selected from the group consisting of:

[(7R,9aR)-7-hydroxy-7-[5-(trifluoromethyl)pyridin-2-yl]-3,4,6,8,9,9a-hexahydro-1H-pyrido[1,2-a]pyrazin-2-yl]-[2-chloro-3-(3-hydroxyazetidin-1-yl)phenyl]methanone;

[(7S,9aS)-7-hydroxy-7-[5-(trifluoromethyl)pyridin-2-yl]-3,4,6,8,9,9a-hexahydro-1H-pyrido[1,2-a]pyrazin-2-yl]-[2-chloro-3-(difluoromethoxy)phenyl]methanone;

[(7R,9aR)-7-hydroxy-7-[5-(trifluoromethyl)pyridin-2-yl]-3,4,6,8,9,9a-hexahydro-1H-pyrido[1,2-a]pyrazin-2-yl]-[2-chloro-3-(difluoromethoxy)phenyl]methanone;

[(7S,9aR)-7-(3-chloro-4-fluorophenyl)-7-hydroxy-3,4,6,8,9,9a-hexahydro-1H-pyrido[1,2-a]pyrazin-2-yl]-[2-fluoro-3-(3-hydroxyazetidin-1-yl)phenyl]methanone;

[(7S,9aR)-7-(3-chloro-4-fluorophenyl)-7-hydroxy-3,4,6,8,9,9a-hexahydro-1H-pyrido[1,2-a]pyrazin-2-yl]-[2-chloro-3-(3-hydroxyazetidin-1-yl)phenyl]methanone;

[(7R,9aR)-7-hydroxy-7-[5-(trifluoromethyl)pyridin-2-yl]-3,4,6,8,9,9a-hexahydro-1H-pyrido[1,2-a]pyrazin-2-yl]-(2-chloro-3-fluorophenyl)methanone;

[(7S,9aS)-7-hydroxy-7-[5-(trifluoromethyl)pyridin-2-yl]-3,4,6,8,9,9a-hexahydro-1H-pyrido[1,2-a]pyrazin-2-yl]-(2-chloro-3-fluorophenyl)methanone;

[(7S,9aR)-7-(3-chloro-4-fluorophenyl)-7-hydroxy-3,4,6,8,9,9a-hexahydro-1H-pyrido[1,2-a]pyrazin-2-yl]-[2-chloro-3-[(3S)-3-hydroxypyrrolidin-1-yl]phenyl]methanone;

[(7S,9aR)-7-(3-chloro-4-fluorophenyl)-7-hydroxy-3,4,6,8,9,9a-hexahydro-1H-pyrido[1,2-a]pyrazin-2-yl]-[2-chloro-3-[(3R)-3-hydroxypyrrolidin-1-yl]phenyl]methanone;

[(7S,9aR)-7-(4-chlorophenyl)-7-hydroxy-3,4,6,8,9,9a-hexahydro-1H-pyrido[1,2-a]pyrazin-2-yl]-[2-chloro-3-[(3R)-3-hydroxypyrrolidin-1-yl]phenyl]methanone;

[(7S,9aR)-7-(4-chlorophenyl)-7-hydroxy-3,4,6,8,9,9a-hexahydro-1H-pyrido[1,2-a]pyrazin-2-yl]-[2-chloro-3-(3-hydroxy-3-methylazetidin-1-yl)phenyl]methanone;

[(7S,9aR)-7-(3-chloro-4-fluorophenyl)-7-hydroxy-3,4,6,8,9,9a-hexahydro-1H-pyrido[1,2-a]pyrazin-2-yl]-[2-chloro-3-[(3S)-3-hydroxypiperidin-1-yl]phenyl]methanone;

[(7S,9aR)-7-(3-chloro-4-fluorophenyl)-7-hydroxy-3,4,6,8,9,9a-hexahydro-1H-pyrido[1,2-a]pyrazin-2-yl]-[2-chloro-3-[(3R)-3-hydroxypiperidin-1-yl]phenyl]methanone;

[(7S,9aR)-7-(4-chlorophenyl)-7-hydroxy-3,4,6,8,9,9a-hexahydro-1H-pyrido[1,2-a]pyrazin-2-yl]-[2-chloro-3-(4-hydroxypiperidin-1-yl)phenyl]methanone;

[2-chloro-3-(3-hydroxy-3-methylpyrrolidin-1-yl)phenyl]-[rac-(7R,9aS)-7-(4-chlorophenyl)-7-hydroxy-3,4,6,8,9,9a-hexahydro-1H-pyrido[1,2-a]pyrazin-2-yl]methanone;

[(7S,9aR)-7-(3-chloro-4-fluorophenyl)-7-hydroxy-3,4,6,8,9,9a-hexahydro-1H-pyrido[1,2-a]pyrazin-2-yl]-[2-chloro-3-[(3S,4S)-3,4-dihydroxypyrrolidin-1-yl]phenyl]methanone;

[(7S,9aR)-7-(3-chloro-4-fluorophenyl)-7-hydroxy-3,4,6,8,9,9a-hexahydro-1H-pyrido[1,2-a]pyrazin-2-yl]-[2-chloro-3-[3-fluoro-3-(hydroxymethyl)azetidin-1-yl]phenyl]methanone;

[(7S,9aR)-7-(3-chloro-4-fluorophenyl)-7-hydroxy-3,4,6,8,9,9a-hexahydro-1H-pyrido[1,2-a]pyrazin-2-yl]-[2-chloro-3-[3-(hydroxymethyl)azetidin-1-yl]phenyl]methanone;

[(7S,9aR)-7-(3,4-difluorophenyl)-7-hydroxy-3,4,6,8,9,9a-hexahydro-1H-pyrido[1,2-a]pyrazin-2-yl]-[2-chloro-3-(3-hydroxyazetidin-1-yl)phenyl]methanone;

[(7R,9aR)-7-hydroxy-7-[5-(trifluoromethyl)pyridin-2-yl]-3,4,6,8,9,9a-hexahydro-1H-pyrido[1,2-a]pyrazin-2-yl]-[2-chloro-3-(4-fluoro-1H-pyrazol-5-yl)phenyl]methanone;

[(7R,9aR)-7-hydroxy-7-[5-(trifluoromethyl)pyridin-2-yl]-3,4,6,8,9,9a-hexahydro-1H-pyrido[1,2-a]pyrazin-2-yl]-[2-chloro-3-(1,2-thiazol-3-yl)phenyl]methanone;

(2-chloro-3-methoxyphenyl)-[rac-(7R,9aS)-7-hydroxy-7-[6-(trifluoromethyl)pyridin-3-yl]-3,4,6,8,9,9a-hexahydro-1H-pyrido[1,2-a]pyrazin-2-yl]methanone; and (2-chloro-3-methoxyphenyl)-[rac-(7R,9aR)-7-hydroxy-7-[6-(trifluoromethyl)pyridin-3-yl]-3,4,6,8,9,9a-hexahydro-1H-pyrido[1,2-a]pyrazin-2-yl]methanone;

or a pharmaceutically acceptable salt thereof.

16. A pharmaceutical composition comprising a compound of claim 1, or a pharmaceutically acceptable salt thereof, and a therapeutically inert carrier.

17. A pharmaceutical composition comprising a compound of claim 12, or a pharmaceutically acceptable salt thereof, and a therapeutically inert carrier.

* * * * *